United States Patent [19]

Colleran et al.

[11] Patent Number: 5,324,422
[45] Date of Patent: Jun. 28, 1994

[54] USER INTERFACE FOR AUTOMATED PERITONEAL DIALYSIS SYSTEMS

[75] Inventors: Lisa Colleran, Chicago; Rie Inoue, Evanston; Mark Senninger, Chicago, all of Ill.

[73] Assignee: Baxter International Inc., Deerfield, Ill.

[21] Appl. No.: 25,547

[22] Filed: Mar. 3, 1993

[51] Int. Cl.$^5$ ............................................. A61M 1/28
[52] U.S. Cl. ............................. 210/85; 210/143; 210/929; 364/413.01; 604/29
[58] Field of Search ................. 210/85, 96.1, 88, 98, 210/134, 143, 258, 929; 604/4, 28, 29; 364/413.01

[56] References Cited

U.S. PATENT DOCUMENTS

| | | | |
|---|---|---|---|
| D. 271,801 | 12/1983 | Preussner | D9/415 |
| D. 271,802 | 12/1983 | Preussner | D9/415 |
| 3,656,873 | 4/1972 | Schiff | 417/395 |
| 3,689,204 | 9/1972 | Prisk | 417/394 |
| 3,709,222 | 1/1973 | DeVries | 604/28 |
| 3,823,724 | 7/1974 | Davis | 137/15 |
| 3,882,899 | 5/1975 | Ginsberg et al. | 137/627.5 |
| 4,086,653 | 4/1978 | Gernes | 364/564 |
| 4,158,530 | 6/1979 | Bernstein | 417/389 |
| 4,199,307 | 4/1980 | Jassawalla | 417/474 |
| 4,236,880 | 12/1980 | Archibald | 417/478 |
| 4,265,601 | 5/1981 | Mandroian | 417/379 |
| 4,273,121 | 6/1981 | Jassawalla | 417/474 |
| 4,277,226 | 7/1981 | Archibald | 417/38 |
| 4,468,222 | 8/1984 | Lundquist | 417/236 |
| 4,479,760 | 10/1984 | Bilstad et al. | 417/395 |
| 4,479,761 | 10/1984 | Bilstad et al. | 417/395 |
| 4,479,762 | 10/1984 | Bilstad et al. | 417/395 |
| 4,552,552 | 11/1985 | Polaschegg et al. | 604/4 |
| 4,634,430 | 1/1987 | Polaschegg | 417/395 |
| 4,696,671 | 9/1987 | Epstein et al. | 604/67 |
| 4,778,451 | 10/1988 | Kamen | 604/67 |
| 4,808,161 | 2/1989 | Kamen | 604/67 |
| 4,816,019 | 3/1989 | Kamen | 604/65 |
| 4,818,186 | 4/1989 | Pastrone et al. | 417/63 |
| 4,826,482 | 5/1989 | Kamen | 604/67 |
| 4,828,545 | 5/1989 | Epstein et al. | 604/67 |
| 4,865,584 | 9/1989 | Epstein et al. | 604/67 |
| 4,925,152 | 5/1990 | Huber | 604/67 |
| 4,927,411 | 5/1990 | Pastrone et al. | 604/65 |
| 4,976,162 | 12/1990 | Kamen | 73/865.9 |
| 5,000,664 | 3/1991 | Lawless et al. | 417/63 |
| 5,062,774 | 11/1991 | Kramer et al. | 417/413 |
| 5,088,515 | 2/1992 | Kamen | 137/15 |
| 5,108,367 | 4/1992 | Epstein et al. | 604/67 |
| 5,141,492 | 8/1992 | Dadson et al. | 604/28 |

FOREIGN PATENT DOCUMENTS

WO86/01115 2/1986 PCT Int'l Appl. .
2093800 8/1982 United Kingdom .

*Primary Examiner*—Robert A. Dawson
*Assistant Examiner*—Sun Uk Kim
*Attorney, Agent, or Firm*—Daniel D. Ryan; Charles R. Mattenson; Paul C. Flattery

[57] ABSTRACT

Systems for performing peritoneal dialysis allow the user to chose from an array of peritoneal dialysis modalities and adjust one or more individual therapy parameters within a selected modality. Still, the systems assure that the selected modality and therapy parameters satisfy preselected composite therapy criteria.

4 Claims, 37 Drawing Sheets

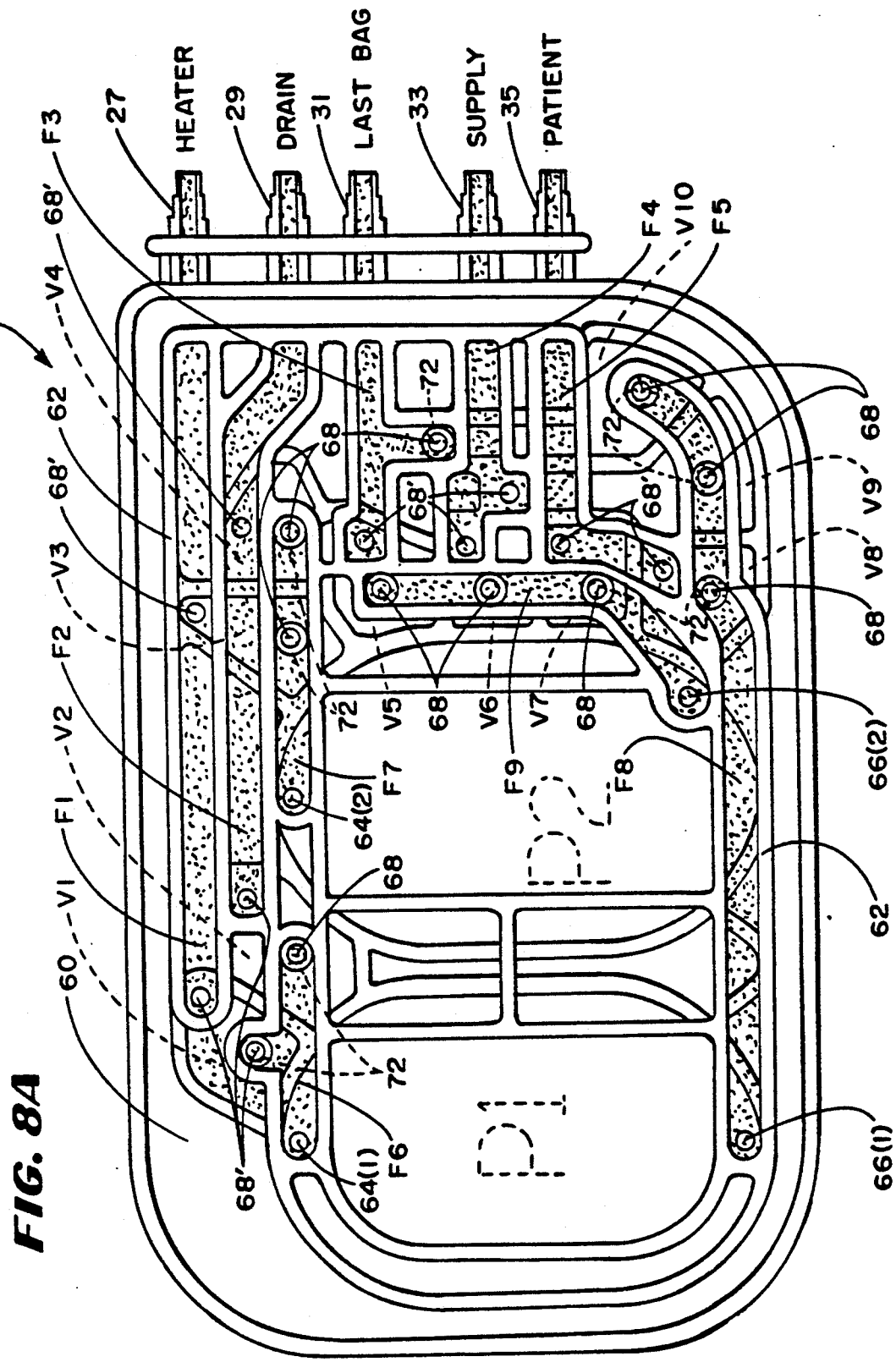

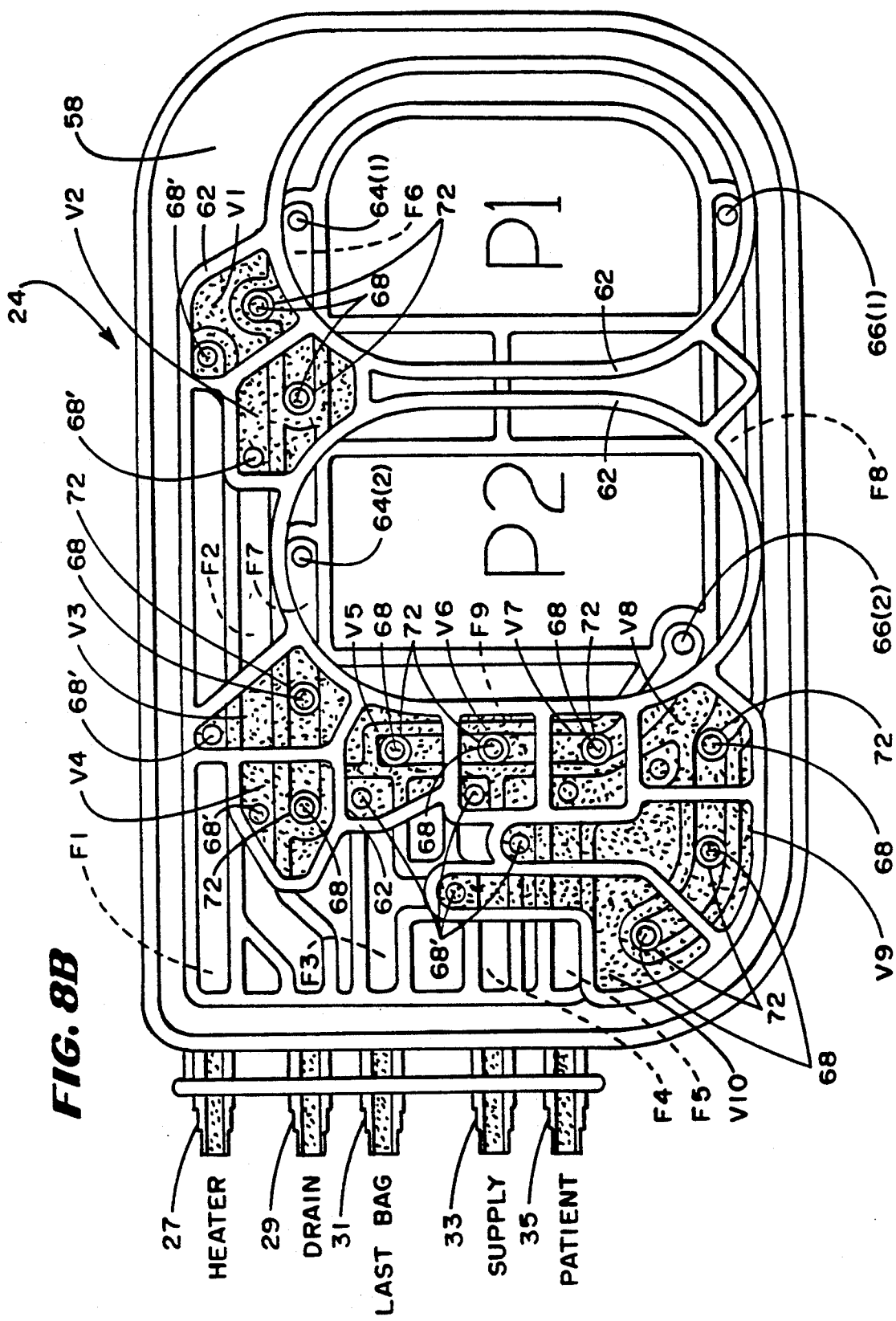

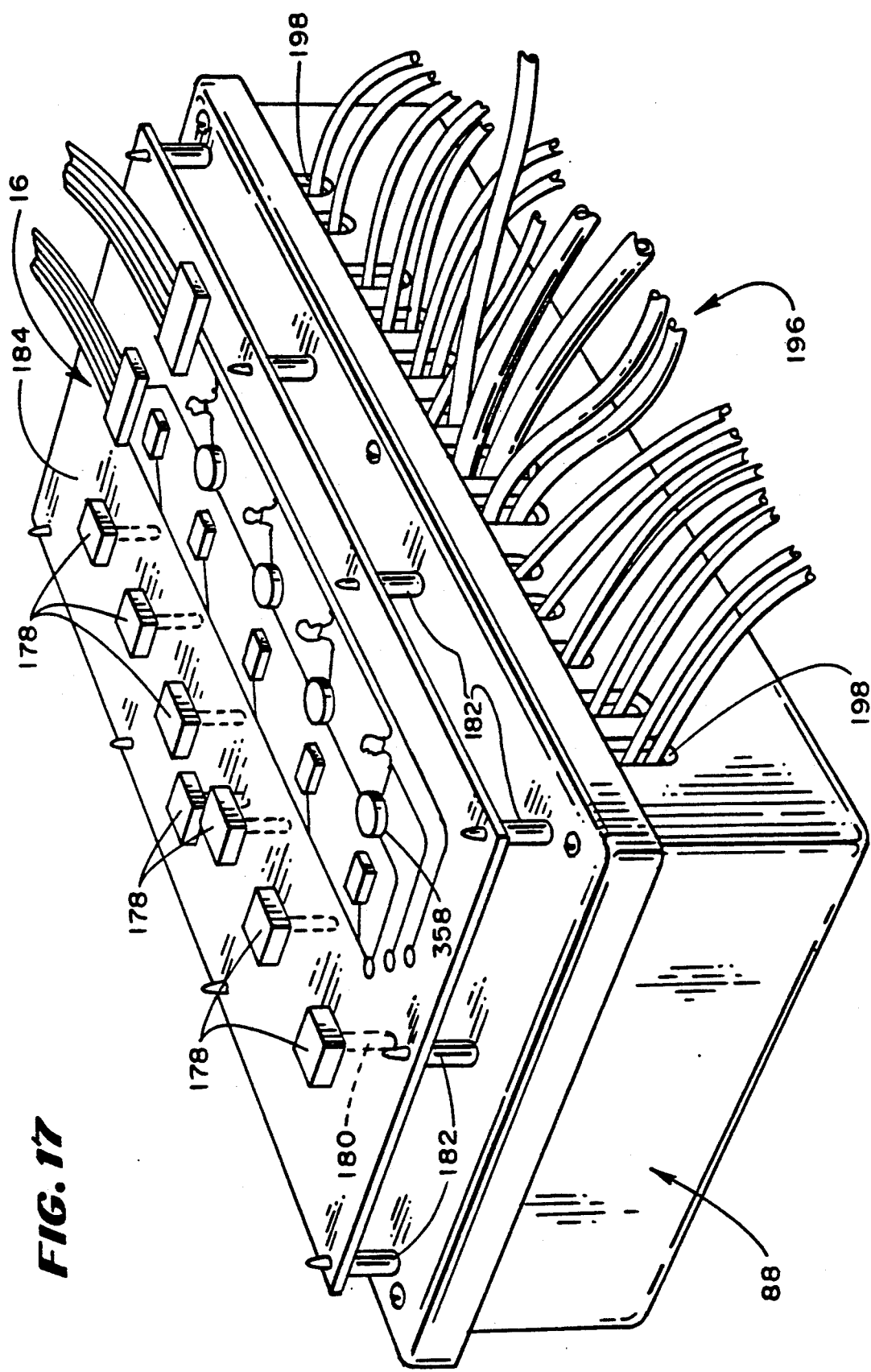

SELECT THERAPY MENU

SET UP

Run Time Menu

FIG. 29 Background Monitoring

Alarm Routines

Post-Therapy

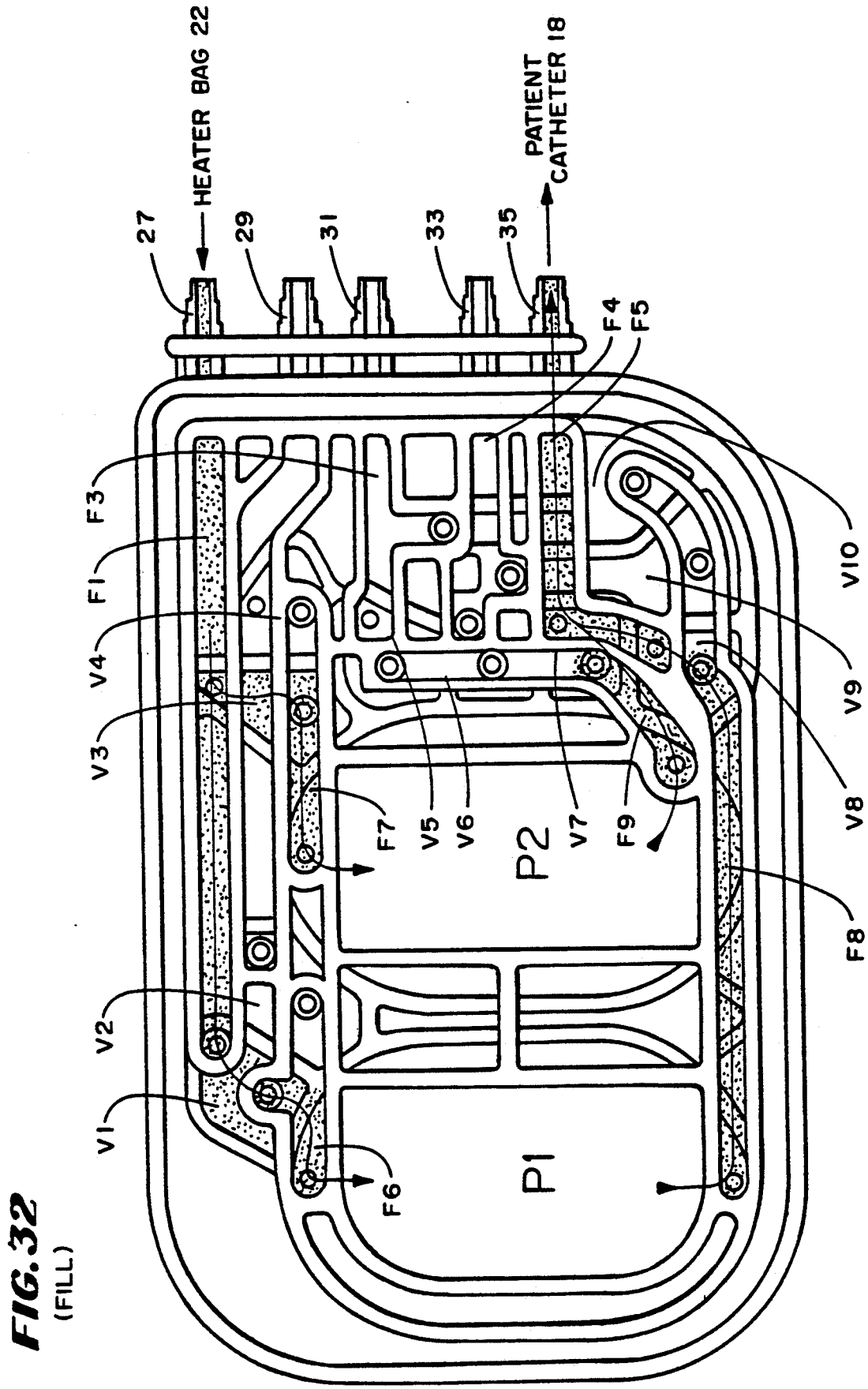
FIG.32 (FILL)

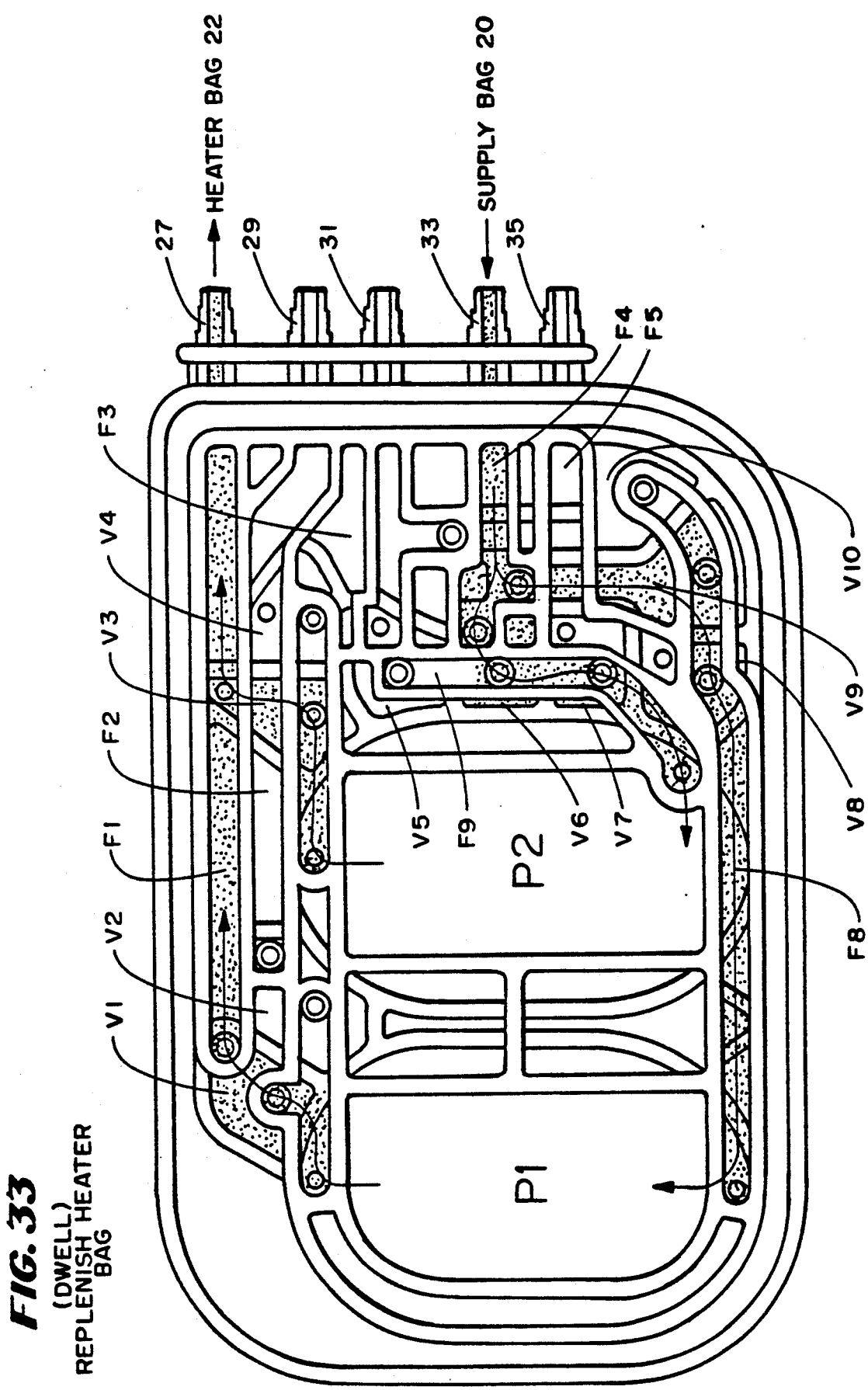
FIG. 33 (DWELL) REPLENISH HEATER BAG

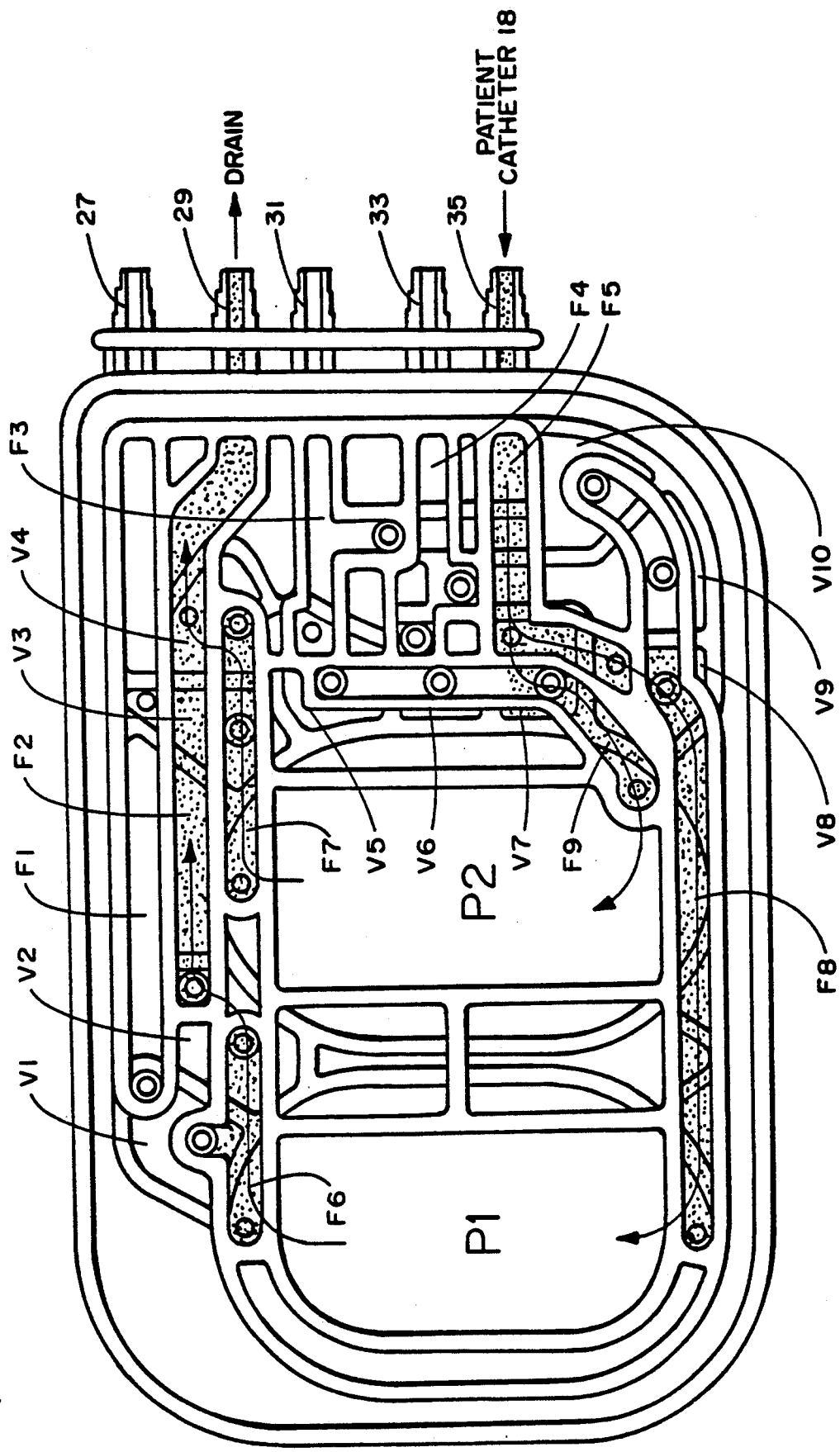
FIG. 34 (DRAIN)

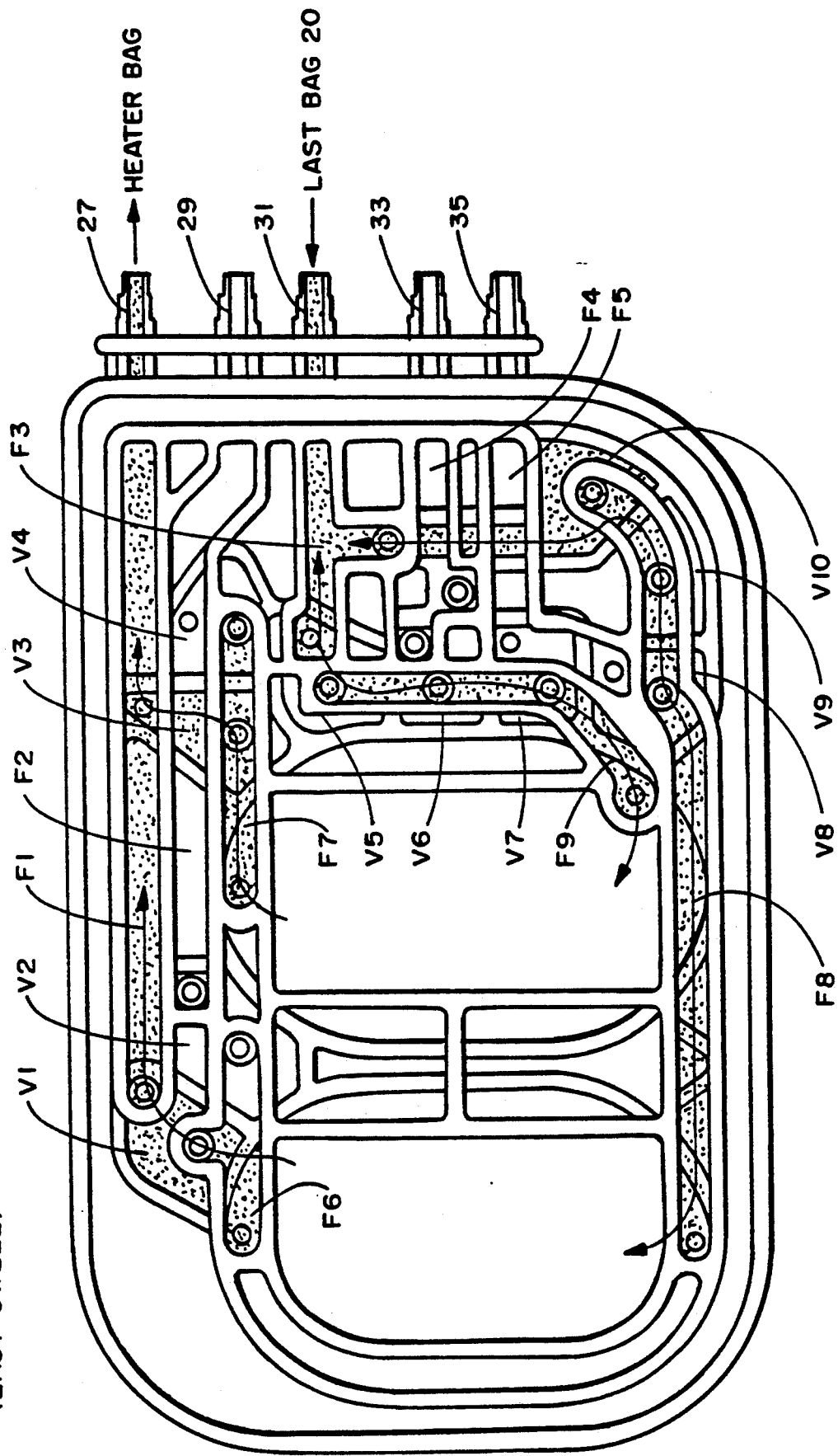
FIG. 35 (LAST DWELL)

USER INTERFACE FOR AUTOMATED PERITONEAL DIALYSIS SYSTEMS

FIELD OF THE INVENTION

This invention relates to systems and methods for performing peritoneal dialysis.

BACKGROUND OF THE INVENTION

Peritoneal Dialysis (PD) periodically infuses sterile aqueous solution into the peritoneal cavity. This solution is called peritoneal dialysis solution, or dialysate. Diffusion and osmosis exchanges take place between the solution and the bloodstream across the natural body membranes. These exchanges remove the waste products that the kidneys normally excrete. The waste products typically consist of solutes like sodium and chloride ions, and the other compounds normally excreted through the kidneys like urea, creatinine, and water. The diffusion of water across the peritoneal membrane during dialysis is called ultrafiltration.

Conventional peritoneal dialysis solutions include dextrose in concentrations sufficient to generate the necessary osmotic pressure to remove water from the patient through ultrafiltration.

Continuous Ambulatory Peritoneal Dialysis (CAPD) is a popular form of PD. A patient performs CAPD manually about four times a day. During CAPD, the patient drains spent peritoneal dialysis solution from his/her peritoneal cavity. The patient then infuses fresh peritoneal dialysis solution into his/her peritoneal cavity. This drain and fill procedure usually takes about 1 hour.

Automated Peritoneal Dialysis (APD) is another popular form of PD. APD uses a machine, called a cycler, to automatically infuse, dwell, and drain peritoneal dialysis solution to and from the patient's peritoneal cavity. APD is particularly attractive to a PD patient, because it can be performed at night while the patient is asleep. This frees the patient from the day-to-day demands of CAPD during his/her waking and working hours.

The APD sequence typically last for several hours. It often begins with an initial drain cycle to empty the peritoneal cavity of spent dialysate. The APD sequence then proceeds through a succession of fill, dwell, and drain phases that follow one after the other. Each fill/dwell/drain sequence is called a cycle.

During the fill phase, the cycler transfers a predetermined volume of fresh, warmed dialysate into the peritoneal cavity of the patient. The dialysate remains (or "dwells") within the peritoneal cavity for a time. This is called the dwell phase. During the drain phase, the cycler removes the spent dialysate from the peritoneal cavity.

The number of fill/dwell/drain cycles that are required during a given APD session depends upon the total volume of dialysate prescribed for the patient's APD regime.

APD can be and is practiced in different ways.

Continuous Cycling Peritoneal Dialysis (CCPD) is one commonly used APD modality. During each fill/dwell/drain phase of CCPD, the cycler infuses a prescribed volume of dialysate. After a prescribed dwell period, the cycler completely drains this liquid volume from the patient, leaving the peritoneal cavity empty, or "dry." Typically, CCPD employs 6 fill/dwell/drain cycles to achieve a prescribed therapy volume.

After the last prescribed fill/dwell/drain cycle in CCPD, the cycler infuses a final fill volume. The final fill volume dwells in the patient through the day. It is drained at the outset of the next CCPD session in the evening. The final fill volume can contain a different concentration of dextrose than the fill volume of the successive CCPD fill/dwell/drain fill cycles the cycler provides.

Intermittent Peritoneal Dialysis (IPD) is another APD modality. IPD is typically used in acute situations, when a patient suddenly enters dialysis therapy. IPD can also be used when a patient requires PD, but cannot undertake the responsibilities of CAPD or otherwise do it at home.

Like CCPD, IPD involves a series of fill/dwell/drain cycles. The cycles in IPD are typically closer in time than in CCPD. In addition, unlike CCPD, IPD does not include a final fill phase. In IPD, the patient's peritoneal cavity is left free of dialysate (or "dry") in between APD therapy sessions.

Tidal Peritoneal Dialysis (TPD) is another APD modality. Like CCPD, TPD includes a series of fill/dwell/drain cycles. Unlike CCPD, TPD does not completely drain dialysate from the peritoneal cavity during each drain phase. Instead, TPD establishes a base volume during the first fill phase and drains only a portion of this volume during the first drain phase. Subsequent fill/dwell/drain cycles infuse then drain a replacement volume on top of the base volume, except for the last drain phase. The last drain phase removes all dialysate from the peritoneal cavity.

There is a variation of TPD that includes cycles during which the patient is completely drained and infused with a new full base volume of dialysis.

TPD can include a final fill cycle, like CCPD. Alternatively, TPD can avoid the final fill cycle, like IPD.

APD offers flexibility and quality of life enhancements to a person requiring dialysis. APD can free the patient from the fatigue and inconvenience that the day to day practice of CAPD represents to some individuals. APD can give back to the patient his or her waking and working hours free of the need to conduct dialysis exchanges.

Still, the complexity and size of past machines and associated disposables for various APD modalities have dampened widespread patient acceptance of APD as an alternative to manual peritoneal dialysis methods.

SUMMARY OF THE INVENTION

The invention provides systems for performing peritoneal dialysis having an improved user interface and monitoring functions.

The invention provides an automated peritoneal dialysis system that allows the user to chose from an array of peritoneal dialysis modalities and adjust one or more individual therapy parameters within a selected modality. Still, the system assures that the selected modality and therapy parameters satisfy preselected composite therapy criteria.

The system includes a controller that operates in a first mode for directing operation of the actuator to conduct a first peritoneal dialysis modality. The controller operates in a second mode for directing operation of the actuator to conduct a second peritoneal dialysis modality different than the first modality.

The controller includes a first user interface for the user to select either the first mode or the second mode. The controller includes a second user interface for the user to adjust one or more therapy parameters of the selected modality.

The controller has a first verification mechanism for (i) comparing individual user-adjusted parameters to predetermined individual parameter limits; (ii) generating an error signal when an individual user-adjusted parameter is outside the associated predetermined individual parameter limits; and (iii) allowing adjustment of the individual parameter when it is within the associated predetermined individual parameter limits.

The controller also has a second verification mechanism for analyzing the individual therapy parameters allowed by the first verification mechanism to verify that the allowed individual therapy parameters taken together satisfy predetermined composite therapy criteria comprising consideration of at least resulting dwell time or required number of cycles. The second verification mechanism returns the user to the second interface to readjust one or more individual therapy parameters when the composite therapy criteria is not satisfied. The second verification mechanism permits operation of the controller in the selected mode only when the composite therapy criteria is satisfied.

Other features and advantages of the inventions are set forth in the following specification and attached drawings.

BRIEF DESCRIPTION OF THE DRAWINGS

FIG. 8A is a plan view of the one side of the cassette shown in FIG. 8, showing the liquid paths within the cassette;

FIG. 8B is a plan view of the other side of the cassette shown in FIG. 8, showing the pump chambers and valve stations within the cassette;

FIG. 17 is a perspective view of the fluid pressure manifold module housed within the cycler;

FIG. 32 is a diagrammatic representation of sequence of liquid flow through the cassette governed by the cycler controller during a typical fill phase of an APD procedure;

FIG. 33 is a diagrammatic representation of sequence of liquid flow through the cassette governed by the cycler controller during a dwell phase (replenish heater bag) of an APD procedure;

FIG. 34 is a diagrammatic representation of sequence of liquid flow through the cassette governed by the cycler controller during a drain phase of an APD procedure; and FIG. 35 is a diagrammatic representation of sequence of liquid flow through the cassette governed by the cycler controller during a last dwell of an APD procedure.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
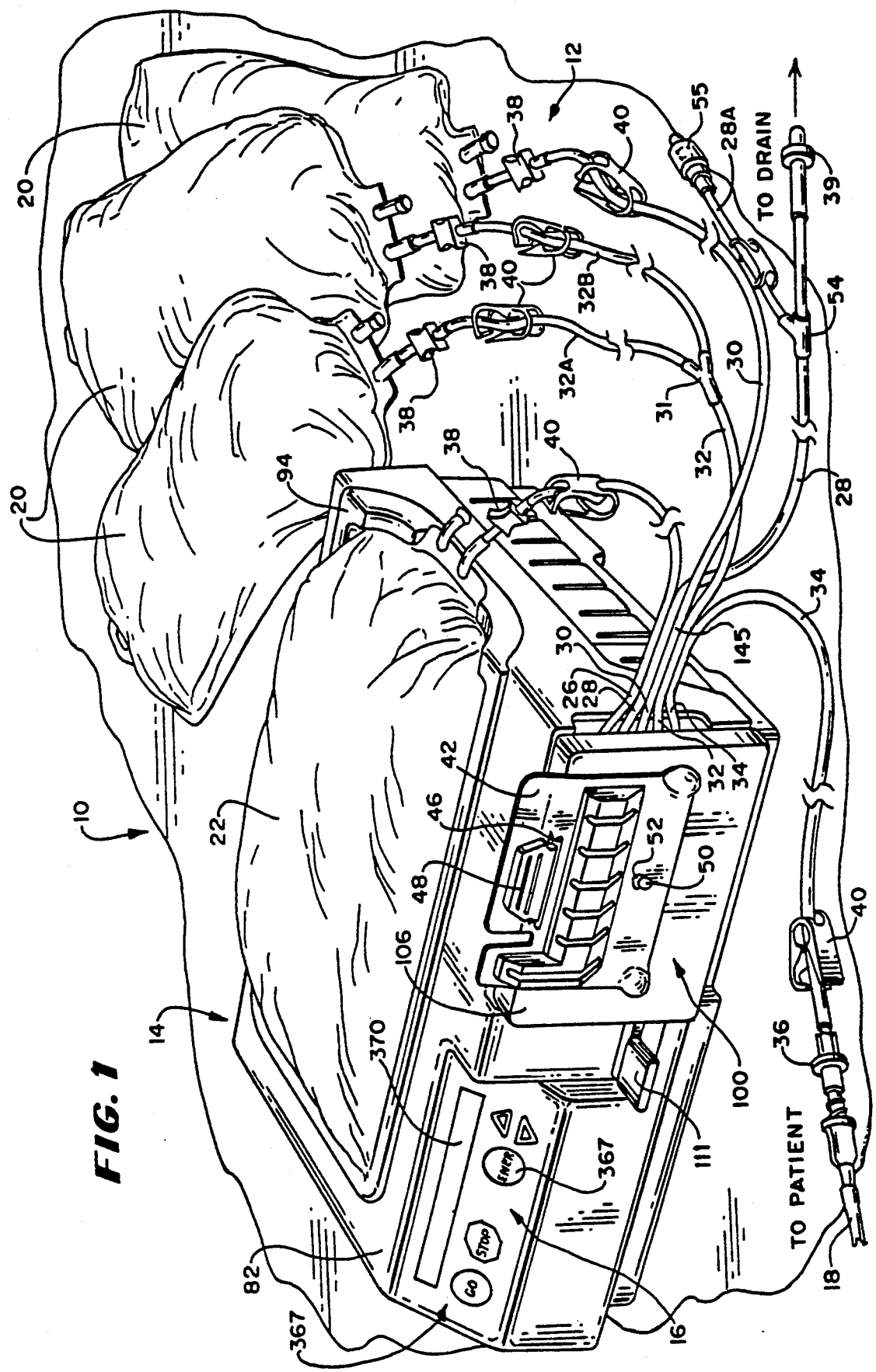
FIG. 1 is a perspective view an automated peritoneal dialysis system that embodies the features of the invention, with the associated disposable liquid delivery set ready for use with the associated cycler.

FIG. 1 shows an automated peritoneal dialysis system 10 that embodies the features of the invention. The system 10 includes three principal components. These are a liquid supply and delivery set 12; a cycler 14 that interacts with the delivery set 12 to pump liquid through it; and a controller 16 that governs the interaction to perform a selected APD procedure. In the illustrated and preferred embodiment, the cycler and controller are located within a common housing 82.

Figure 2:
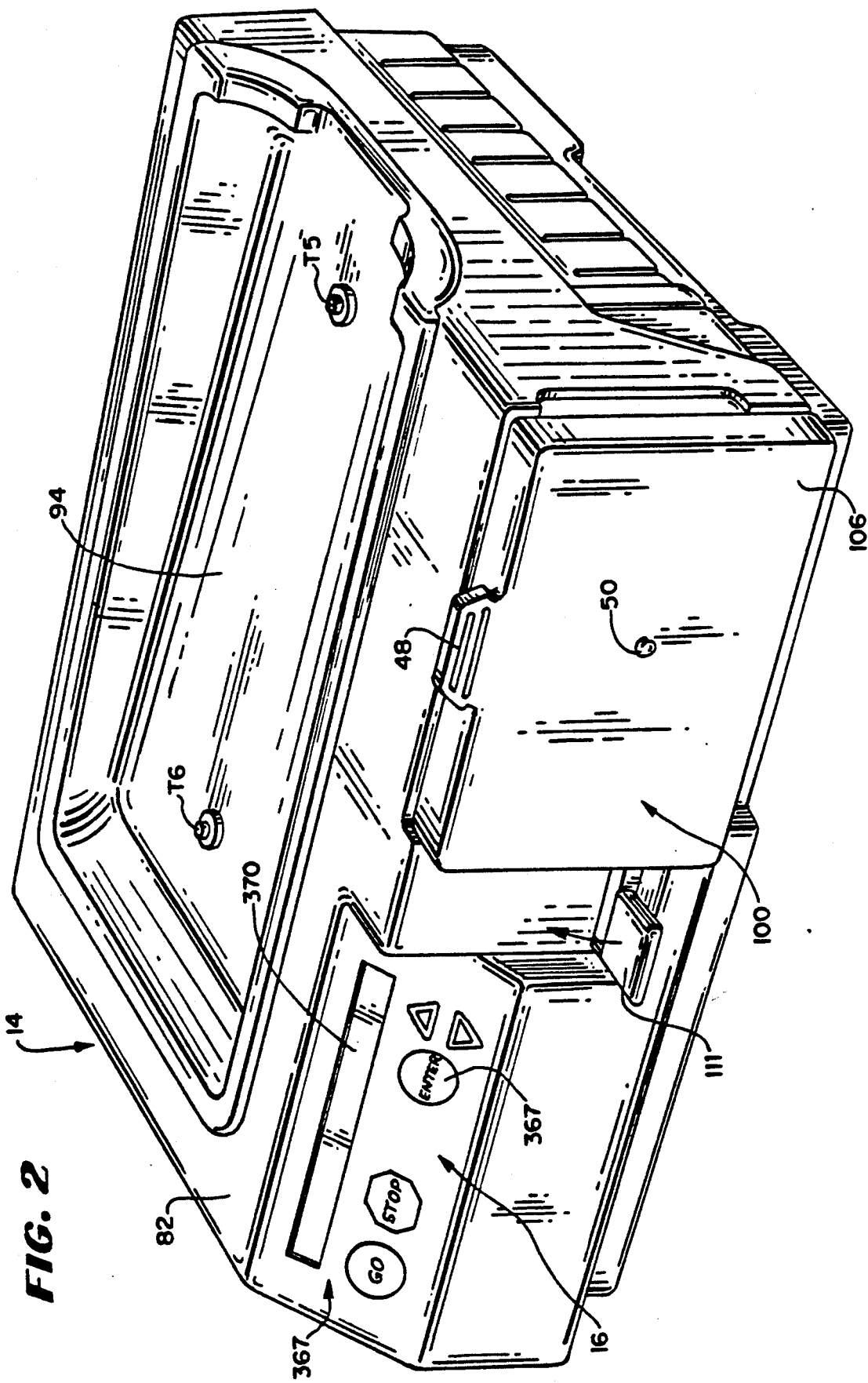
FIG. 2 is a perspective view of the cycler associated with the system shown in FIG. 1, out of association with the disposable liquid delivery set.

The cycler 14 is intended to be a durable item capable of long term, maintenance free use. As FIG. 2 shows, the cycler 14 also presents a compact footprint, suited for operation upon a table top or other relatively small surface normally found in the home. The cycler 14 is also lightweight and portable.

The set 12 is intended to be a single use, disposable item. The user loads the set 12 on the cycler 14 before beginning each APD therapy session. The user removes the set 12 from the cycler 14 upon the completing the therapy session and discards it.

In use (as FIG. 1 shows), the user connects the set 12 to his/her indwelling peritoneal catheter 18. The user also connects the set 12 to individual bags 20 containing sterile peritoneal dialysis solution for infusion. The set 12 also connects to a bag 22 in which the dialysis solution is heated to a desired temperature (typically to about 37 degrees C.) before infusion.

The controller 16 paces the cycler 14 through a prescribed series of fill, dwell, and drain cycles typical of an APD procedure.

During the fill phase, the cycler 14 infuses the heated dialysate through the set 12 and into the patient's peritoneal cavity. Following the dwell phase, the cycler 14 institutes a drain phase, during which the cycler 14 discharges spent dialysis solution from the patient's peritoneal cavity through the set into a nearby drain (not shown).

As FIG. 1 shows, the cycler 14 does not require hangers for suspending the source solution bags 20 at a prescribed head height above it. This is because the cycler 14 is not a gravity flow system. Instead, using quiet, reliable pneumatic pumping action, the cycler 14 emulates gravity flow, even when the source solution bags 20 lie right alongside it, or in any other mutual orientation.

The cycler 14 can emulate a fixed head height during a given procedure. Alternatively, the cycler 14 can change the head height to either increase or decrease the rate of flow during a procedure. The cycler 14 can emulate one or more selected head height differentials regardless of the actual head height differential existing between the patient's peritoneal cavity and the external liquid sources or destinations.

Because the cycler 14 establishes essentially an artificial head height, it has the flexibility to interact with and adapt quickly to the particular physiology and relative elevation of the patient.

The compact nature and silent, reliable operating characteristics of the cycler 14 make it ideally suited for bedside use at home while the patient is asleep.

The principal system components will now be individually discussed in greater detail.

I. THE DISPOSABLE SET

Figure 3:
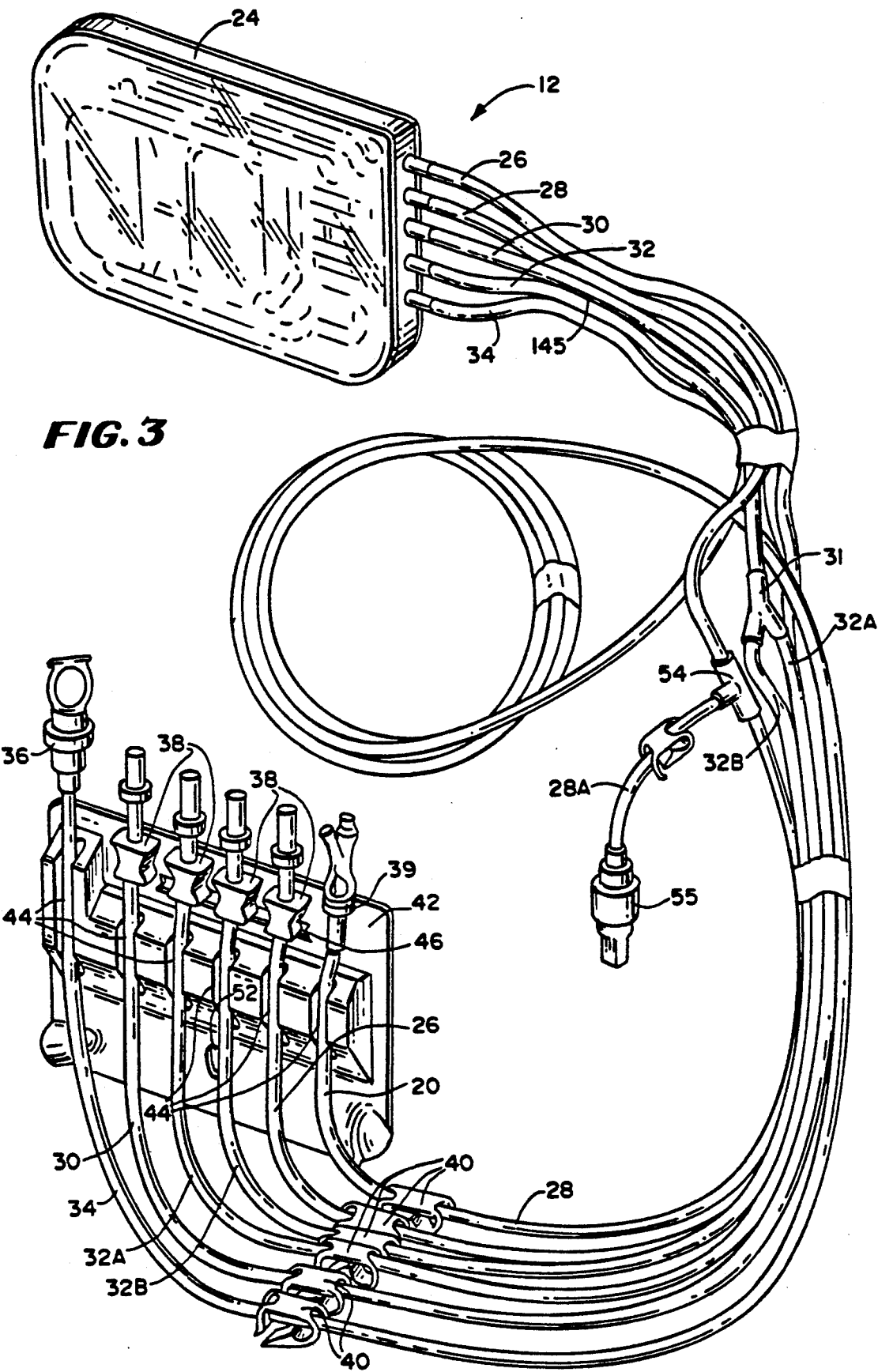
FIG. 3 is a perspective view of the disposable liquid delivery set and attached cassette that are associated with the system shown in FIG. 1.

As FIG. 3 best shows, the set 12 includes a cassette 24 to which lengths of flexible plastic tubes 26/28/30/32/34 are attached.

FIG. 3 shows the disposable liquid supply and delivery set 12 before it is readied for use in association with the cycler 14. FIG. 1 shows the disposable set 12 when readied for use in association with the cycler 14.

In use (as FIG. 1 shows), the distal ends of the tubes 26 to 34 connect outside the cycler 14 to the bags 20 of fresh peritoneal dialysis solution, to the liquid heater bag 22, to the patient's indwelling catheter 18, and to a drain (not shown).

For this reason, the tube 34 carries a conventional connector 36 for attachment to the patient's indwelling catheter 18. Other tubes 26/30/32 carry conventional connectors 38 for attachment to bag ports. Tube 32 contains a Y-connector 31, creating tubing branches 32A and 32B, each of which may connect to a bag 20.

The set 12 may contain multiple branches to accommodate attachment to multiple bags 20 of dialysis solution.

The tube 28 has a drain connector 39. It serves to discharge liquid into the external drain (not shown).

The tubing attached to the set carries an inline, manual clamp 40, except the drain tube 28.

As FIGS. 1 and 3 show, the set 12 also preferably includes a branch connector 54 on the drain tube 28. The branch connector 54 creates a tubing branch 28A that carries a connector 55. The connector 55 attaches to a mating connector on an effluent inspection bag (not shown).

Once attached, the patient can divert a volume (about 25 ml) of spent dialysate through branch 28A into the inspection bag during the first drain cycle. The bag allows the patient to inspect for cloudy effluent, which is an indication of peritonitis.

Figure 6:
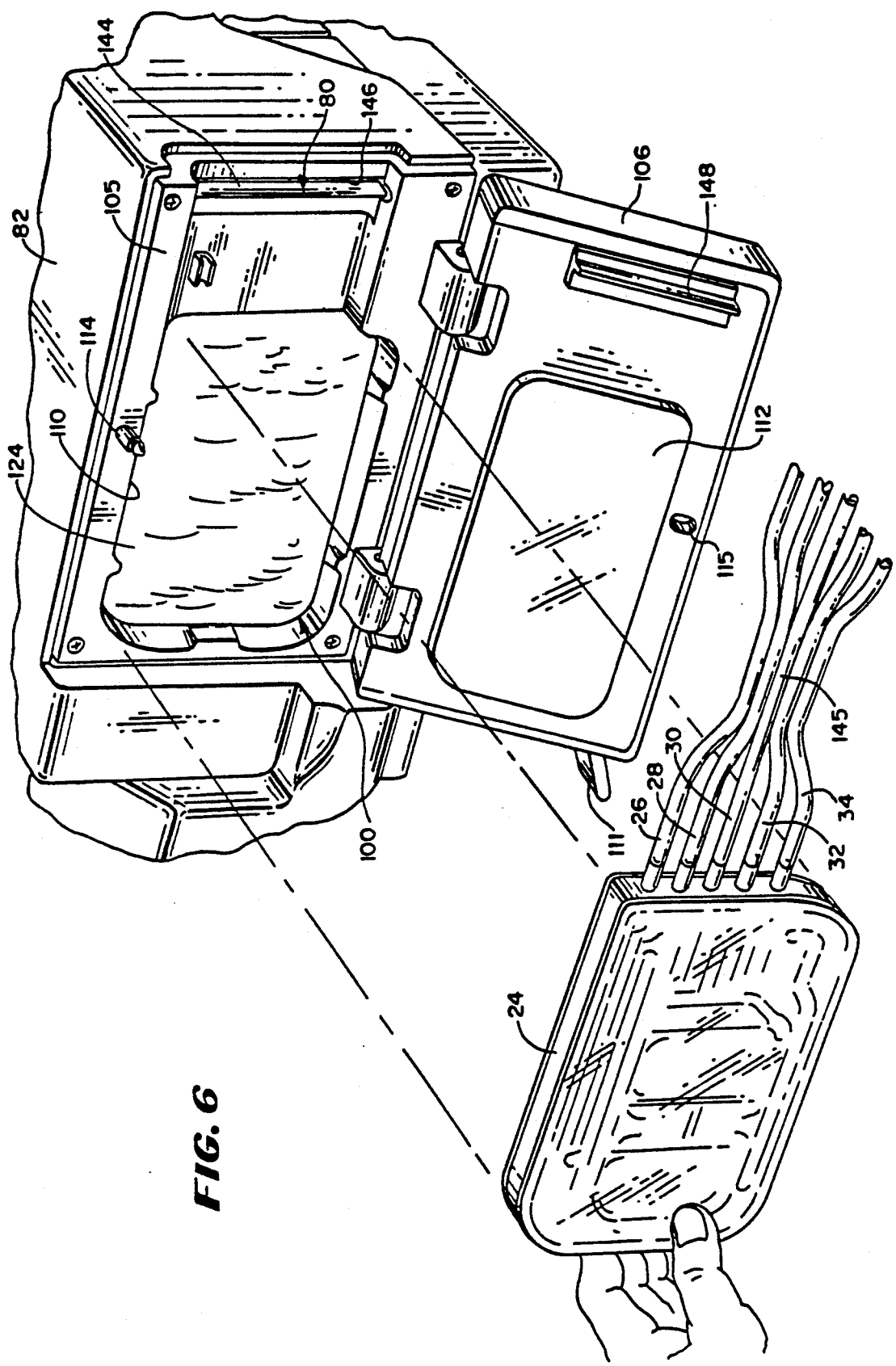
FIGS. 6 and 7 are perspective views of loading the disposable cassette attached to the set shown in FIG. 3 into the cycler for use.
Figure 7:
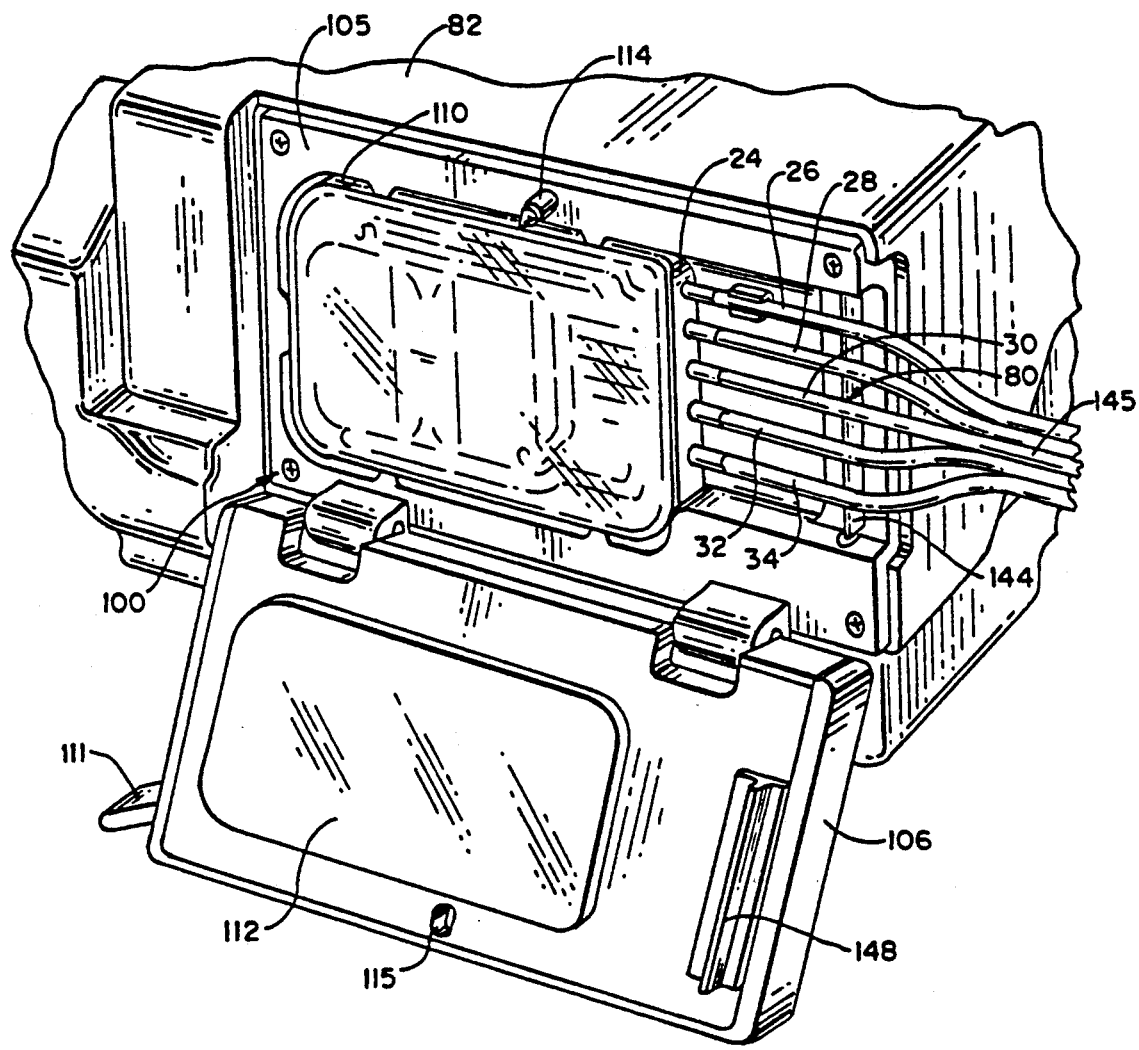

As FIGS. 6 and 7 show, in use, the cassette 24 mounts inside a holder 100 in the cycler 14 (see FIG. 1, too). The details of the holder 100 will be discussed in greater detail later. The holder 100 orients the cassette 24 for use vertically, as FIG. 7 shows.

Figure 4:
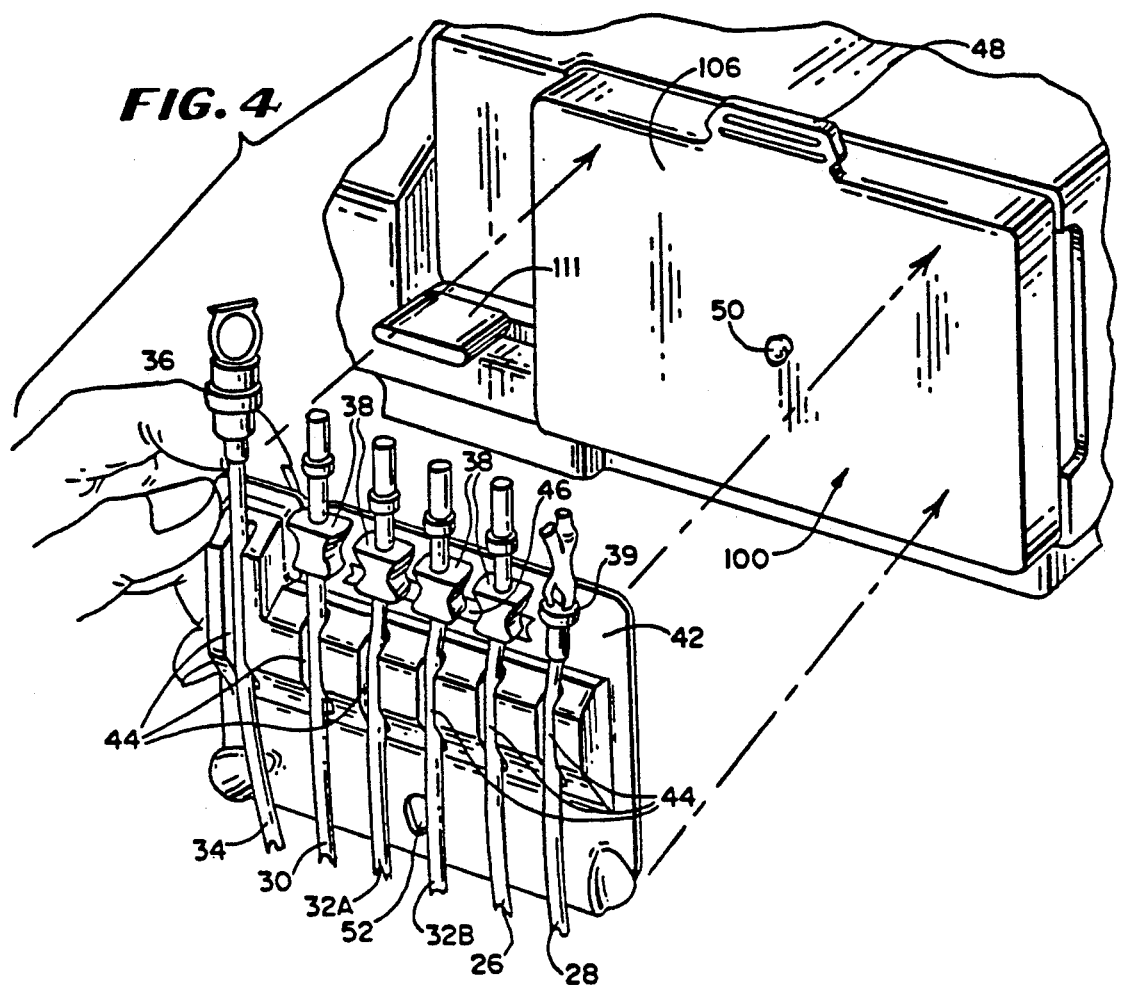
FIGS. 4 and 5 are perspective views of the organizer that is associated with the set shown in FIG. 3 in the process of being mounted on the cycler.
Figure 5:
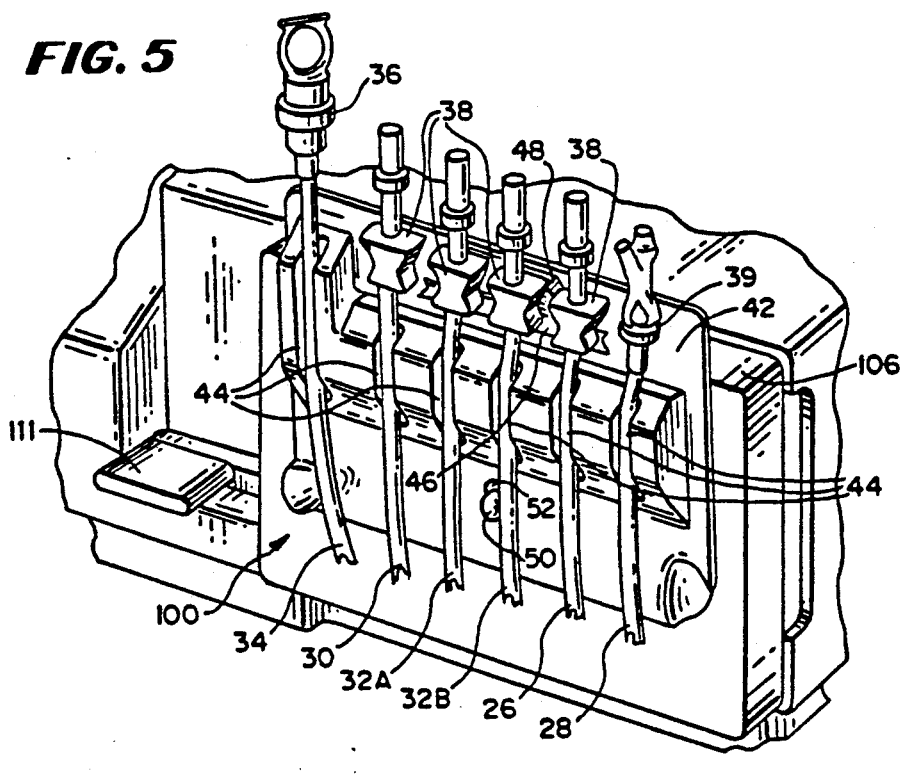

As FIGS. 3 to 5 show, the set 12 preferably includes an organizer 42 that holds the distal tube ends in a neat, compact array. This simplifies handling and shortens the set up time.

The organizer 42 includes a body with a series of slotted holders 44. The slotted holders 44 receive the distal tube ends with a friction fit.

The organizer 42 includes slot 46 that mates with a tab 48 carried on outside of the cassette holder 100. A pin 50 on the outside of the cassette holder 100 also mates with an opening 52 on the organizer 42. These attach the organizer 42 and attached tube ends to the outside of the cassette holder 100 (as FIGS. 1 and 5 show).

Once attached, the organizer 42 frees the user's hands for making the required connections with the other elements of the cycler 14. Having made the required connections, the user can remove and discard the organizer 42.

The cassette 24 serves in association with the cycler 14 and the controller 16 to direct liquid flow among the multiple liquid sources and destinations that a typical APD procedure requires. As will be described in greater detail later, the cassette 24 provides centralized valving and pumping functions in carrying out the selected APD therapy.

Figure 8:
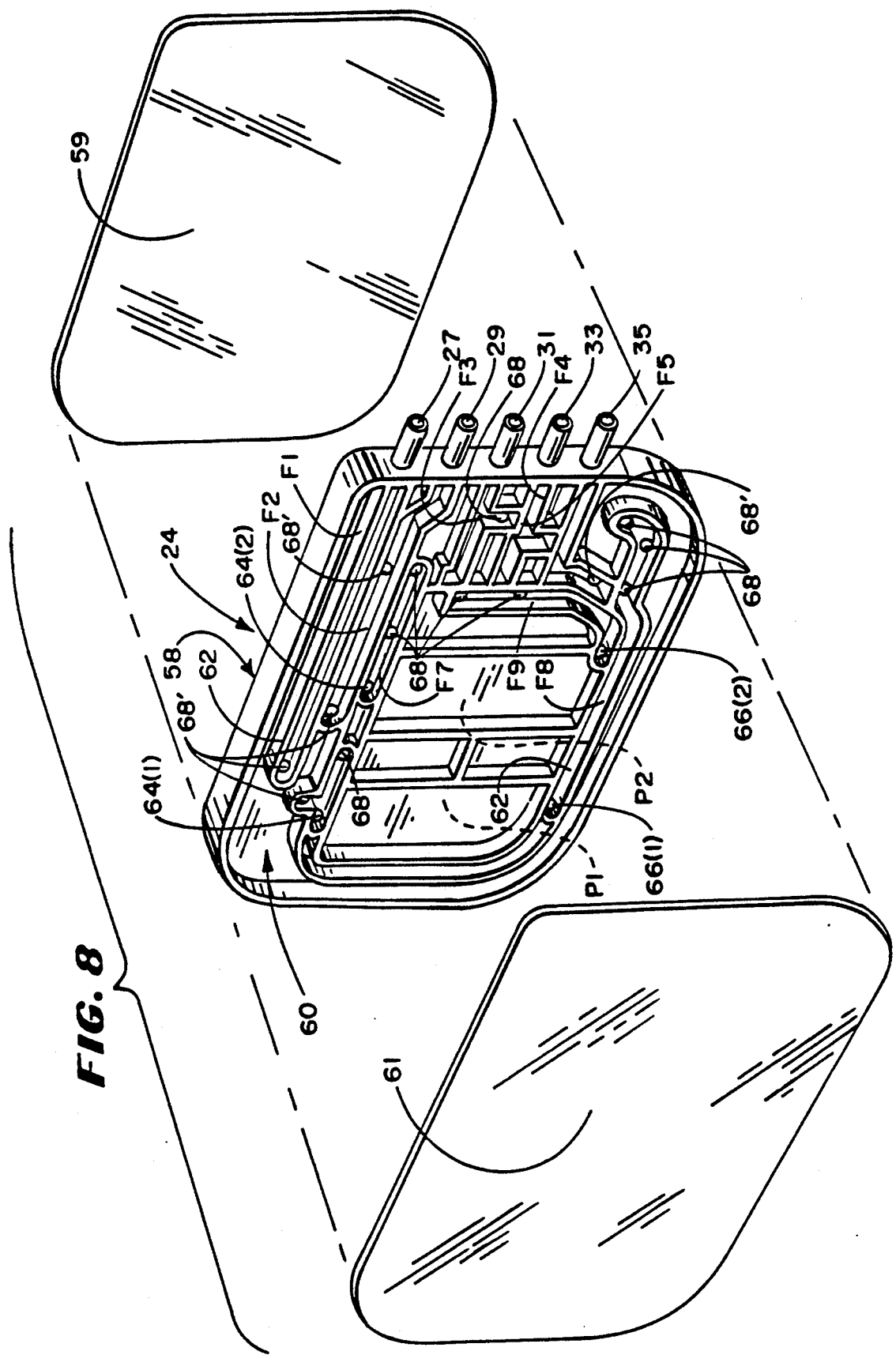
FIG. 8 is an exploded perspective view of one side of the cassette attached to the disposable set shown in FIG. 3.

FIGS. 8/8A/8B show the details of the cassette 24. As FIG. 8 shows, the cassette 24 includes an injection molded body having front and back sides 58 and 60. For the purposes of description, the front side 58 is the side of the cassette 24 that, when the cassette 24 is mounted in the holder 100, faces away from the user.

A flexible diaphragm 59 and 61 overlies the front side and back sides 58 and 60 of the cassette 24, respectively.

The cassette 24 is preferably made of a rigid medical grade plastic material. The diaphragms 59/61 are preferably made of flexible sheets of medical grade plastic. The diaphragms 59/61 are sealed about their peripheries to the peripheral edges of the front and back sides 58/60 of the cassette 24.

The cassette 24 forms an array of interior cavities in the shapes of wells and channels. The interior cavities create multiple pump chambers P1 and P2 (visible from the front side 58 of the cassette 24, as FIG. 8B shows). The interior cavities also create multiple paths F1 to F9 to convey liquid (visible from the back side 60 of the cassette 24, as FIGS. 8 and 8A shows). The interior cavities also create multiple valve stations V1 to V10 (visible from the front side 58 of the cassette 24, as FIG. 8B shows). The valve stations V1 to V10 interconnect the multiple liquid paths F1 to F9 with the pump chambers P1 and P2 and with each other.

The number and arrangement of the pump chambers, liquid paths, and valve stations can vary.

A typical APD therapy session usually requires five liquid sources/destinations. The cassette 24 that embodies the features of the invention provides these connections with five exterior liquid lines (i.e., the flexible tubes 26 to 32), two pump chambers P1 and P2, nine interior liquid paths F1 to F9, and ten valve stations V1 to V10.

The two pump chambers P1 and P2 are formed as wells that open on the front side 58 of the cassette 24. Upstanding edges 62 peripherally surround the open wells of the pump chambers P1 and P2 on the front side 58 of the cassette 24 (see FIG. 8B).

The wells forming the pump chambers P1 and P2 are closed on the back side 60 of the cassette 24 (see FIG. 8), except that each pump chamber P1 and P2 includes a vertically spaced pair of through holes or ports 64/66 that extend through to the back side 60 of the cassette 24.

As FIGS. 8/8A/8B show, vertically spaced ports 64(1) and 66(1) are associated with pump chamber P1. Port 64(1) communicates with liquid path F6, while port 66(1) communicates with liquid path F8.

As FIGS. 8/8A/8B also show, vertically spaced ports 64(2) and 66(2) are associated with pump chamber P2. Port 64(2) communicates with liquid path F7, while port 66(2) communicates with liquid path F9.

As will become apparent, either port 64(1)/(2) or 66(1)/(2) can serve its associated chamber P1/P2 as an inlet or an outlet. Alternatively, liquid can be brought into and discharged out of the chamber P1/P2 through the same port associated 64(1)/(2) or 66(1)/(2).

In the illustrated and preferred embodiment, the ports 64/66 are spaced so that, when the cassette 24 is oriented vertically for use, one port 64(1)/(2) is located higher than the other port 66(1)/(2) associated with that pump chamber P1/P2. As will be described in greater detail later, this orientation provides an important air removal function.

Figure 8C:
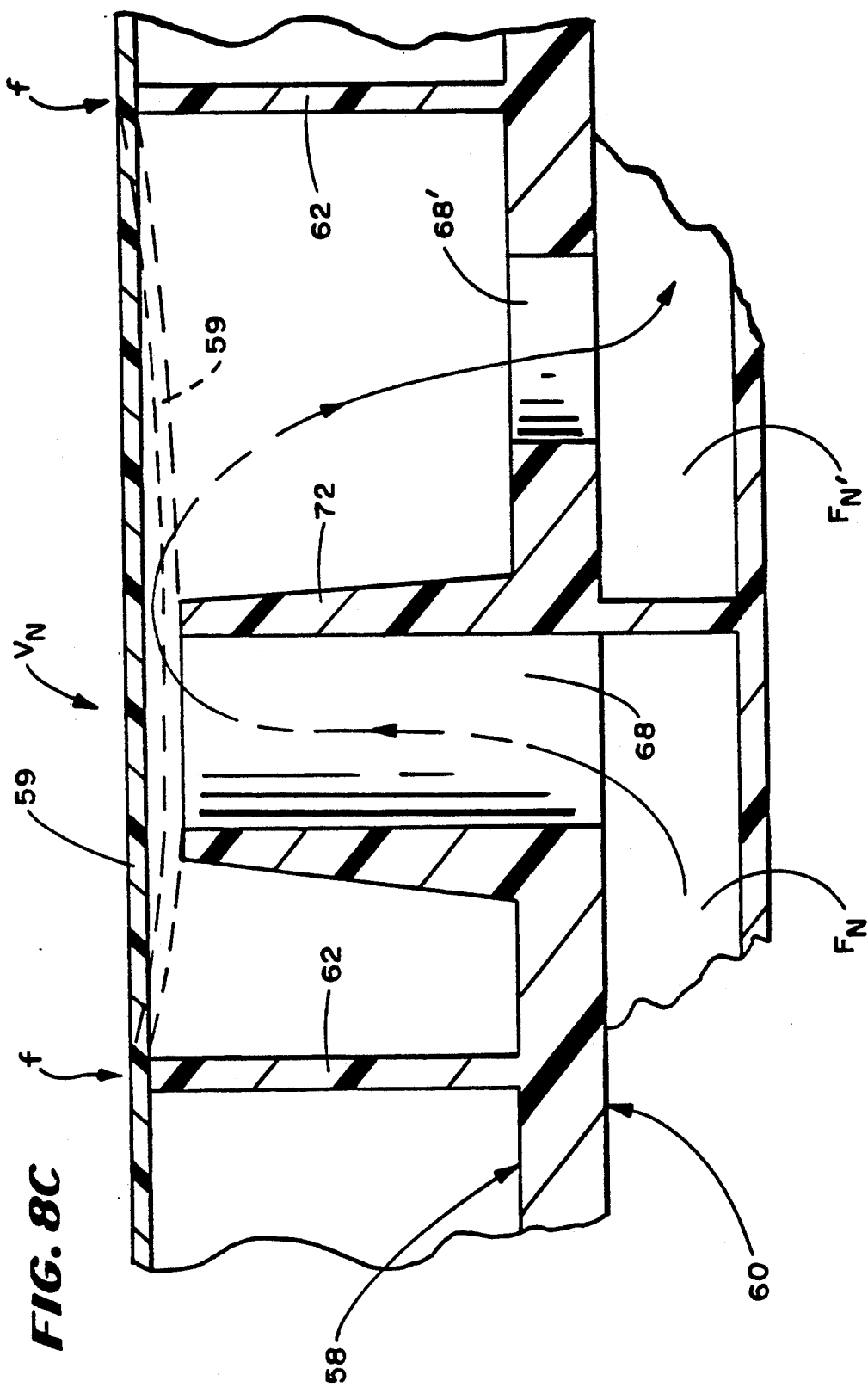
FIG. 8C is an enlarged side section view of a typical cassette valve station shown in FIG. 8B.

The ten valve stations V1 to V10 are likewise formed as wells open on the front side 58 of the cassette 24. FIG. 8C shows a typical valve station $V_N$. As FIG. 8C best shows, upstanding edges 62 peripherally surround the open wells of the valve stations V1 to V10 on the front side 58 of the cassette 24.

As FIG. 8C best shows, the valve stations V1 to V10 are closed on the back side 60 of the cassette 24, except that each valve station $V_N$ includes a pair of through holes or ports 68 and 68'. One port 68 communicates with a selected liquid path $F_N$ on the back side 60 of the cassette 24. The other port 68' communicates with another selected liquid path $F_{N'}$ on the back side 60 of the cassette 24.

In each valve station $V_N$, a raised valve seat 72 surrounds one of the ports 68. As FIG. 8C best shows, the valve seat 72 terminates lower than the surrounding peripheral edges 62. The other port 68' is flush with the front side 58 of the cassette.

As FIG. 8C continues to show best, the flexible diaphragm 59 overlying the front side 58 of the cassette 24 rests against the upstanding peripheral edges 62 surrounding the pump chambers and valve stations. With the application of positive force uniformly against this side 58 of the cassette 24 (as shown by the f-arrows in FIG. 8C), the flexible diaphragm 59 seats against the upstanding edges 62. The positive force forms peripheral seals about the pump chambers P1 and P2 and valve stations V1 to V10. This, in turn, isolates the pump chambers P1 and P2 and valve stations V1 to V10 from each other and the rest of the system. The cycler 14 applies positive force to the front cassette side 58 for this very purpose.

Further localized application of positive and negative fluid pressures upon the regions of the diaphragm 59 overlying these peripherally sealed areas serve to flex the diaphragm regions within these peripherally sealed areas.

These localized applications of positive and negative fluid pressures on the diaphragm regions overlying the pump chambers P1 and P2 serve to move liquid out of and into the chambers P1 and P2.

Likewise, these localized applications of positive and negative fluid pressure on the diaphragm regions overlying the valve stations V1 to V10 will serve to seat and unseat these diaphragm regions against the valve seats 72, thereby closing and opening the associated valve port 68. FIG. 8C shows in solid and phantom lines the flexing of the diaphragm 59 relative to a valve seat 72.

In operation, the cycler 14 applies localized positive and negative fluid pressures to the diaphragm 59 for opening and closing the valve ports.

The liquid paths F1 to F9 are formed as elongated channels that are open on the back side 60 of the cassette 24. Upstanding edges 62 peripherally surround the open channels on the back side 60 of the cassette 24.

The liquid paths F1 to F9 are closed on the front side 58 of the cassette 24, except where the channels cross over valve station ports 68/68' or pump chamber ports 64(1)/(2) and 66(1)/(2).

The flexible diaphragm 61 overlying the back side 60 of the cassette 24 rests against the upstanding peripheral edges 62 surrounding the liquid paths F1 to F9. With the application of positive force uniformly against this side 60 of the cassette 24, the flexible diaphragm 61 seats against the upstanding edges 62. This forms peripheral seals along the liquid paths F1 to F9. In operation, the cycler 14 also applies positive force to the diaphragm 61 for this very purpose.

As FIGS. 8/8A/8B show, five premolded tube connectors 27/29/31/33/35 extend out along one side edge of the cassette 24. When the cassette 24 is vertically oriented for use, the tube connectors 27 to 35 are vertically stacked one above the other. The first tube connector 27 is the uppermost connector, and the fifth tube connector 35 is the lowermost connector.

This ordered orientation of the tube connectors 27 to 35 provides a centralized, compact unit. It also makes it possible to cluster the valve stations within the cassette 24 near the tube connectors 27 to 35.

The first through fifth tube connectors 27 to 35 communicate with interior liquid paths F1 to F5, respectively. These liquid paths F1 to F5 constitute the primary liquid paths of the cassette 24, through which liquid enters or exits the cassette 24.

The remaining interior liquid paths F6 to F9 of the cassette 24 constitute branch paths that link the primary liquid paths F1 to F5 to the pump chambers P1 and P2 through the valve stations V1 to V10.

Because the pump chambers P1 and P2 are vertically oriented during use, air entering the pump chambers P1/P2 during liquid pumping operations will accumulate near the upper port 64 in each pump chamber P1/P2.

The liquid paths F1 to F9 and the valve stations V1 to V10 are purposefully arranged to isolate the patient's peritoneal cavity from the air that the pump chambers P1/P2 collect. They are also purposefully arranged so that this collected air can be transferred out of the pump chambers P1/P2 during use.

More particularly, the cassette 24 isolates selected interior liquid paths from the upper ports 64 of the pump chambers P1 and P2 The cassette 24 thereby isolates these selected liquid paths from the air that accumulates in the pump chambers P1/P2. These air-isolated liquid paths can be used to convey liquid directly into and from the patient's peritoneal cavity.

The cassette 24 also connects other selected liquid paths only to the upper ports 64(I)/(2) of the pump chambers P1 and P2. These liquid paths can be used to transfer air out of the respective pump chamber P1/P2. These liquid paths can also be used to convey liquid away from the patient to other connected elements in the system 10, like the heater bag 22 or the drain.

In this way, the cassette 24 serves to discharge entrapped air through established noncritical liquid paths, while isolating the critical liquid paths from the air. The cassette 24 thereby keeps air from entering the patient's peritoneal cavity.

More particularly, valve stations V1 to V4 serve only the upper ports 64(1)/(2) of both pump chambers P1 and P2. These valve stations V1 to V4, in turn, serve only the primary liquid paths F1 and F2. Branch liquid path F6 links primary paths F1 and F2 with the upper port 64(1) of pump chamber P1 through valve stations V1 and V2. Branch liquid path F7 links primary paths F1 and F2 with the upper port 64(2) of pump chamber P2 through valve stations V3 and V4.

These primary paths F1 and F2 can thereby serve as noncritical liquid paths, but not as critical liquid paths, since they are not isolated from air entrapped within the pumping chambers P1/P2. By the same token, the primary paths F1 and F2 can serve to convey entrapped air from the pump chambers P1 and P2.

Tubes that, in use, do not directly convey liquid to the patient can be connected to the noncritical liquid paths F1 and F2 through the upper two connectors 27 and 29. One tube 26 conveys liquid to and from the heater bag 22. The other tube 28 conveys spent peritoneal solution to the drain.

When conveying liquid to the heater bag 22 or to the drain, these tubes 26/28 can also carry air that accumulates in the upper region of the pump chambers P1/P2. In this arrangement, the heater bag 22, like the drain, serves as an air sink for the system 10.

Valve stations V5 to V10 serve only the lower ports 66(1)/(2) of both pump chambers P1 and P2. These valve stations V5 to V10, in turn, serve only the primary liquid paths F3; F4; and F5. Branch liquid path F8 links primary paths F3 to F5 with the lower port 66(1) of pump chamber P1 through valve stations V8; V9; and V10. Branch liquid path F9 links primary paths F3 to F5 with the lower port 66(2) of pump chamber P2 through valve stations V5; V6; and V7.

Because the primary paths F3 to F5 are isolated from communication with the upper ports 64 of both pump chambers P1 and P2, they can serve as critical liquid paths.

Thus, the tube 34 that conveys liquid directly to the patient's indwelling catheter can be connected to one of the lower three connectors 31/33/35 (i.e., to the primary liquid paths F3 to F5).

The same tube 34 also carries spent dialysate from the patient's peritoneal cavity. Likewise, the tubes 30/32 that carry sterile source liquid into the pump chambers enter through the lower pump chamber ports 66(1)/(2).

This arrangement makes it unnecessary to incorporate bubble traps and air vents in the tubing serving the cassette. The cassette is its own self contained air trap.

II. THE CYCLER

Figure 9:
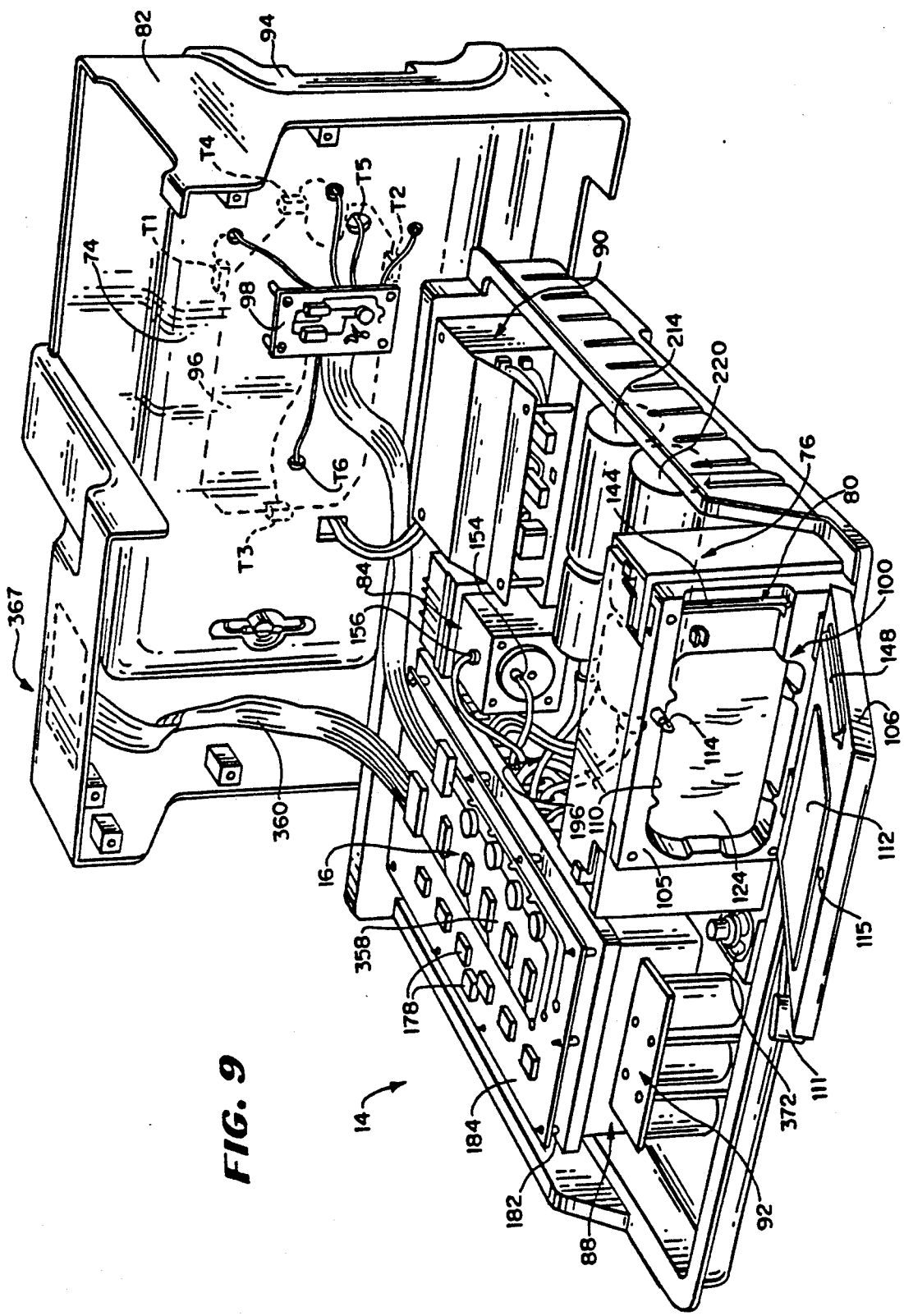
FIG. 9 is perspective view of the cycle shown in FIG. 2 with its housing removed to show its interior.
Figure 10:
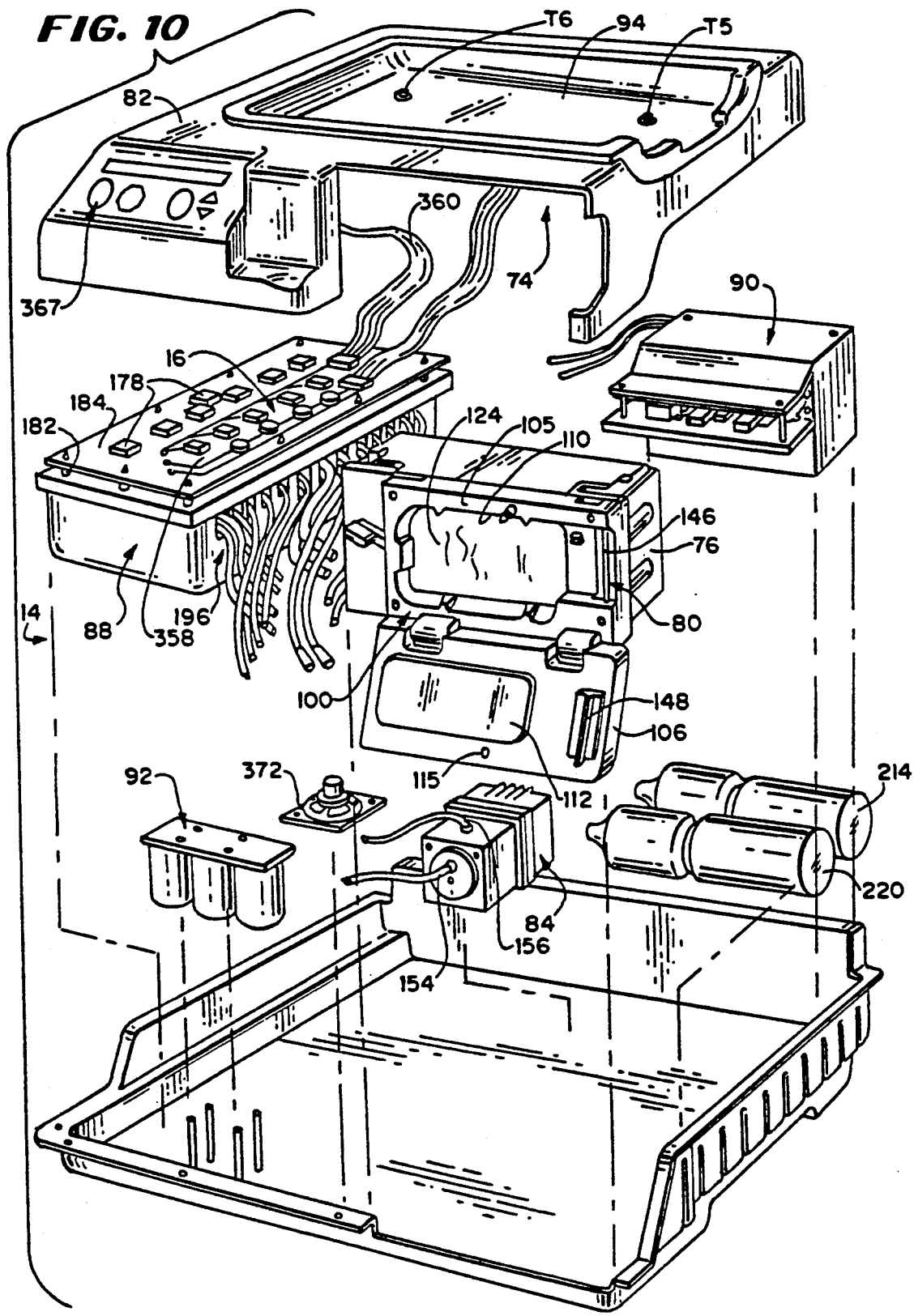
FIG. 10 is an exploded perspective view showing the main operating modules housed within the interior of the cycler.

As FIGS. 9 and 10 best show, the cycler 14 carries the operating elements essential for an APD procedure within a portable housing 82 that occupies a relatively small footprint area (as FIGS. 1 and 2 also show).

As already stated, the housing 82 encloses the cycle controller 16.

The housing 82 also encloses a bag heater module 74 (see FIG. 9). It further encloses a pneumatic actuator module 76. The pneumatic actuator module 76 also incorporates the cassette holder 100 already described, as well as a failsafe liquid shutoff assembly 80, which will be described later.

The housing 82 also encloses a source 84 of pneumatic pressure and an associated pneumatic pressure distribution module 88, which links the pressure source 84 with the actuator module 76.

The housing 82 also encloses an AC power supply module 90 and a back-up DC battery power supply module 92 for the cycler 14.

Further structural and functional details of these operating modules of the cycler 14 will be described next.

(A) The Bag Heating Module

The bag heating module 74 includes an exterior support plate 94 on the top of the cycler housing 82 for carrying the heater bag 22 (as FIG. 1 shows). The support plate 94 is made of a heat conducting material, like aluminum.

As FIG. 9 shows, the module 74 includes a conventional electrical resistance heating strip 96 that underlies and heats the support plate 94.

Four thermocouples T1/T2/T3/T4 monitor the temperatures at spaced locations on the left, right, rear, and center of the heating strip 96. Fifth and sixth thermocouples T5/T6 (see FIGS. 2 and 10) independently monitor the temperature of the heater bag 22 itself.

A circuit board 98 (see FIG. 9) receives the output of the thermocouples T1 to T6. The board 98 conditions the output before transmitting it to the controller 16 for processing.

In the preferred embodiment, the controller 16 includes a heater control algorithm that elevates the temperature of liquid in the heater bag 22 to about 33 degrees C. before the first fill cycle. A range of other safe temperature settings could be used, which could be selected by the user. The heating continues as the first fill cycle proceeds until the heater bag temperature reaches 36 degrees C.

The heater control algorithm then maintains the bag temperature at about 36 degrees C. The algorithm functions to toggle the heating strip 96 on and off at a sensed plate temperature of 44 degrees C. to assure that plate temperature never exceeds 60 degrees C.

(B) The Pneumatic Actuator Module

Figure 12A:
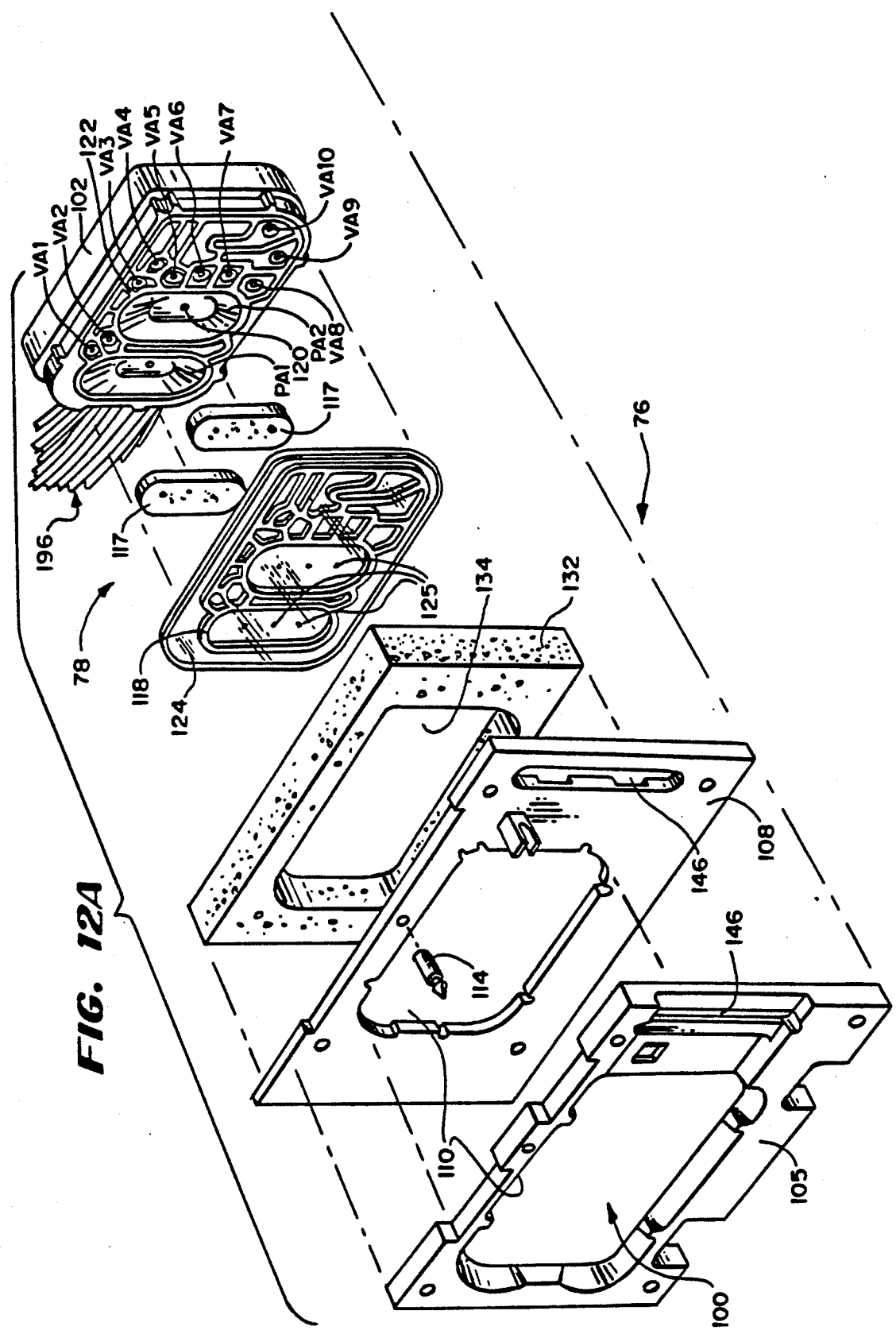
FIGS. 12A and 12B are exploded views of the cassette holder module shown in FIG. 11.

The cassette holder 100, which forms a part of the pneumatic actuator module 76, includes a front plate 105 joined to a back plate 108 (see FIG. 12A). The plates 105/108 collectively form an interior recess 110.

A door 106 is hinged to the front plate 155 (see FIGS. 6 and 7). The door 106 moves between an opened position (shown in FIGS. 6 and 7) and a closed position (shown in FIGS. 1; 2; and 11).

A door latch 115 operated by a latch handle 111 contacts a latch pin 114 when the door 106 is closed. Moving the latch handle 111 downward when the door 106 is closed engages the latch 115 to the pin 114 to lock the door 106 (as FIGS. 4 and 5 show). Moving the latch handle 111 upward when the door 106 is closed releases the latch 115 from the pin 114. This allows the door 106 to be opened (as FIG. 6 shows) to gain access to the holder interior.

With the door 106 opened, the user can insert the cassette 24 into the recess 110 with its front side 58 facing the interior of the cycler 14 (as FIGS. 6 and 7 show).

The inside of the door 106 carries an upraised elastomeric gasket 112 positioned in opposition to the recess 110. Closing the door 106 brings the gasket 112 into facing contact with the diaphragm 61 on the back side 60 of the cassette 24.

The pneumatic actuator module 76 contains a pneumatic piston head assembly 78 located behind the back plate 108 (see FIG. 12A).

The piston head assembly 78 includes a piston element 102. As FIGS. 12A; 13 and 14 show, the piston element 102 comprises a molded or machined plastic or metal body. The body contains two pump actuators PA1 and PA2 and ten valve actuators VA1 to VA10. The pump actuators PA1/PA2 and the valve actuators VA1 to VA10 are mutually oriented to form a mirror image of the pump stations P1/P2 and valve stations V1 to V10 on the front side 58 of the cassette 24.

Each actuator PA1/PA2/VA1 to VA10 includes a port 120. The ports 120 convey positive or negative pneumatic pressures from the pneumatic pressure distribution module 88 (as will be described in greater detail later).

Figure 13:
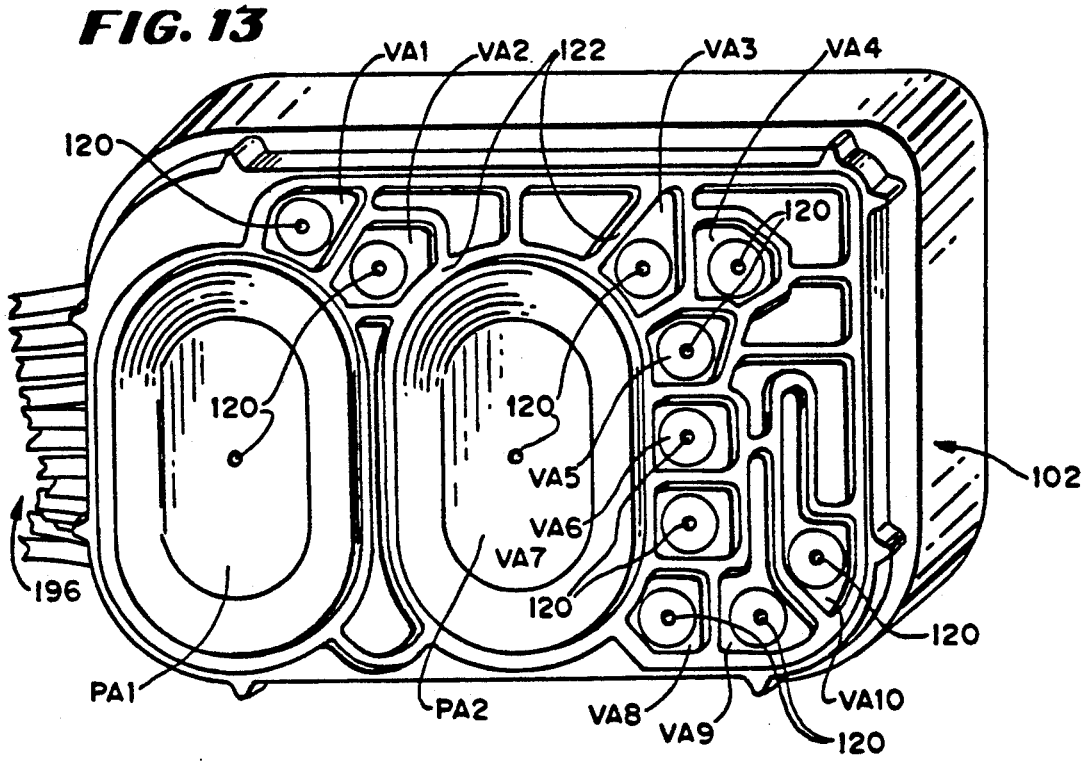
FIG. 13 is a perspective view of the operative front side of the fluid pressure piston housed within the cassette module shown in FIG. 11.

As FIG. 13 best shows, interior grooves 122 formed in the piston element 102 surround the pump and valve actuators PA1/PA2/VA1 to VA10. A preformed gasket 118 (see FIG. 12A) fits into these grooves 122. The gasket 118 seals the peripheries of the actuators PA1/PA2/VA1 to VA10 against pneumatic pressure leaks.

The configuration of the preformed gasket 118 follows the pattern of upstanding edges that peripherally surround and separate the pump chambers P1 and P2 and valve stations V1 to V10 on the front side 58 of the cassette 24.

Figure 12B:
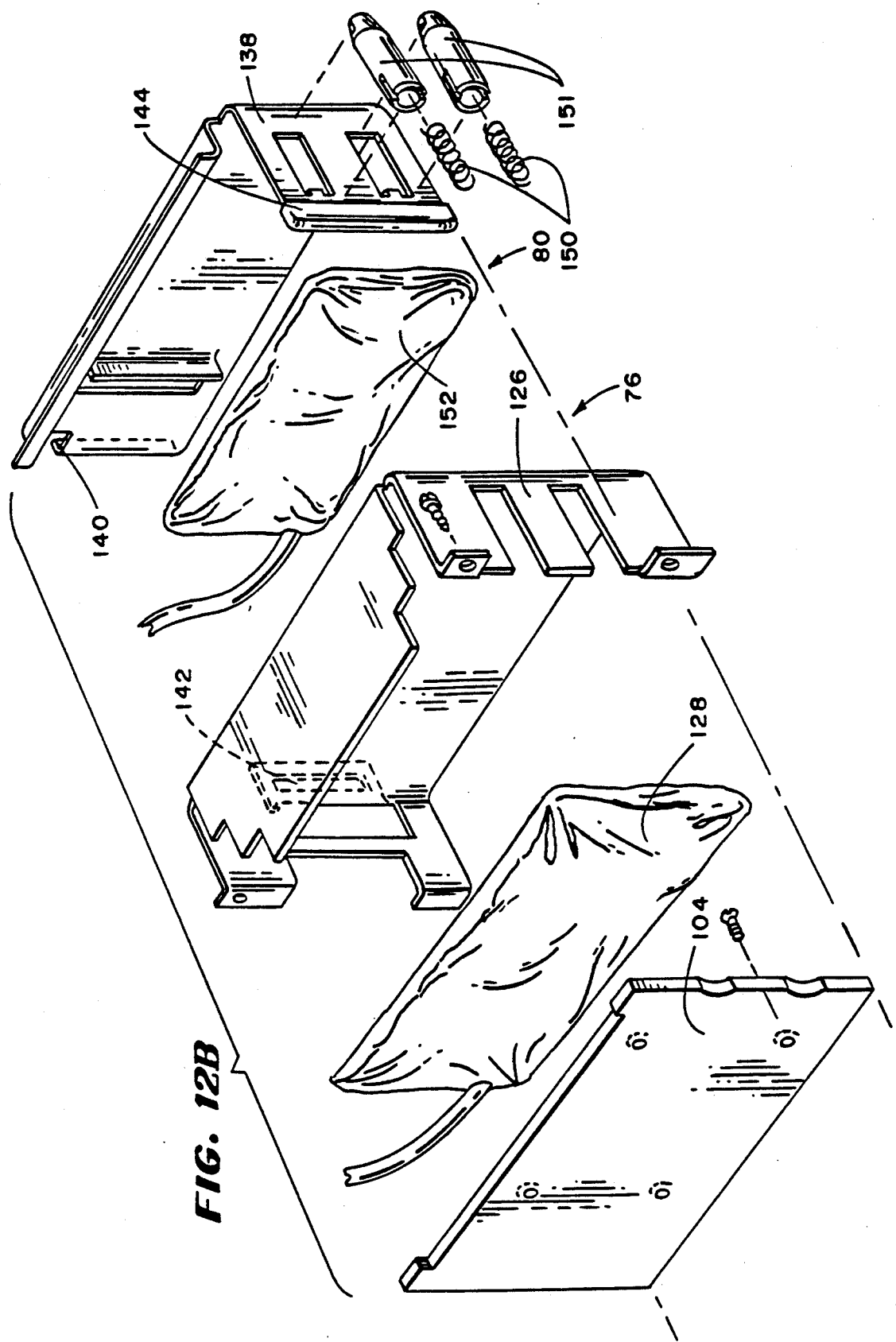

The piston element 102 is attached to a pressure plate 104 within the module 76 (see FIG. 12B). The pressure plate 104 is, in turn, supported on a frame 126 for movement within the module 76.

The side of the plate 104 that carries the piston element 102 abuts against a resilient spring element 132 in the module 76. In the illustrated and preferred embodiment, the spring element 132 is made of an open pore foam material.

The frame 126 also supports an inflatable main bladder 128. The inflatable bladder 128 contacts the other side of the plate 104.

The piston element 102 extends through a window 134 in the spring element 132 (see FIG. 12A). The window 134 registers with the cassette receiving recess 110.

With a cassette 24 fitted into the recess 110 and the holder door 106 closed, the piston element 102 in the window 134 is mutually aligned with the diaphragm 59 of the cassette 24 in the holder recess 110.

Figure 15A:
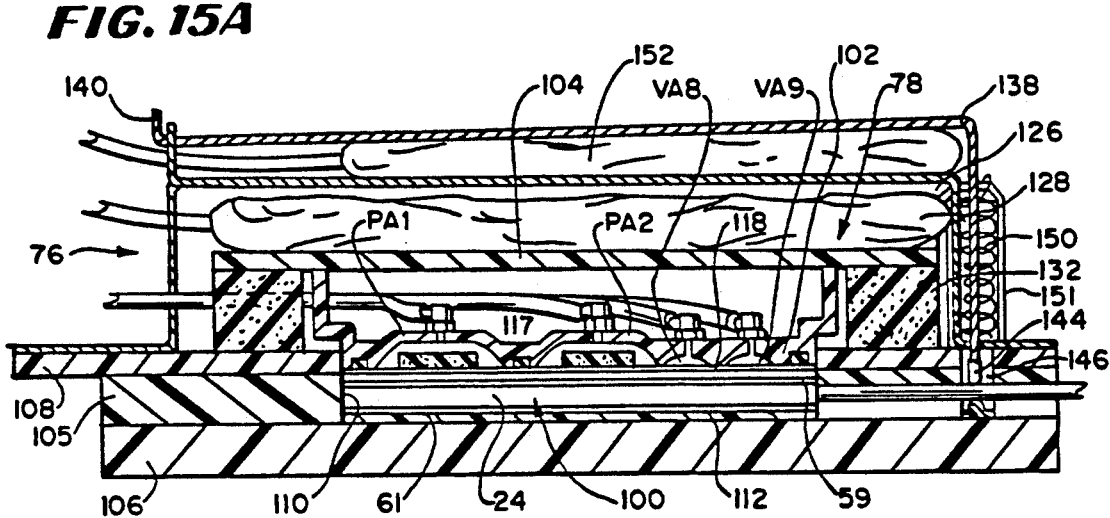
FIGS. 15A and 15B are top sectional views taken generally along line 15A—15A in FIG. 11, showing the interaction between the pressure plate assembly and the fluid pressure piston within the module shown in FIG. 11, with FIG. 15A showing the pressure plate holding the piston in an at rest position and FIG. 15B showing the pressure plate holding the piston in an operative position against the cassette.

As FIG. 15A shows, when the main bladder 128 is relaxed (i.e., not inflated), the spring element 132 contacts the plate 104 to hold the piston element 102 away from pressure contact with a cassette 24 within the holder recess 110.

As will be described in greater detail later, the pneumatic pressure distribution module 88 can supply positive pneumatic pressure to the main bladder 128. This inflates the bladder 128.

Figure 15B:
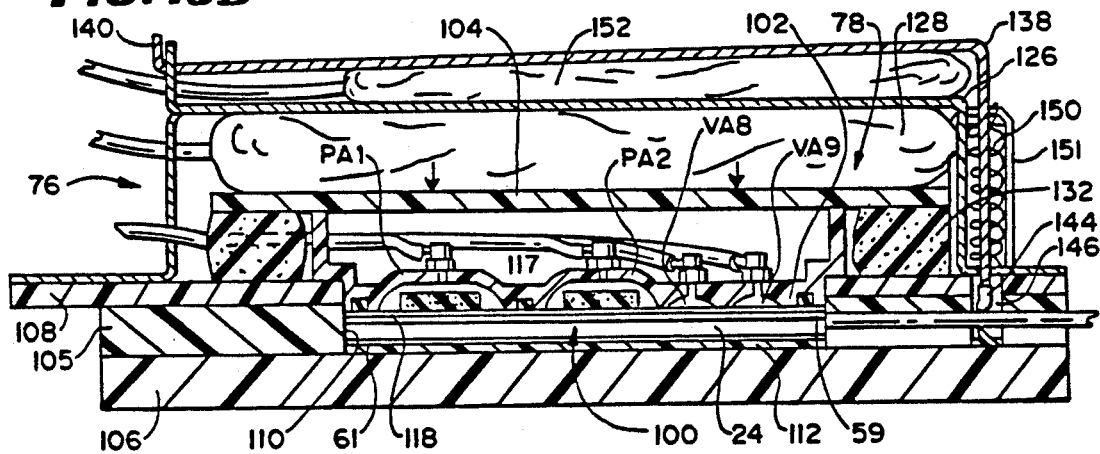

As FIG. 15B shows, when the main bladder 128 inflates, it presses the plate 104 against the spring element 132. The open cell structure of the spring element 132 resiliently deforms under the pressure. The piston element 102 moves within the window 134 into pressure contact against the cassette diaphragm 59.

The bladder pressure presses the piston element gasket 118 tightly against the cassette diaphragm 59. The bladder pressure also presses the back side diaphragm 61 tightly against the interior of the door gasket 112.

As a result, the diaphragms 59 and 61 seat against the upstanding peripheral edges 62 that surround the cassette pump chambers P1/P2 and valve stations V1 to V10. The pressure applied to the plate 104 by the bladder 128 seals the peripheries of these regions of the cassette 24.

The piston element 102 remains in this operating position as long as the main bladder 128 retains positive pressure and the door 106 remains closed.

In this position, the two pump actuators PA1 and PA2 in the piston element 102 register with the two pump chambers P1 and P2 in the cassette 24. The ten valve actuators VA1 to VA10 in the piston element 102 likewise register with the ten valve stations V1 to V10 in the cassette 24.

As will be described in greater detail later, the pneumatic pressure distribution module 88 conveys positive and negative pneumatic fluid pressure to the actuators PA1/PA2/VA1 to VA10 in a sequence governed by the controller 16. These positive and negative pressure pulses flex the diaphragm 59 to operate the pump chambers P1/P2 and valve stations V1 to V10 in the cassette 24. This, in turn, moves liquid through the cassette 24.

Venting the positive pressure in the bladder 128 relieves the pressure the plate 104 applies to the cassette 24. The resilient spring element 132 urges the plate 104 and attached piston element 102 away from pressure contact with the cassette diaphragm 59. In this position, the door 106 can be opened to unload the cassette 24 after use.

As FIG. 12A shows, the gasket 118 preferably includes an integral elastomeric membrane 124 stretched across it. This membrane 124 is exposed in the window 134. It serves as the interface between the piston element 102 and the diaphragm 59 of the cassette 24, when fitted into the holder recess 110.

The membrane 124 includes one or more small through holes 125 in each region overlying the pump and valve actuators PA1/PA2/VA1 to VA10. The holes 125 are sized to convey pneumatic fluid pressure from the piston element actuators to the cassette diaphragm 59. Nevertheless, the holes 125 are small enough to retard the passage of liquid. This forms a flexible splash guard across the exposed face of the gasket 118.

The splash guard membrane 124 keeps liquid out of the pump and valve actuators PA1/PA2/VA1 to VA10, should the cassette diaphragm 59 leak. The splash guard membrane 124 also serves as a filter to keep particulate matter out of the pump and valve actuators of the piston element 102. The splash guard membrane 124 can be periodically wiped clean when cassettes are exchanged.

As FIG. 12A shows, inserts 117 preferably occupy the pump actuators PA1 and PA2 behind the membrane 124.

In the illustrated and preferred embodiment, the inserts 117 are made of an open cell foam material. The inserts 117 help dampen and direct the pneumatic pressure upon the membrane 124. The presence of inserts 117 stabilizes air pressure more quickly within the pump actuators PA1 and PA2, helping to negate transient thermal effects that arise during the conveyance of pneumatic pressure.

(C) The Liquid Shutoff Assembly

The liquid shutoff assembly 80, which forms a part of the pneumatic actuator module 76, serves to block all liquid flow through the cassette 24 in the event of a power failure or another designated error condition.

As FIG. 12B shows, the liquid shutoff assembly 80 includes a movable occluder body 138 located behind the pressure plate frame 126. The occluder body 138 has a side hook element 140 that fits into a slot 142 in the pressure plate frame 126 (see FIGS. 16A/B). This hook-in-slot fit establishes a contact point about which the occluder body 138 pivots on the pressure plate frame 126.

The occluder body 138 includes an elongated occluder blade 144 (see FIGS. 12A; 15; and 16). The occluder blade 144 extends through a slot 146 in the front and back plates 105/108 of the holder 100. When the holder door 106 is closed, the blade 144 faces an elongated occluder bar 148 carried on the holder door 106 (see FIGS. 15 and 16).

When the cassette 24 occupies the holder recess 110 (see FIG. 7) and the holder door 106 is closed, all tubing 26 to 34 attached to the cassette 24 passes between the occluder blade 144 and the occluder bar 148 (a FIGS. 15 and 16 show).

In the illustrated and preferred embodiment, a region 145 of the flexible tubing 26 to 34 is held in a mutually close relationship near the cassette 24 (see FIG. 3). This bundled tubing region 145 further simplifies the handling of the cassette 24. This bundled region 145 also arranges the cassette tubing 26 to 34 in a close, side by side relationship in the region between the occluder blade 144 and bar 148 (see FIG. 7).

In the illustrated and preferred embodiment, the sidewalls of the flexible tubing 26 to 34 are RF surface welded together to form the bundled region 145.

Figure 16A:
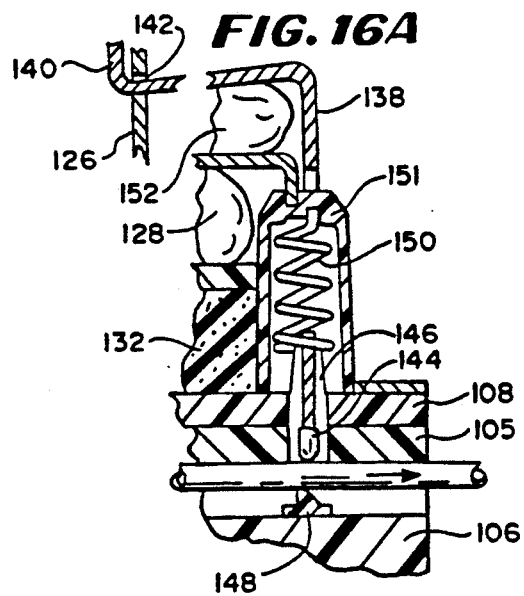
FIGS. 16A and 16B are side sectional view of the operation of the occluder assembly housed within the module shown in FIG. 11, with FIG. 16A showing the occluder assembly in a position allowing liquid flow and FIG. 16B showing the occluder assembly in a position blocking liquid flow.
Figure 16B:
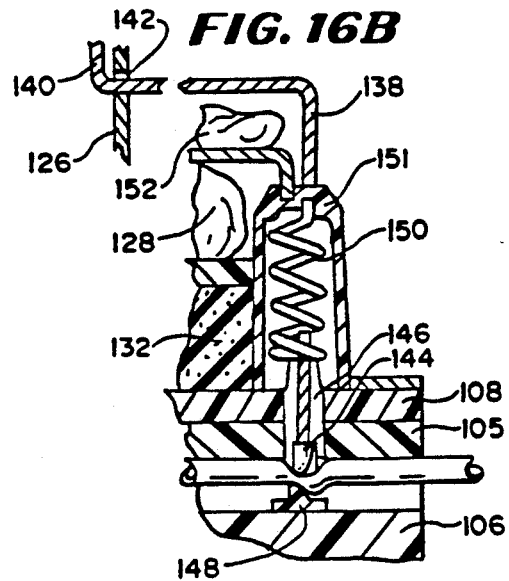

Pivotal movement of the occluder body 138 moves the occluder blade 144 toward or away from the occluder bar 148. When spaced apart (as FIG. 16A shows), the occluder blade and bar 144/148 allow clear passage of the cassette tubing 26 to 34. When brought together (as FIG. 16B shows), the occluder blade and bar 144/148 crimp the cassette tubing 26 to 34 closed. Occluder springs 150 carried within sleeves 151 normally bias the occluder blade and bar 144/148 together.

An occluder bladder 152 occupies the space between the occluder body 138 and the frame 126 (see FIG. 12B).

As FIG. 16B shows, when the occluder bladder 152 is relaxed (i.e., not inflated), it makes no contact against the occluder body 138. The occluder springs 150 urge the occluder blade and bar 144/148 together, simultaneously crimping all cassette tubing 26 to 34 closed. This prevents all liquid flow to and from the cassette 24.

As will be described in greater detail later, the pneumatic pressure distribution module 88 can supply positive pneumatic pressure to the occluder bladder 152. This inflates the bladder 128.

As FIG. 16A shows, when the occluder bladder 152 inflates, it presses against the occluder body 138 to pivot it upward. This moves the occluder blade 144 away from the occluder bar 158. This permits liquid to flow through all tubing to and from the cassette 24.

The occluder blade and bar 144/148 remain spaced apart as long as the occluder bladder 152 retains positive pressure.

Venting of positive pressure relaxes the occluder bladder 152. The occluder springs 150 immediately urge the occluder blade and bar 144/148 back together to crimp the tubing closed.

As will be described in greater detail later, an electrically actuated valve C6 communicates with the occluder bladder 152. When receiving electrical power, the valve C6 is normally closed. In the event of a power loss, the valve C6 opens to vent the occluder bladder 152, crimping the cassette tubing 26 to 34 closed.

The assembly 80 provides a pneumatically actuated fail-safe liquid shut off for the pneumatic pumping system.

(D) The Pneumatic Pressure Source

The pneumatic pressure source 84 comprises a linear vacuum pump and air compressor capable of generating both negative and positive air pressure. In the illustrated and preferred embodiment, the pump 84 is a conventional air compressor/vacuum pump commercially available from Medo Corporation.

Figure 23:
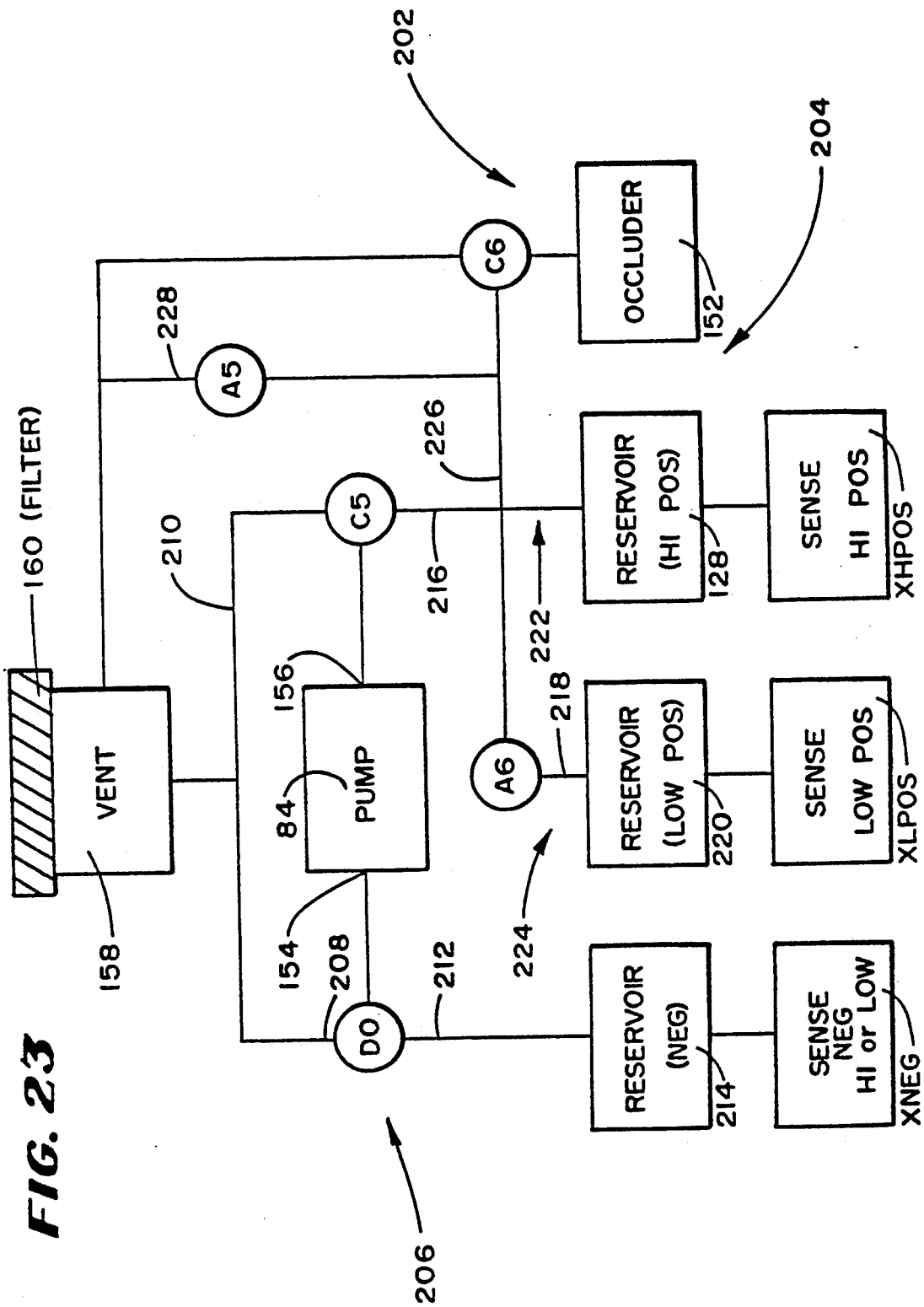
FIG. 23 is a schematic view of the pressure supply system associated with the air regulation system that the manifold assembly shown in FIG. 19 defines.

As FIG. 23 shows, the pump 84 includes an inlet 154 for drawing air into the pump 84. The pump inlet 154 supplies the negative pressure required to operate the cycler 14.

As FIG. 23 also shows, the pump 14 also includes an outlet 156 for discharging air from the pump 84. The pump outlet 156 supplies positive pressure required to operate the cycler 14.

FIGS. 9 and 10 also show the inlet 154 and outlet 156.

The pump inlet 154 and the pump outlet 156 communicate with ambient air via a common vent 158 (shown schematically in FIG. 23). The vent 158 includes a filter 160 that removes particulates from the air drawn into the pump 84.

(E) The Pressure Distribution System

FIGS. 17 to 22 show the details of the pneumatic pressure distribution module 88. The module 88 encloses a manifold assembly 162. The manifold assembly 162 controls the distribution of positive and negative pressures from the pump 84 to the piston element 102, the main bladder 128, and the occluder bladder 152. The controller 16 provides the command signals that govern the operation of the manifold assembly 162.

Figure 18:
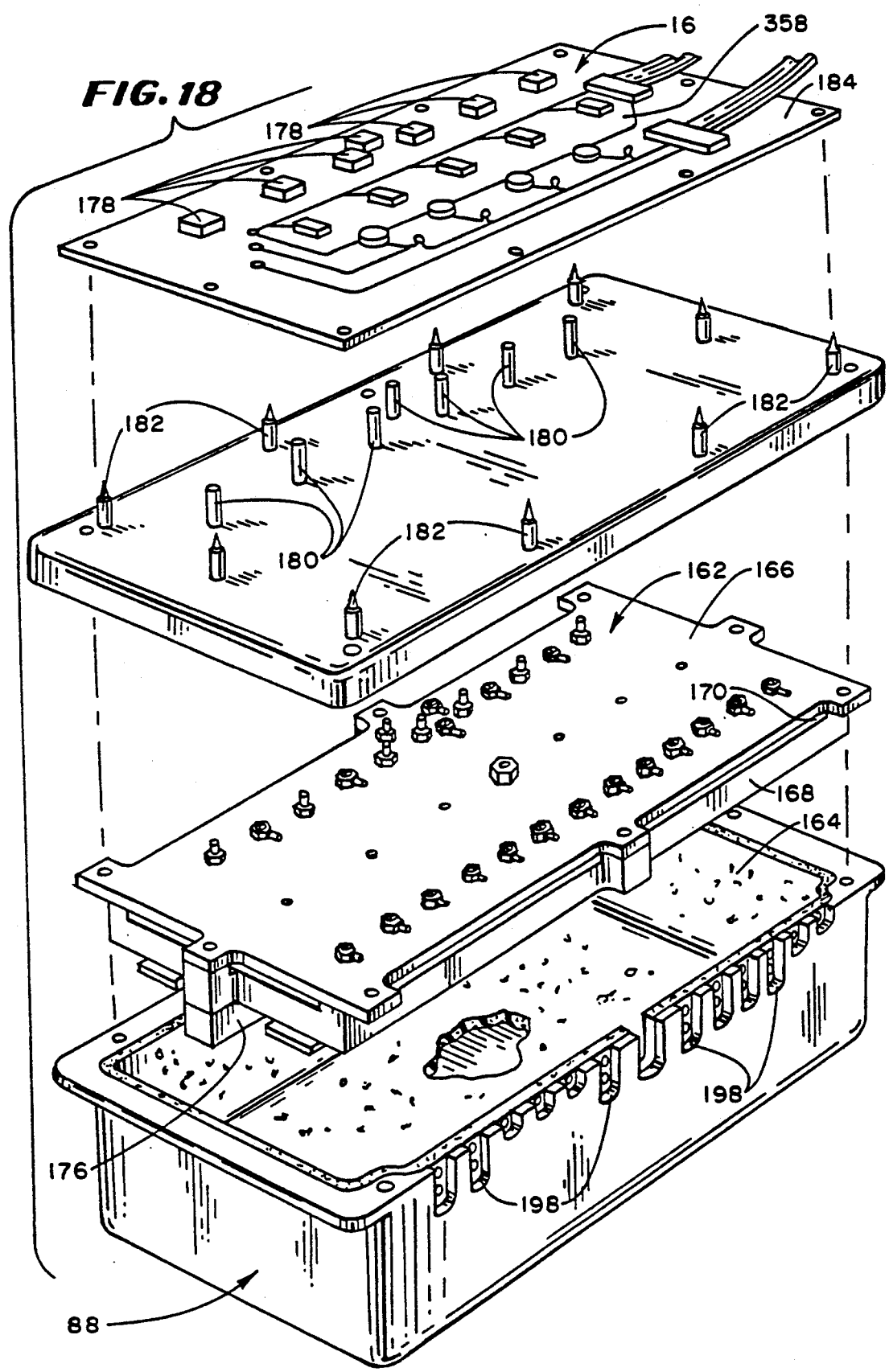
FIG. 18 is an exploded perspective view of interior of the fluid pressure manifold module shown in FIG. 17.

As FIGS. 18 shows, a foam material 164 preferably lines the interior of the module 88 enclosing the manifold assembly 162. The foam material 164 provides a barrier to dampen sound to assures quiet operation.

Figure 19:
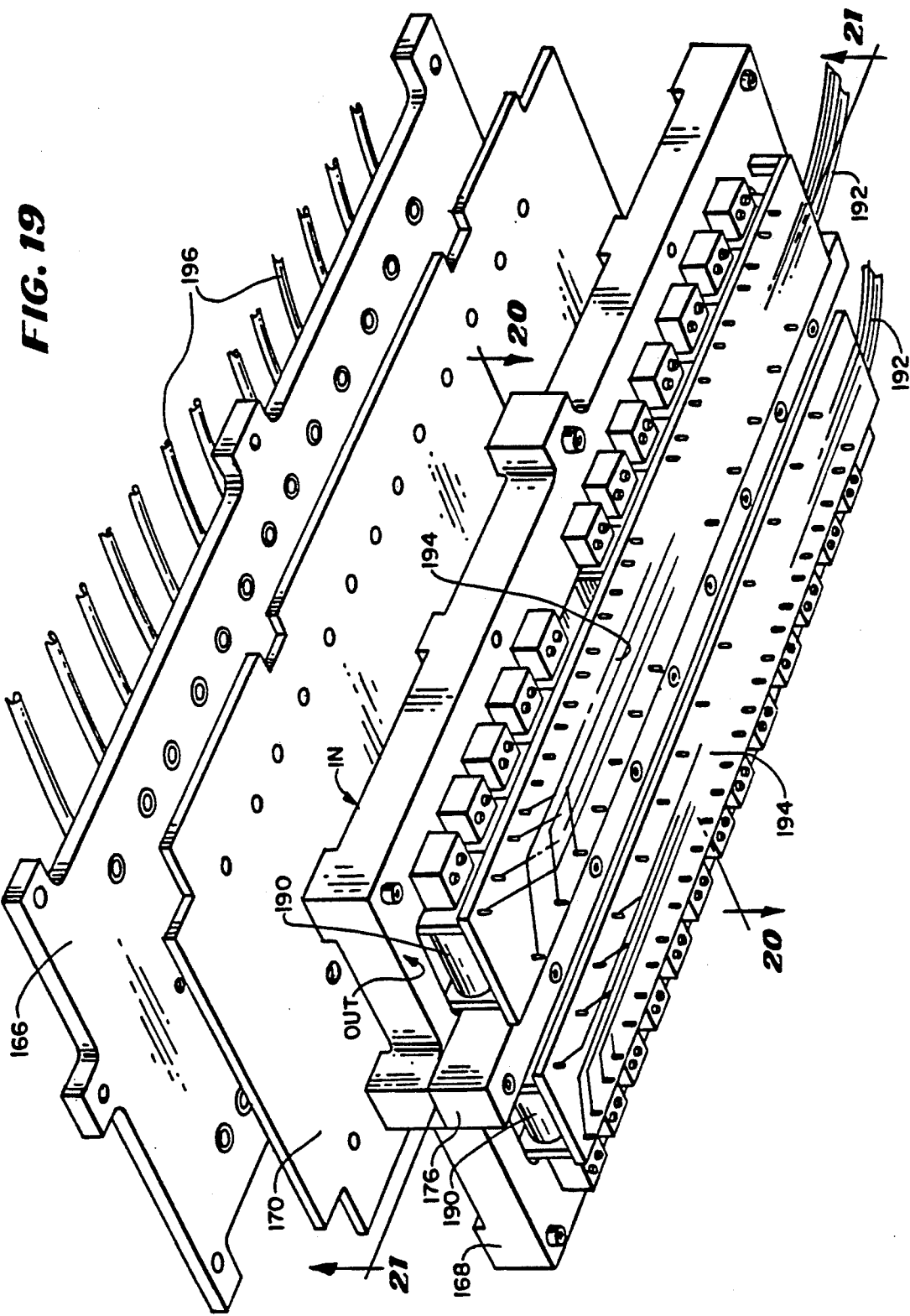
FIG. 19 is an exploded perspective view of the manifold assembly housed within the module shown in FIG. 18.

As FIGS. 18 and 19 show, the manifold assembly 162 includes a top plate 166 and a bottom plate 168. A sealing gasket 170 is sandwiched between the plates 166/168.

Figure 20:
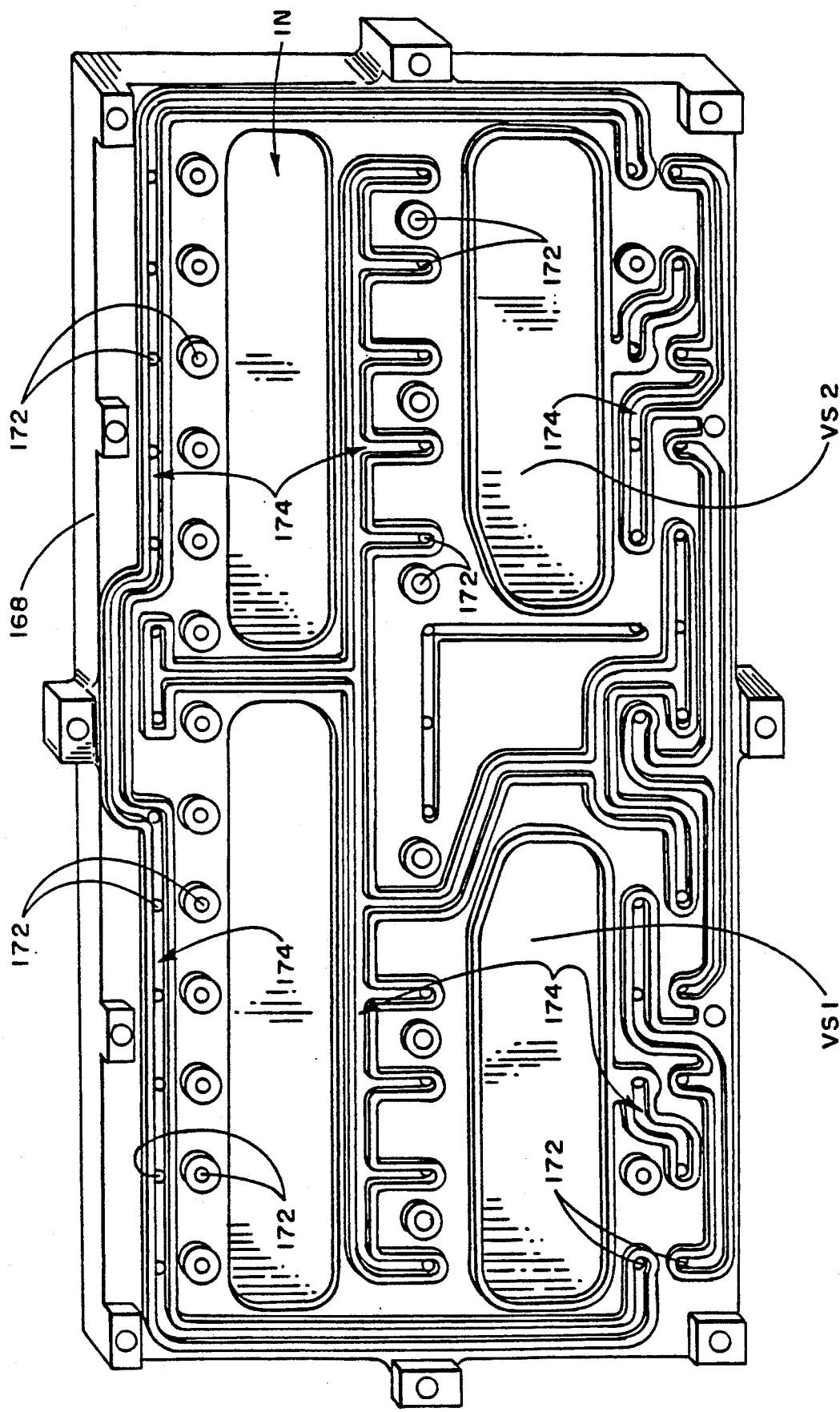
FIG. 20 is a plan view of the interior of the base plate of the manifold assembly shown in FIG. 19, showing the paired air ports and air conduction pathways formed therein.
Figure 21:
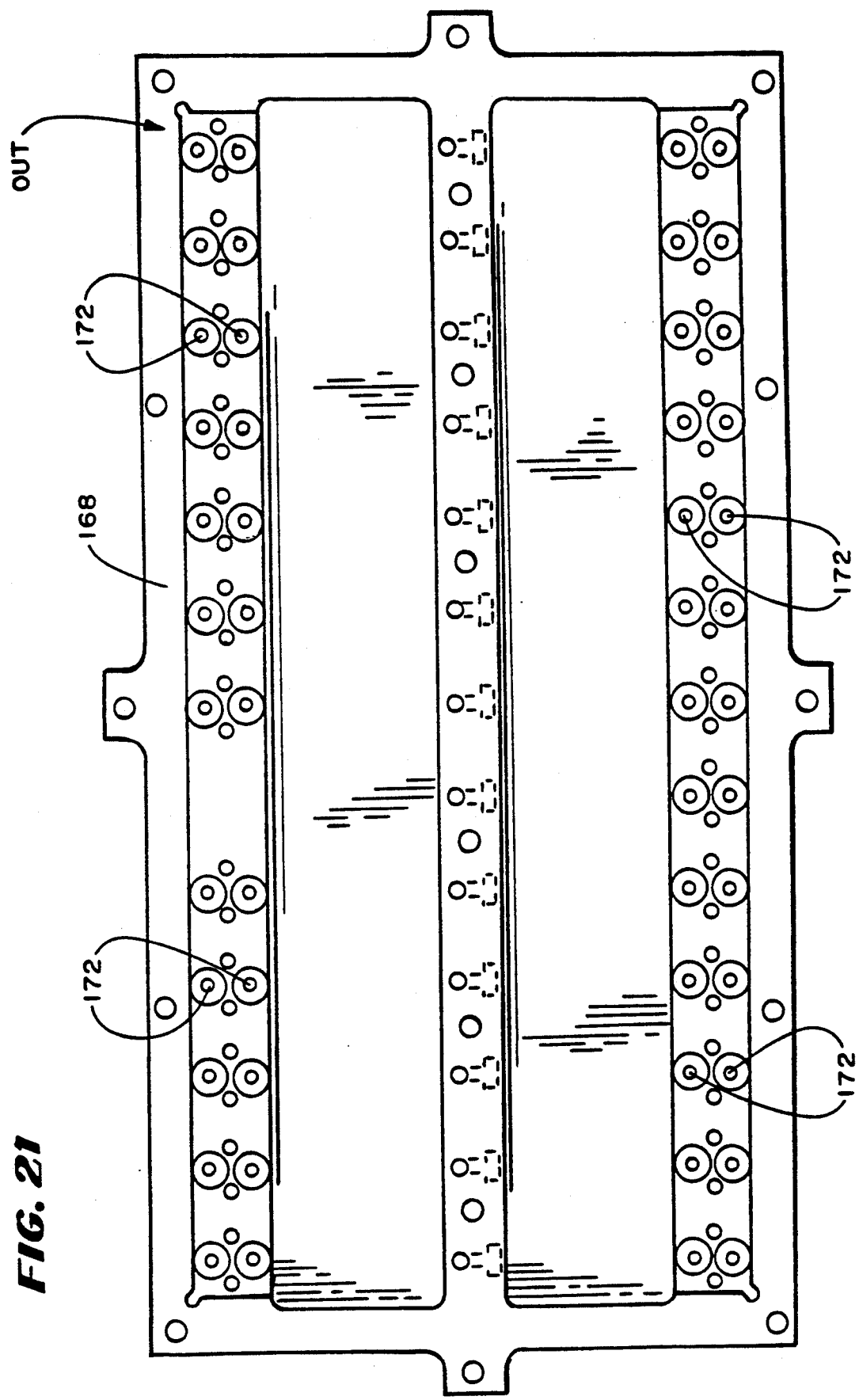
FIG. 21 is a plan view of the outside of the base plate of the manifold assembly shown in FIG. 19, also showing the paired air ports.

The bottom plate 168 (see FIGS. 20 and 21) includes an array of paired air ports 172. FIG. 20 shows the inside surface of the bottom plate 168 that faces the gasket 170 (which is designated IN in FIGS. 19 and 20). FIG. 21 shows the outside surface of the bottom plate 168 (which is designated OUT in FIGS. 19 and 21).

The inside surface (IN) of the bottom plate 168 also contains an array of interior grooves that form air conduction channels 174 (see FIG. 20). The array of paired air ports 172 communicates with the channels 174 at spaced intervals. A block 176 fastened to the outside surface (OUT) of the bottom plate 168 contains an additional air conduction channels 174 that communicate with the channels 174 on the inside plate surface (IN) (see FIGS. 19 and 22).

Transducers 178 mounted on the exterior of the module 88 sense through associated sensing tubes 180 (see FIG. 18) pneumatic pressure conditions present at various points along the air conduction channels 174. The transducers 178 are conventional semi-conductor piezoresistance pressure sensors. The top of the module 88 includes stand-off pins 182 that carry a board 184 to which the pressure transducers 178 are attached.

The outside surface (OUT) of the bottom plate 168 (see FIGS. 19 and 22) carries a solenoid actuated pneumatic valves 190 connected in communication with each pair of air ports 172. In the illustrated embodiment, there are two rows of valves 190 arranged along opposite sides of the outside surface (OUT) of the plate 168. Twelve valves 190 form one row, and thirteen valves 190 form the other row.

Figure 22:
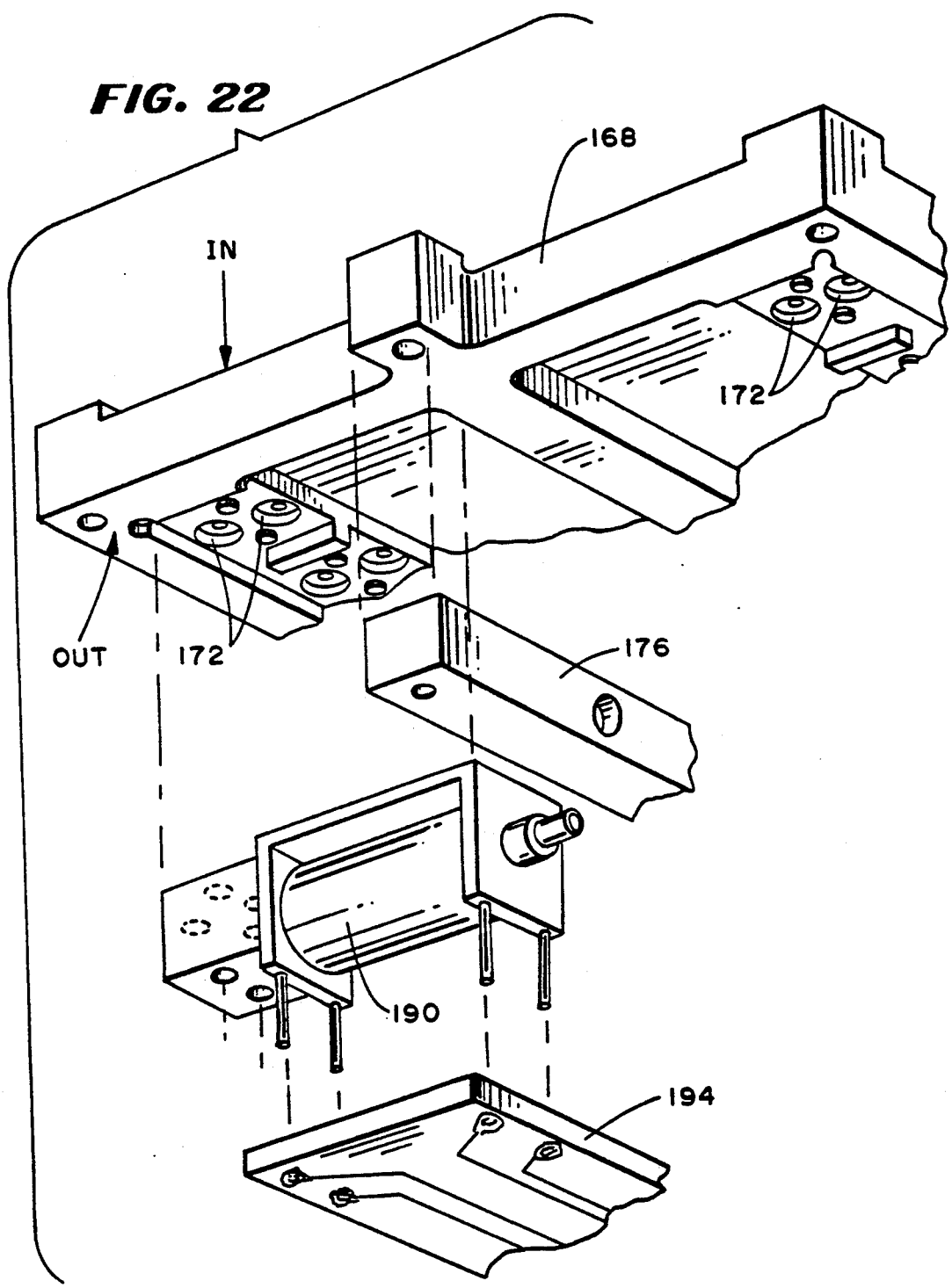
FIG. 22 is an exploded perspective view of the attachment of a pneumatic valve on the outside of the base plate of the manifold assembly shown in FIG. 19, in registry over a pair of air ports.

As FIG. 22 shows, each pneumatic valve 190 is attached in communication with a pair of air ports 172 by screws fastened to the outside surface (OUT) of the bottom plate 168. As FIGS. 19 and 22 also show, each valve 190 is electrically connected by ribbon cables 192 to the cycler controller 16 by contacts on a junction board 194. There are two junction boards 194, one for each row of valves 190.

Each pneumatic valve 190 operates to control air flow through its associated pair of ports 172 to link the ports 172 to the various air channels 174 the bottom plate 168 carries. As will be described in greater detail later, some of the valves 190 are conventional three way valves. Others are conventional normally closed two way valves.

The air channels 174 within the manifold assembly 162 are coupled by flexible tubing 196 (see FIG. 17) to the system components that operate using pneumatic pressure. Slots 198 in the side of the module 88 accommodate the passage of the tubing 196 connected to the manifold assembly 162.

FIGS. 9 and 10 also show the flexible tubing 196 that links the manifold assembly 162 to the pneumatically actuated and controlled system components.

Figure 11:
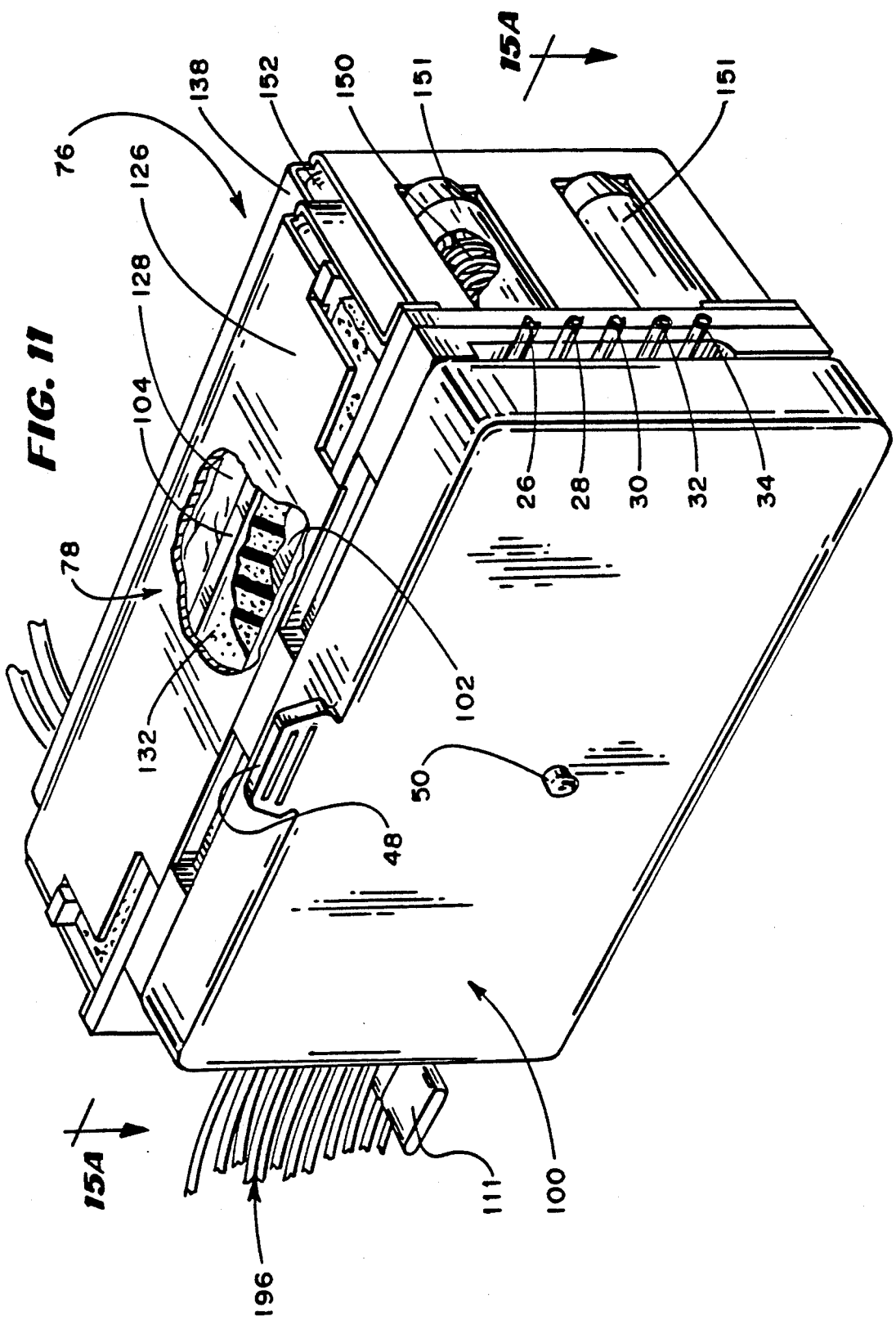
FIG. 11 is an enlarged perspective view of the cassette holder module housed within the cycler.
Figure 14A:
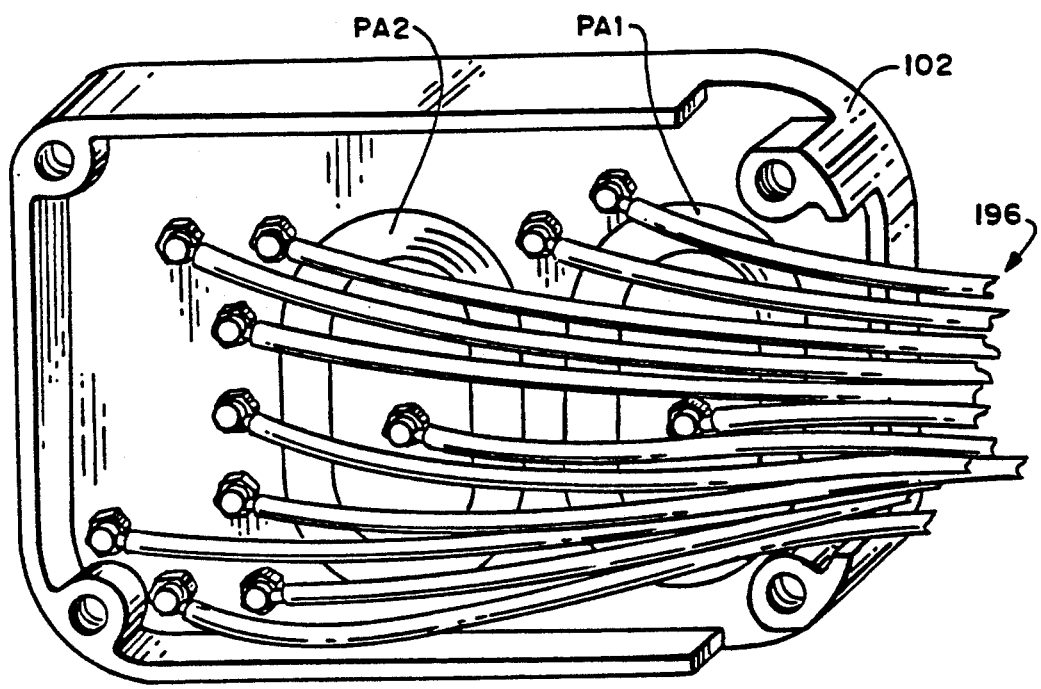
FIG. 14A is a perspective view of the back side of the fluid pressure piston shown in FIG. 13.

FIG. 11 further shows the tubing 196 from the manifold assembly 162 entering the pneumatic actuator module 76, where they connect to the main bladder 128, the occluder bladder 152, and the piston element 102. FIG. 14A further shows the T-fittings that connect the tubing 196 to the ports of the valve actuators VA1 to VA10 and the ports of the pump actuators PA1/PA2 of the piston element 102. These connections are made on the back side of the piston element 102.

1. The Pressure Regulation System

Figure 24:
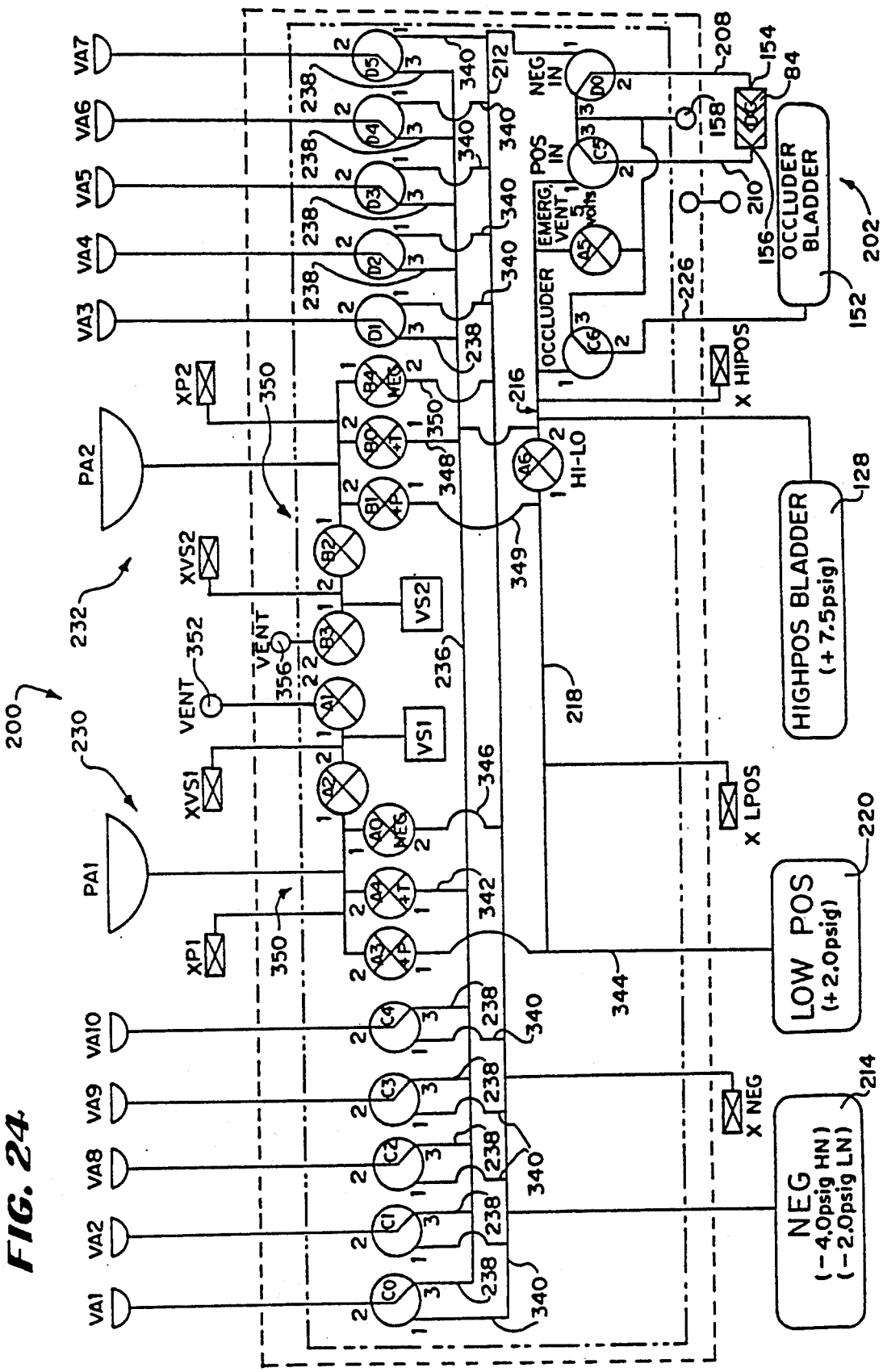
FIG. 24 is a schematic view of the entire air regulation system that the manifold assembly shown in FIG. 19 defines.

The air conduction passages 174 and the flexible tubing 196 associated with the manifold assembly 162 define a fluid pressure regulation system 200 that operates in response to command signals from the cycler controller 16. FIGS. 23 and 24 show the details of the air regulation system 200 in schematic form.

In response to the command signals of the controller 16, the pressure regulation system 200 directs the flow of positive and negative pneumatic pressures to operate the cycler 14. When power is applied, the system 200 maintains the occluder assembly 80 in an open, flow-permitting condition; it seals the cassette 24 within the holder 100 for operation; and it conveys pneumatic pressure to the piston element 102 to move liquid through the cassette 24 to conduct an APD procedure. The pressure regulation system 200 also provides information that the controller 16 processes to measure the volume of liquid conveyed by the cassette 24.

a. Pressure Supply Network

As FIG. 23 shows, the regulation system 200 includes a pressure supply network 202 having a positive pressure side 204 and a negative pressure side 206. The positive and negative pressure sides 204 and 206 can each be selectively operated in either a low-relative pressure mode or high-relative pressure mode.

The controller 16 calls for a low-relative pressure mode when the cycler 14 circulates liquid directly through the patient's indwelling catheter 18 (i.e., during patient infusion and drain phases). The controller 16 calls for a high-relative pressure mode when the cycler 14 circulates liquid outside the patient's indwelling catheter 18 (i.e. during transfers of liquid from supply bags 20 to the heater bag 22).

In other words, the controller 16 activates the low-relative pressure mode when considerations of patient comfort and safety predominate. The controller 16 activates the high-relative pressure mode when considerations of processing speed predominate.

In either mode, the pump 84 draws air under negative pressure from the vent 158 through an inlet line 208. The pump 84 expels air under positive pressure through an outlet line 210 to the vent 158.

The negative pressure supply side 206 communicates with the pump inlet line 208 through a negative pressure branch line 212. The three way pneumatic valve D0 carried on the manifold assembly 162 controls this communication.

The branch line 212 supplies negative pressure to a reservoir 214 carried within the cycler housing 82 (this can be seen in FIGS. 9 and 10). The reservoir 214 preferably has a capacity greater than about 325 cc and a collapse pressure of greater than about −10 psig. The transducer XNEG carried on the manifold assembly 162 senses the amount of negative pressure stored within the negative pressure reservoir 214.

When in the high-relative negative pressure mode, the transducer XNEG transmits a control signal when the predefined high-relative negative pressure of −5.0 psig is sensed. When in the low-relative negative pressure mode, the transducer XNEG transmits a control signal when the predefined low-relative negative pressure of −1.2 psig is sensed. The pressure reservoir 214 serves as both a low-relative and a high-relative pressure reservoir, depending upon the operating mode of the cycler 14.

The positive pressure supply side 204 communicates with the pump outlet line 210 through a main positive pressure branch line 216. The three way pneumatic valve C5 controls this communication.

The main branch line 216 supplies positive pressure to the main bladder 128, which seats the piston head 116 against the cassette 24 within the holder 100. The main bladder 128 also serves the system 202 as a positive high pressure reservoir.

The main bladder 128 preferably has a capacity of greater than about 600 cc and a fixtured burst pressure over about 15 psig.

Transducer XHPOS carried on the manifold assembly 162 senses the amount of positive pressure within the main bladder 128. Transducer XHPOS transmits a control signal when the predetermined high-relative pressure of 7.5 psig is sensed.

A first auxiliary branch line 218 leads from the main branch line 216 to a second positive pressure reservoir 220 carried within the housing 82 (which can also be seen in FIGS. 9 and 10). The two way, normally closed pneumatic valve A6 carried by the manifold assembly 168 controls the passage of positive pressure to the second reservoir 220. The second reservoir 220 serves the system 202 as a reservoir for low-relative positive pressure.

The second reservoir 220 preferably has a capacity of greater than about 325 cc and a fixtured burst pressure greater than about 10 psig.

Transducer XLPOS carried on the manifold assembly 162 senses the amount of positive pressure within the second pressure reservoir 220. Transducer XLPOS is set to transmit a control signal when the predetermined low-relative pressure of 2.0 psig is sensed.

The valve A6 divides the positive pressure supply side 204 into a high-relative positive pressure region 222 (between valve station C5 and valve station A6) and a low-relative positive pressure region 224 (between valve station A6 and the second reservoir 220).

A second auxiliary positive pressure branch line 226 leads from the main branch line 216 to the occluder bladder 152 through three way pneumatic valve C6. The occluder bladder 152 also serves the system 202 as a positive high pressure reservoir.

A bypass branch line 228 leads from the main branch 216 to the vent 158 through the two way, normally closed valve A5. The valve C6 also communicates with the bypass branch line 228.

The pressure supply network 202 has three modes of operation. In the first mode, the network 202 supplies the negative pressure side 206. In the second mode, the network 202 supplies the positive pressure side 204. In the third mode, the network 202 supplies neither negative or positive pressure side 204/206, but serves to circulate air in a continuous manner through the vent 158.

With the three modes of operation, the pump 84 can be continuously operated, if desired. This avoids any time delays and noise occasioned by cycling the pump 84 on and off.

In the first mode, valve station D0 opens communication between the negative branch line 212 and the pump inlet line 208. Valve C5 opens communication between the pump outline line 210 and the vent 158, while blocking communication with the main positive branch line 216.

The pump 84 operates to circulate air from the vent 158 through its inlet and outlet lines 208/210 to the vent 158. This circulation also draws air to generating negative pressure in the negative branch line 212. The reservoir 214 stores this negative pressure.

When the transducer XNEG senses its predetermined high-relative or low-relative negative pressure, it supplies a command signal to operate valve D0, closing communication between the pump inlet line 208 and the negative branch line 212.

In the second mode, valve D0 closes communication between the negative branch line 212 and the pump inlet line 208. Valve C5 closes communication with the vent 158, while opening communication with the main positive branch line 216.

The pump 84 operates to convey air under positive pressure into the main positive branch line 216. This positive pressure accumulates in the main bladder 128 for conveyance to the pump and valve actuators on the piston element 102.

By operating three way valve C6, the positive pressure can also be directed to fill the occluder bladder 152. When the valve C6 is in this position, the positive pressure in the occluder bladder 152 also can be conveyed to the pump and valve actuators on the piston element 102

Otherwise, valve C6 directs the positive pressure through the bypass line 228 to the vent 158. In the absence of an electrical signal (for example, if there is a power failure), valve C6 opens the occluder bladder 152 to the bypass line 228 to the vent 158.

Valve A6 is either opened to convey air in the main branch line 216 to the low pressure reservoir 214 or closed to block this conveyance. The transducer XLPOS opens the valve A6 upon sensing a pressure below the low-relative cut-off. The transducer XLPOS closes the valve station A6 upon sensing pressure above the low-relative cut-off.

The transducer XHIPOS operates valve C5 to close communication between the pump outlet line 210 and the main positive branch line 216 upon sensing a pressure above the high-relative cut-off of 7.5 psig.

In the third mode, valve D0 closes communication between the negative branch line 212 and the pump inlet line 208. Valve C5 opens communication between the pump outlet line 210 and the vent 158, while blocking communication with the main positive branch line 216.

The pump 84 operates to circulate air in a loop from the vent 158 through its inlet and outlet lines 208/210 back to the vent 158.

b. The Pressure Actuating Network

As FIG. 24 shows, the regulation system also includes first and second pressure actuating networks 230 and 232.

The first pressure actuating network 230 distributes negative and positive pressures to the first pump actuator PA1 and the valve actuators that serve it (namely, VA1; VA2; VA8; VA9; and VA10). These actuators, in turn, operate cassette pump station P1 and valve stations V1; V2; V8; V9; and V10, respectively, which serve pump station P1.

The second pressure actuating network 232 distributes negative and positive pressures to the second pump actuator PA2 and the valve actuators that serve it (namely, VA3; VA4; VA5; VA6; and VA7). These actuators, in turn, operate cassette pump station P2 and cassette valve stations V3; V4; V5; V6; and V7, which serve pump station P2.

The controller 16 can operate the first and second actuating networks 230 and 232 in tandem to alternately fill and empty the pump chambers P1 and P2. This provides virtually continuous pumping action through the cassette 24 from the same source to the same destination.

Alternatively, the controller 16 can operate the first and second actuating networks 230 and 232 independently. In this way, the controller 16 can provide virtually simultaneous pumping action through the cassette 24 between different sources and different destinations.

This simultaneous pumping action can be conducted with either synchronous or non-synchronous pressure delivery by the two networks 230 and 232. The networks 230 and 232 can also be operated to provide pressure delivery that drifts into an out of synchronousness.

The first actuating network 230 provides high-relative positive pressure and negative pressures to the valve actuators VA1; VA2; VA8; VA9; and VA10

The first actuating network 230 also selectively provides either high-relative positive and negative pressure or low-relative positive and negative pressure to the first pumping actuator PA1.

Referring first to the valve actuators, three way valves C0; C1; C2; C3; and C4 in the manifold assembly 162 control the flow of high-relative positive pressure and negative pressures to the valve actuators VA1; VA2; VA8; VA9; and VA10.

The high-relative positive pressure region of the main branch line 216 communicates with the valves C0; C1: C2; C3; and C4 through a bridge line 234, a feeder line 236, and individual connecting lines 238.

The negative pressure branch 212 communicates with the valves C0; C1; C2; C3; and C4 through individual connecting lines 340. The controller 16 sets this branch 212 to a high-relative negative pressure condition by setting the transducer XNEG to sense a high-relative pressure cut-off.

By applying negative pressure to one or more given valve actuators, the associated cassette valve station is opened to accommodate liquid flow. By applying positive pressure to one or more given valve actuators, the associated cassette value station is closed to block liquid flow. In this way, the desired liquid path leading to and from the pump chamber P1 can be selected.

Referring now to the pump actuator PA1, two way valve A4 in the manifold assembly 162 communicates with the high-relative pressure feeder line 236 through connecting line 342. Two way valve A3 in the manifold assembly 162 communicates with the low-relative positive pressure reservoir through connecting line 344. By selectively operating either valve A4 or A3, either high-relative or low-relative positive pressure can be supplied to the pump actuator PA1.

Two way valve A0 communicates with the negative pressure branch 212 through connecting line 346. By setting the transducer XNEG to sense either a low-relative pressure cut-off or a high-relative pressure cut-off, either low-relative or high-relative pressure can be supplied to the pump actuator VA1 by operation of valve A0.

By applying negative pressure (through valve A0) to the pump actuator PA1, the cassette diaphragm 59 flexes out to draw liquid into the pump chamber P1. By applying positive pressure (through either valve A3 or A4) to the pump actuator PA1, the cassette diaphragm 59 flexes in to pump liquid from the pump chamber P1 (provided, of course, that the associated inlet and outlet valves are opened). By modulating the time period during which pressure is applied, the pumping force can be modulated between full strokes and partial strokes with respect to the pump chamber P1.

The second actuating network 232 operates like the fist actuating network 230, except it serves the second pump actuator PA2 and its associated valve actuators VA3; VA4; VA5; VA6; and VA7.

Like the first actuating network 230, the second actuating network 232 provides high-relative positive pressure and high-relative negative pressures to the valve actuators VA3; VA4; VA5; VA6; and VA7. Three way valves D1; D2: D3; D4; and D5 in the manifold assembly 162 control the flow of high-relative positive pressure and high-relative negative pressures to the valve actuators VA3; VA4; VA5; VA6; and VA7.

The high-relative positive pressure region 222 of the main branch line communicates with the valves D1; D2; D3; D4; and D5 through the bridge line 234, the feeder line 236, and connecting lines 238.

The negative pressure branch 212 communicates with the valves D1: D2; D3; D4; and D5 through connecting lines 340. This branch 212 can be set to a high-relative negative pressure condition by setting the transducer XNEG to sense a high-relative pressure cut-off.

Like the first actuating network 230, the second actuating network 232 selectively provides either high-relative positive and negative pressure or low-relative positive and negative pressure to the second pumping actuator PA2. Two way valve B0 in the manifold assembly 162 communicates with the high-relative pressure feeder line through connecting line 348. Two way valve station B1 in the manifold assembly 162 communicates with the low-relative positive pressure reservoir through connecting line 349. By selectively operating either valve B0 or B1, either high-relative or low-relative positive pressure can be supplied to the pump actuator PA2.

Two way valve B4 communicates with the negative pressure branch through connecting line 350. By setting the transducer XNEG to sense either a low-relative pressure cut-off or a high-relative pressure cut-off, either low-relative or high-relative pressure can be supplied to the pump actuator PA2 by operation of valve B4.

Like the first actuating network 230, by applying negative pressure to one or more given valve actuators, the associated cassette value station is opened to accommodate liquid flow. By applying positive pressure to one or more given valve actuators, the associated cassette value station is closed to block liquid flow. In this way, the desired liquid path leading to and from the pump chamber P2 can be selected.

By applying a negative pressure (through valve B4) to the pump actuator PA2, the cassette diaphragm flexes out to draw liquid into the pump chamber P2. By applying a positive pressure (through either valve BB0 or B1) to the pump actuator PA2, the cassette diaphragm flexes in to move liquid from the pump chamber P2 (provided, of course, that the associated inlet and outlet valves are opened). By modulating the time period during which pressure is applied, the pumping force can be modulated between full strokes and partial strokes with respect to the pump chamber P2.

The first and second actuating networks 230/232 can operate in succession, one drawing liquid into pump chamber P1 while the other pump chamber P2 pushes liquid out of pump chamber P2, or vice versa, to move liquid virtually continuously from the same source to the same destination.

The first and second actuating networks 230/232 can also operate to simultaneously move one liquid through pump chamber P1 while moving another liquid through pump chamber P2. The pump chambers P1 and P2 and serve the same or different destinations.

Furthermore, with additional reservoirs, the first and second actuation networks 232/232 can operate on the same or different relative pressure conditions. The pump chamber P1 can be operated with low-relative positive and negative pressure, while the other pump chamber P2 is operated with high-relative positive and negative pressure.

c. Liquid Volume Measurement

As FIG. 24 shows, the pressure regulating system 200 also includes a network 350 that works in conjunction with the controller 16 for measuring the liquid volumes pumped through the cassette.

The liquid volume measurement network 350 includes a reference chamber of known air volume ($V_s$) associated with each actuating network. Reference chamber VS1 is associated with the first actuating network. Reference chamber VS2 is associated with the second actuating network.

The reference chambers VS1 and VS2 may be incorporated at part of the manifold assembly 162, as FIG. 20 shows.

Figure 14B:
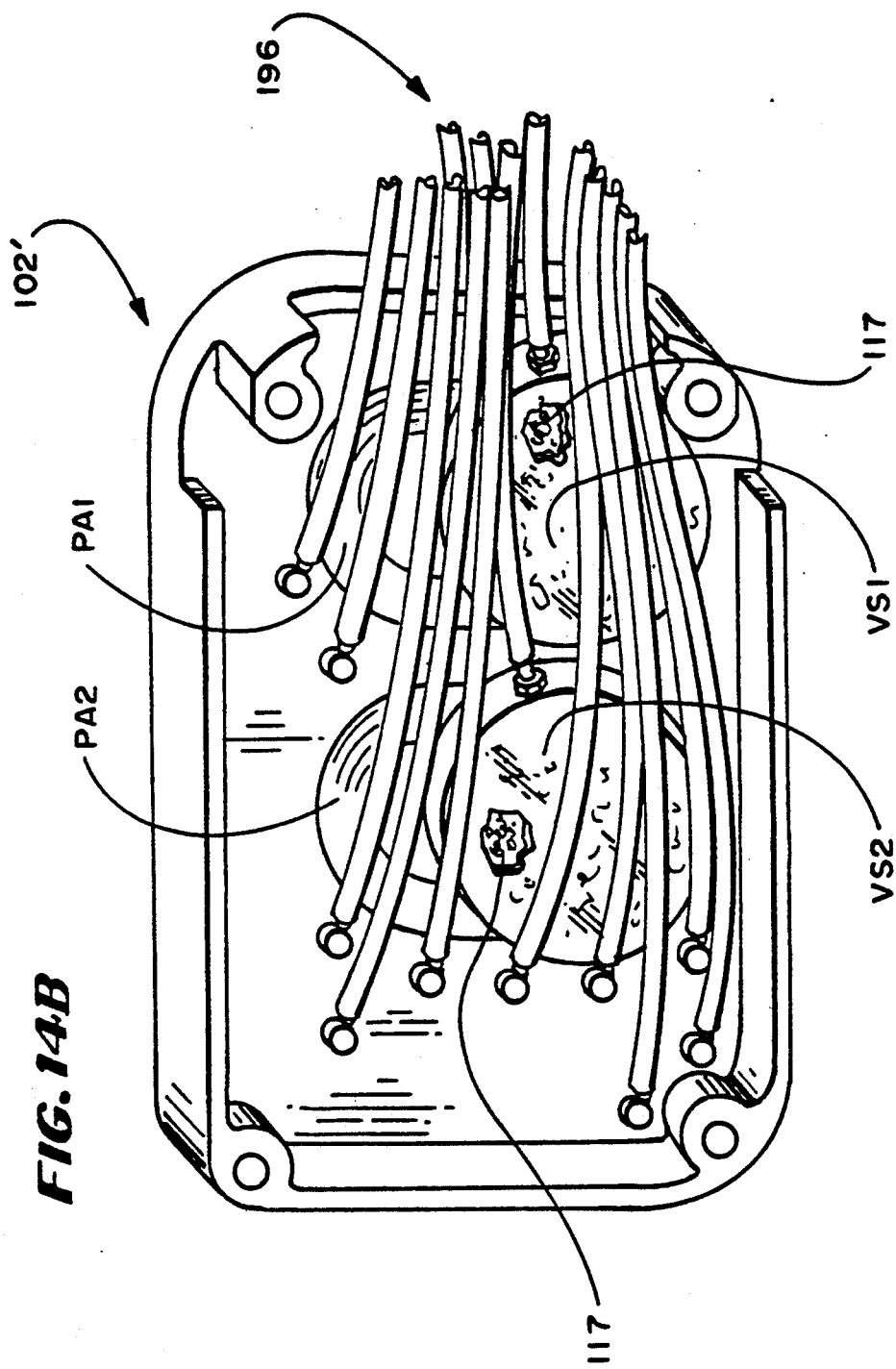
FIG. 14B is a perspective view of an alternative, preferred embodiment of a fluid pressure piston that can be used with the system shown in FIG. 1.

In a preferred arrangement (as FIG. 14B shows), the reference chambers VS1 and VS2 are carried by the piston element 102' itself, or at another located close to the pump actuators PA1 and PA2 within the cassette holder 100.

In this way, the reference chambers VS1 and VS2, like the pump actuators PA1 and PA2, exposed to generally the same temperature conditions as the cassette itself.

Also in the illustrated and preferred embodiment, inserts 117 occupy the reference chambers VS1 and VS2. Like the inserts 117 carried within the pump actuators PA1 and PA2, the reference chamber inserts 117 are made of an open cell foam material. By dampening and directing the application of pneumatic pressure, the reference chamber inserts 117 make measurement of air volumes faster and less complicated.

Preferably, the insert 117 also includes a heat conducting coating or material to help conduct heat into the reference chamber VS1 and VS2. In the illustrated embodiment, a thermal paste is applied to the foam insert.

This preferred arrangement minimizes the effects of temperature differentials upon liquid volume measurements.

Reference chamber VS1 communicates with the outlets of valves A0; A3: and A4 through a normally closed two way valve A2 in the manifold assembly 162. Reference chamber VS1 also communicates with a vent 352 through a normally closed two way valve A1 in the manifold assembly 162.

Transducer XVS1 in the manifold assembly 162 senses the amount of air pressure present within the reference chamber VS1. Transducer XP1 senses the amount of air pressure present in the first pump actuator PA1.

Likewise, reference chamber VS2 communicates with the outlets of valve B0; B1; and B4 through a normally closed two way valve B2 in the manifold assembly 162. Reference chamber VS2 also communicates with a filtered vent 356 through a normally closed two way valve B3 in the manifold assembly 162.

Transducer XVS2 in the manifold assembly 162 senses the amount of air pressure present within the reference chamber VS2. Transducer XP2 senses the amount of air pressure present in the second pump actuator PA2.

The controller 16 operates the network 350 to perform an air volume calculation twice, once during each draw (negative pressure) cycle and once again during each pump (positive pressure) cycle of each pump actuator PA1 and PA2.

The controller 16 operates the network 350 to perform the first air volume calculation after the operating pump chamber is filled with the liquid to be pumped (i.e., after its draw cycle). This provides an initial air volume ($V_i$).

The controller 16 operates the network 350 to perform the second air volume calculation after moving fluid out of the pump chamber (i.e., after the pump cycle). This provides a final air volume ($V_f$).

The controller 16 calculates the difference between the initial air volume $V_i$ and the final air volume $V_f$ to derive a delivered liquid volume ($V_d$), where:

$$V_d = V_f - V_i$$

The controller 16 accumulates $V_d$ for each pump chamber to derive total liquid volume pumped during a given procedure. The controller 16 also applies the incremental liquid volume pumped over time to derive flow rates.

The controller 16 derives $V_i$ in this way (pump chamber P1 is used as an example):

(1) The controller 16 actuates the valves C0 to C4 to close the inlet and outlet passages leading to the pump chamber P1 (which is filled with liquid). Valves A2 and A1 are normally closed, and they are kept that way.

(2) The controller 16 opens valve A1 to vent reference chamber VS1 to atmosphere. The controller 16 then conveys positive pressure to the pump actuator PA1, by opening either valve A3 (low-reference) or A4 (high-reference), depending upon the pressure mode selected for the pump stroke.

(3) The controller 16 closes the vent valve A1 and the positive pressure valve A3 or A4, to isolate the pump chamber PA1 and the reference chamber VS1.

(4) The controller 16 measures the air pressure in the pump actuator PA1 (using transducer XP1) ($IP_{d1}$) and the air pressure in the reference chamber VS1 (using transducer XVS1) ($IP_{s1}$).

(5) The controller 16 opens valve A2 to allow the reference chamber VS1 to equilibrate with the pump chamber PA1.

(6) The controller 16 measures the new air pressure in the pump actuator PA1 (using transducer XP1) ($IP_{d2}$) and the new air pressure in the reference chamber (using transducer XVS1) ($IP_{s2}$).

(7) The controller 16 closes the positive pressure valve A3 or A4.

(8) The controller 16 calculates initial air volume $V_i$ as follows:

$$V_i = \frac{(IP_{s1} - IP_{s2}) \cdot V_s}{(IP_{d2} - IP_{d1})}$$

After the pump chamber P1 is emptied of liquid, the same sequence of measurements and calculations are made to derive $V_f$, as follows:

(9) Keeping valve stations A2 and A1 closed, the controller 16 actuates the valves C0 to C4 to close the inlet and outlet passages leading to the pump chamber P1 (which is now emptied of liquid).

(10) The controller 16 opens valve A1 to vent reference chamber VS1 to atmosphere, and then conveys positive pressure to the pump actuator PA1, by opening either valve A3 (low-reference) or A4 (high-reference), depending upon the pressure mode selected for the pump stroke.

(11) The controller 16 closes the vent valve A1 and the positive pressure valve A3 or A4, to isolate the pump actuator PA1 and the reference chamber VS1.

(12) The controller 16 measures the air pressure in the pump actuator PA1 (using transducer XP1) ($FP_{d1}$) and the air pressure in the reference chamber VS1 (using transducer XVS1) ($FP_{s1}$).

(13) The controller 16 opens valve A2, allowing the reference chamber VS1 to equilibrate with the pump actuator.

(14) The controller 16 measures the new air pressure in the pump actuator PA1 (using transducer XP1) ($FP_{d2}$) and the new air pressure in the reference chamber (using transducer XVS1) ($FP_{s2}$).

(15) The controller 16 closes the positive pressure valve A3 or A4.

(16) The controller 16 calculates final air volume $V_f$ as follows:

$$V_f = \frac{(FP_{s1} - FP_{s2}) \cdot V_s}{(FP_{d2} - FP_{d1})}$$

The liquid volume delivered ($V_d$) during the preceding pump stroke is:

$$V_d = V_f - V_i$$

Preferably, before beginning another pump stroke, the operative pump actuator is vented to atmosphere (by actuating valves A2 and A1 for pump actuator PA1, and by actuating valves B2 and B3 for pump actuator PA2).

The controller 16 also monitors the variation of $V_d$ over time to detect the presence of air in the cassette pump chamber P1/P2. Air occupying the pump chamber P1/P2 reduces the capacity of the chamber to move liquid. If $V_d$ decrease over time, or if $V_d$ falls below a set expected value, the controller 16 attributes this condition to the buildup of air in the cassette chamber.

When this condition occurs, the controller 16 conducts an air removal cycle, in which liquid flow through the affected chamber is channeled through the top portion of the chamber to the drain or to the heater bag for a period of time. The air removal cycle rids the chamber of excess air and restores $V_d$ to expected values.

In another embodiment, the controller 16 periodically conducts an air detection cycle. In this cycle, the controller 16 delivers fluid into a given one of the pump chambers P1 and P2. The controller 16 then closes all valve stations leading into and out of the given pump chamber, to thereby trap the liquid within the pump chamber.

The controller 16 then applies air pressure to the actuator associated with the pump chamber and derives a series of air volume $V_i$ measurements over a period of time in the manner previously disclosed. Since the liquid trapped within the pump chamber is relatively incompressible, there should be virtually no variation in the measured $V_i$ during the time period, unless there is air present in the pump chamber. If $V_i$ does vary over a prescribed amount during the time period, the controller 16 contributes this to the presence of air in the pump chamber.

When this condition occurs, the controller 16 conducts an air removal cycle in the manner previously described.

The controller 16 performs the liquid volume calculations assuming that the temperature of the reference chamber VS1/VS2 does not differ significantly from the temperature of the pump chamber P1/P2.

One way to minimize any temperature difference is to mount the reference chamber as close to the pump chamber as possible. FIG. 14B shows this preferred alternative, where the reference chamber is physically mounted on the piston head 116.

Temperature differences can also be accounted for by applying a temperature correction factor ($F_t$) to the known air volume of the reference chamber $V_s$ to derive a temperature-corrected reference air volume $V_{st}$, as follows:

$$V_{st} = F_t * V_s$$

where:

$$F_t = C_t/R_t$$

and where:
- $C_t$ is the absolute temperature of the cassette (expressed in degrees Rankine or Kelvin), and
- $R_t$ is the temperature of the reference chamber (expressed in the same units as $C_t$).

In this embodiment, the network substitutes $V_{st}$ for $V_s$ in the above volume derivation calculations.

The value of $F_t$ can be computed based upon actual, real time temperature calculations using temperature sensors associated with the cassette and the reference chamber.

Because liquid volume measurements are derived after each pumping stroke, the same accuracy is obtained for each cassette loaded into the cycler, regardless of variations in tolerances that may exist among the cassettes used.

III. THE CYCLER CONTROLLER 16

FIGS. 9; 10; 17; and 18 show the cycler controller 16.

The controller 16 carries out process control and monitoring functions for the cycler 14. The controller 16 includes a user interface 367 with a display screen 370 and keypad 368. The user interface 367 receives characters from the keypad 368, displays text to a display screen 370, and sounds the speaker 372 (shown in FIGS. 9 and 10). The interface 367 presents status information to the user during a therapy session. The interface 367 also allows the user to enter and edit therapy parameters, and to issue therapy commands.

In the illustrated embodiment, the controller 16 comprises a central microprocessing unit (CPU) 358. The CPU is etched on the board 184 carried on stand off pins 182 atop the second module 88. Power harnesses 360 link the CPU 358 to the power supply 90 and to the operative elements of the manifold assembly 162.

The CPU 358 employs conventional real-time multitasking to allocate CPU cycles to application tasks. A periodic timer interrupt (for example, every 10 milliseconds) preempts the executing task and schedules another that is in a ready state for execution. If a reschedule is requested, the highest priority task in the ready state is scheduled. Otherwise, the next task on the list in the ready state is scheduled.

The following provides an overview of the operation of the cycler 14 under the direction of the controller CPU 358.

(A) The User Interface

Figure 25:
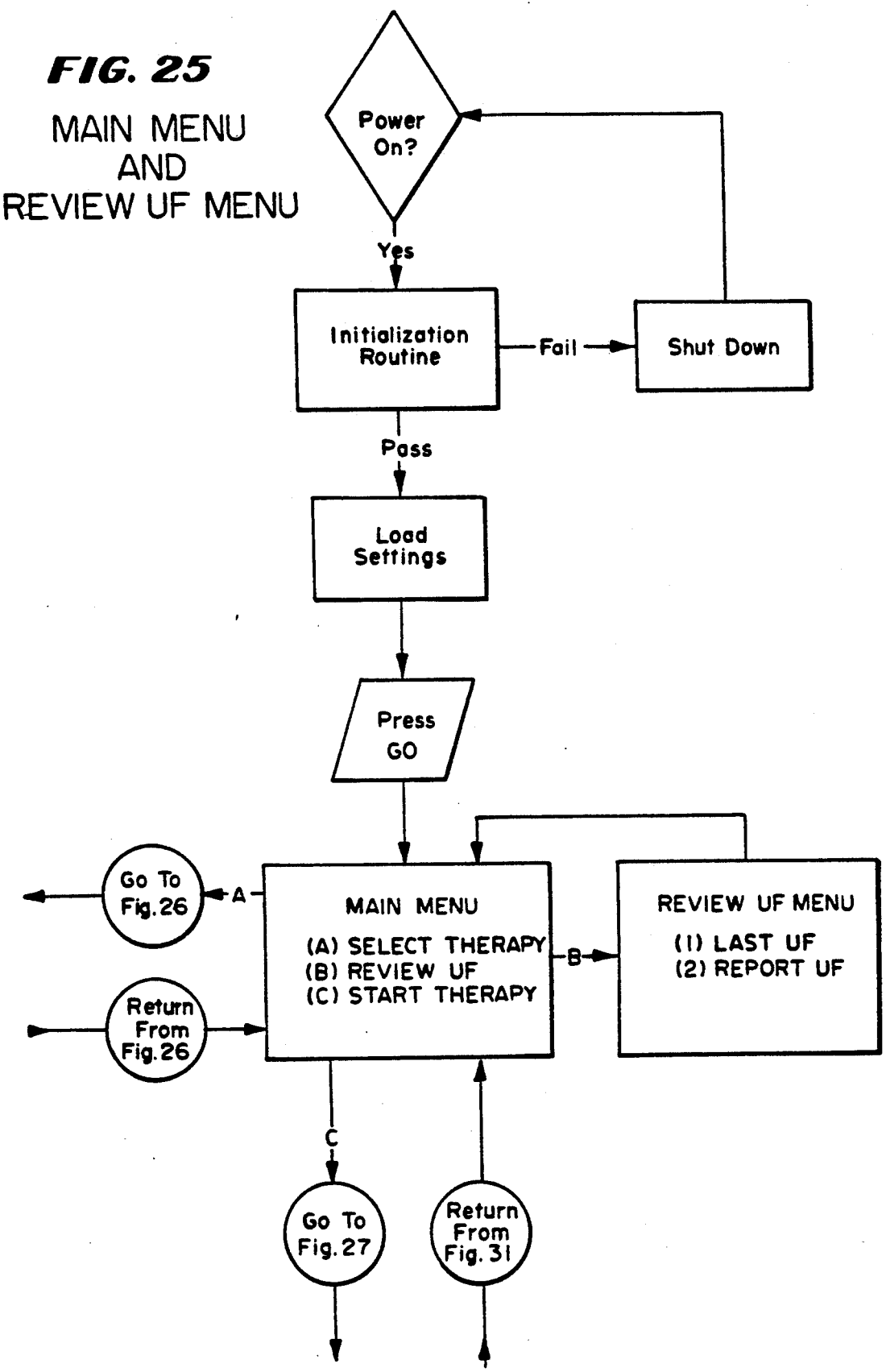
FIG. 25 is a flow chart showing the operation of the main menu and ultrafiltration review interfaces that the controller for the cycler shown in FIG. 1 employs.
Figure 26:
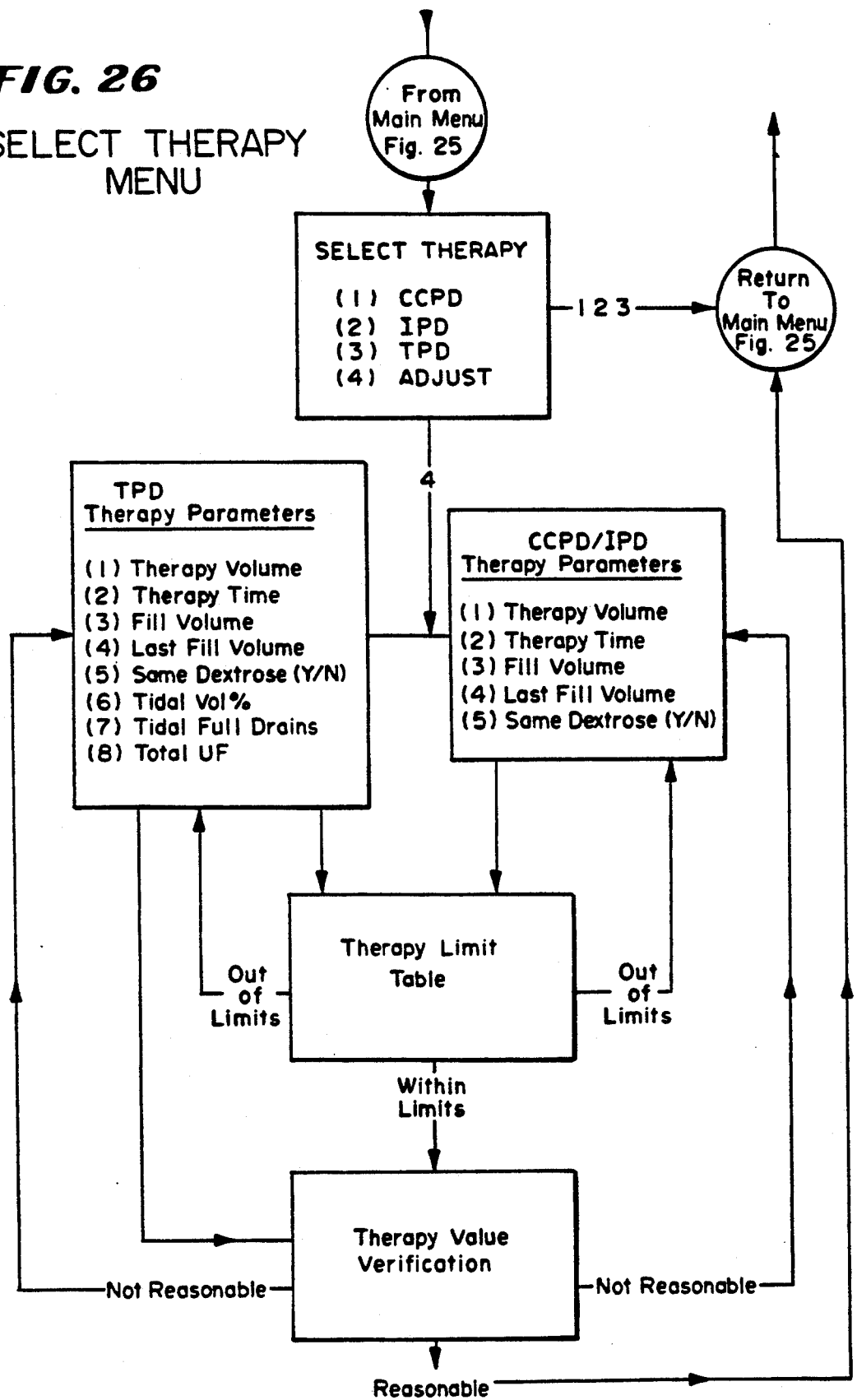
FIG. 26 is a flow chart showing the operation of the therapy selection interfaces that the controller for the cycler shown in FIG. 1 employs.

1. System Power Up/MAIN MENU (FIG. 25)

When power is turned on, the controller 16 runs through an INITIALIZATION ROUTINE.

During the initialization routine, the controller 16 verifies that its CPU 358 and associated hardware are working. If these power-up tests fail, the controller 16 enters a shutdown mode.

If the power-up tests succeed, the controller 16 loads the therapy and cycle settings saved in non-volatile RAM during the last power-down. The controller 16 runs a comparison to determine whether these settings, as loaded, are corrupt.

If the therapy and cycle settings loaded from RAM are not corrupt, the controller 16 prompts the user to press the GO key to begin a therapy session.

When the user presses the GO key, the controller 16 displays the MAIN MENU. The MAIN MENU allows the user to choose to (a) select the therapy and adjust the associated cycle settings; (b) review the ultrafiltrate figures from the last therapy session, and (c) start the therapy session based upon the current settings.

2. THERAPY SELECTION MENU (FIG. 26)

With choice (a) of the MAIN MENU selected, the controller 16 displays the THERAPY SELECTION MENU. This menu allows the user to specify the APD modality desired, selecting from CCPD, IPD, and TPD (with an without full drain phases).

The user can also select an ADJUST CYCLE SUBMENU. This submenu allows the user to select and change the therapy parameters.

For CCPD and IPD modalities, the therapy parameters include the THERAPY VOLUME, which is the total dialysate volume to be infused during the therapy session (in ml); the THERAPY TIME, which is the total time allotted for the therapy (in hours and minutes); the FILL VOLUME, which is the volume to be infused during each fill phase (in ml), based upon the size of the patient's peritoneal cavity; the LAST FILL VOLUME, which is the final volume to be left in the patient at the end of the session (in ml); and SAME DEXTROSE (Y OR N), which allows the user to specify a different dextrose concentration for the last fill volume.

For the TPD modality, the therapy parameters include THERAPY VOLUME, THERAPY TIME, LAST FILL VOLUME, AND SAME DEXTROSE (Y OR N), as above described. In TPD, the FILL VOLUME parameter is the initial tidal fill volume (in ml). TPD includes also includes as additional parameters TIDAL VOLUME PERCENTAGE, which is the fill volume to be infused and drained periodically, expressed as a percentage of the total therapy volume; TIDAL FULL DRAINS, which is the number of full drains in the therapy session; and TOTAL UF, which is the total ultrafiltrate expected from the patient during the session (in ml), based upon prior patient monitoring.

The controller 16 includes a THERAPY LIMIT TABLE. This Table sets predetermined maximum and minimum limits and permitted increments for the therapy parameters in the ADJUST CYCLE SUBMENU.

The controller 16 also includes a THERAPY VALUE VERIFICATION ROUTINE. This routine checks the parameters selected to verify that a reasonable therapy session has been programmed. The THERAPY VALUE VERIFICATION ROUTINE checks to assure that the selected therapy parameters include a dwell time of at least one minute; at least one cycle; and for TPD the expected filtrate is not unreasonably large (i.e., it is less than 25% of the selected THERAPY VOLUME). If any of these parameters is unreasonable, the THERAPY VALUE VERIFICATION ROUTINE places the user back in the ADJUST CYCLE SUBMENU and identifies the therapy parameter that is most likely to be wrong. The user is required to program a reasonable therapy before leaving the ADJUST CYCLE SUBMENU and begin a therapy session.

Once the modality is selected and verified, the controller 16 returns to user to the MAIN MENU.

3. REVIEW ULTRAFILTRATION MENU

With choice (b) of the MAIN MENU selected, the controller 16 displays the REVIEW ULTRAFILTRATION MENU (see FIG. 25).

This Menu displays LAST UF, which is the total volume of ultrafiltrate generated by the pervious therapy session. For CCPD and IPD modalities, the user can also select to ULTRAFILTRATION REPORT. This Report provides a cycle by cycle breakdown of the ultrafiltrate obtained from the previous therapy session.

4. SET-UP PROMPTS/LEAK TESTING

Figure 27:
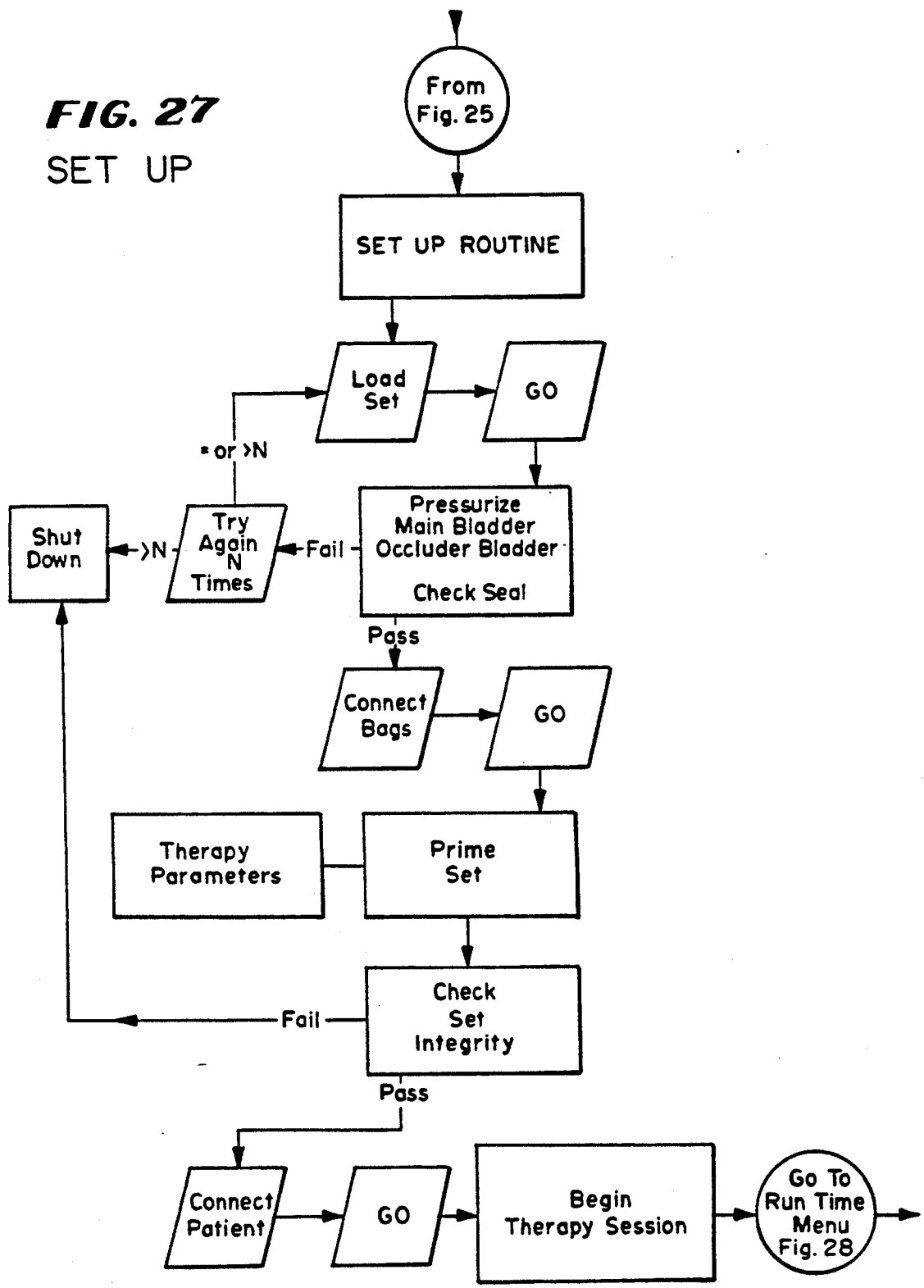
FIG. 27 is a flow chart showing the operation of the set up interfaces that the controller for the cycler shown in FIG. 1 employs.

With choice (c) of the MAIN MENU selected, the controller 16 first displays SET-UP PROMPTS to the user (as shown in FIG. 27).

The SET-UP PROMPTS first instruct the user to LOAD SET. The user is required to open the door; load a cassette; close the door; and press GO to continue with the set-up dialogue.

When the user presses GO, the controller 16 pressurizes the main bladder and occluder bladder and tests the door seal.

If the door seal fails, the controller 16 prompts the user to try again. If the door continues to fail a predetermined period of times, the controller 16 raises a SYSTEM ERROR and shuts down.

If the door seal is made, the SET-UP PROMPTS next instruct the user to CONNECT BAGS. The user is required to connect the bags required for the therapy session; to unclamp the liquid tubing lines being use and assure that the liquid lines that are not remained clamped (for example, the selected therapy may not require final fill bags, so liquid lines to these bags should remain clamped). Once the user accomplishes these tasks, he/she presses GO to continue with the set-up dialogue.

When GO is pressed, the controller 16 checks which lines are clamped and uses the programmed therapy parameters to determine which lines should be primed. The controller 16 primes the appropriate lines. Priming removes air from the set lines by delivering air and liquid from each bag used to the drain.

Next, the controller 16 performs a predetermined series of integrity tests to assure that no valves in the cassette leak; that there are no leaks between pump chambers; and that the occluder assembly stops all liquid flow.

The integrity tests first convey the predetermined high-relative negative air pressure ($-5.0$ psig) to the valve actuators VA1 to VA10. The transducer XNEG monitors the change in high-relative negative air pressure for a predetermined period. If the pressure change over the period exceeds a predetermined maximum, the controller 16 raises a SYSTEM ERROR and shuts down.

Otherwise, the integrity tests convey the predetermined high-relative positive pressure (7.0 psig) to the valve actuators VA1 to VA10. The transducer XHPOS monitors the change in high-relative positive air pressure for a predetermined period. If the pressure change over the period exceeds a predetermined maximum, the controller 16 raises a SYSTEM ERROR and shuts down.

Otherwise, the integrity tests proceed. The valve actuators VA1 to VA10 convey positive pressure to close the cassette valve stations V1 to V10. The tests first convey the predetermined maximum high-relative negative pressure to pump actuator PA1, while conveying the predetermined maximum high-relative positive pressure to pump actuator PA2. The transducers XP1 and XP2 monitor the pressures in the respective pump actuators PA1 and PA2 for a predetermined period. If pressure changes over the period exceed a predetermined maximum, the controller 16 raises a SYSTEM ERROR and shuts down.

Otherwise, the tests next convey the predetermined maximum high-relative positive pressure to pump actuator PA1, while conveying the predetermined maximum high-relative negative pressure to pump actuator PA2. The transducers XP1 and XP2 monitor the pressures in the respective pump actuators PA1 and PA2 for a predetermined period. If pressure changes over the period exceed a predetermined maximum, the controller 16 raises a SYSTEM ERROR and shuts down.

Otherwise, power to valve C6 is interrupted. This vents the occluder bladder 152 and urges the occluder blade and plate 144/148 together, crimping cassette tubing 26 to 34 closed. The pump chambers P1 and P2 are operated at the predetermined maximum pressure conditions and liquid volume measurements taken in the manner previously described. If either pump chamber P1/P2 moves liquid pass the closed occluder blade and plate 144/148, the controller 16 raises a SYSTEM ERROR and shuts down.

If all integrity tests succeed, the SET-UP PROMPTS next instruct the user to CONNECT PATIENT. The user is required to connect the patient according to the operator manual and press GO to begin the dialysis therapy session selected.

The controller 16 begins the session and displays the RUN TIME MENU.

5. RUN TIME MENU

Figure 28:
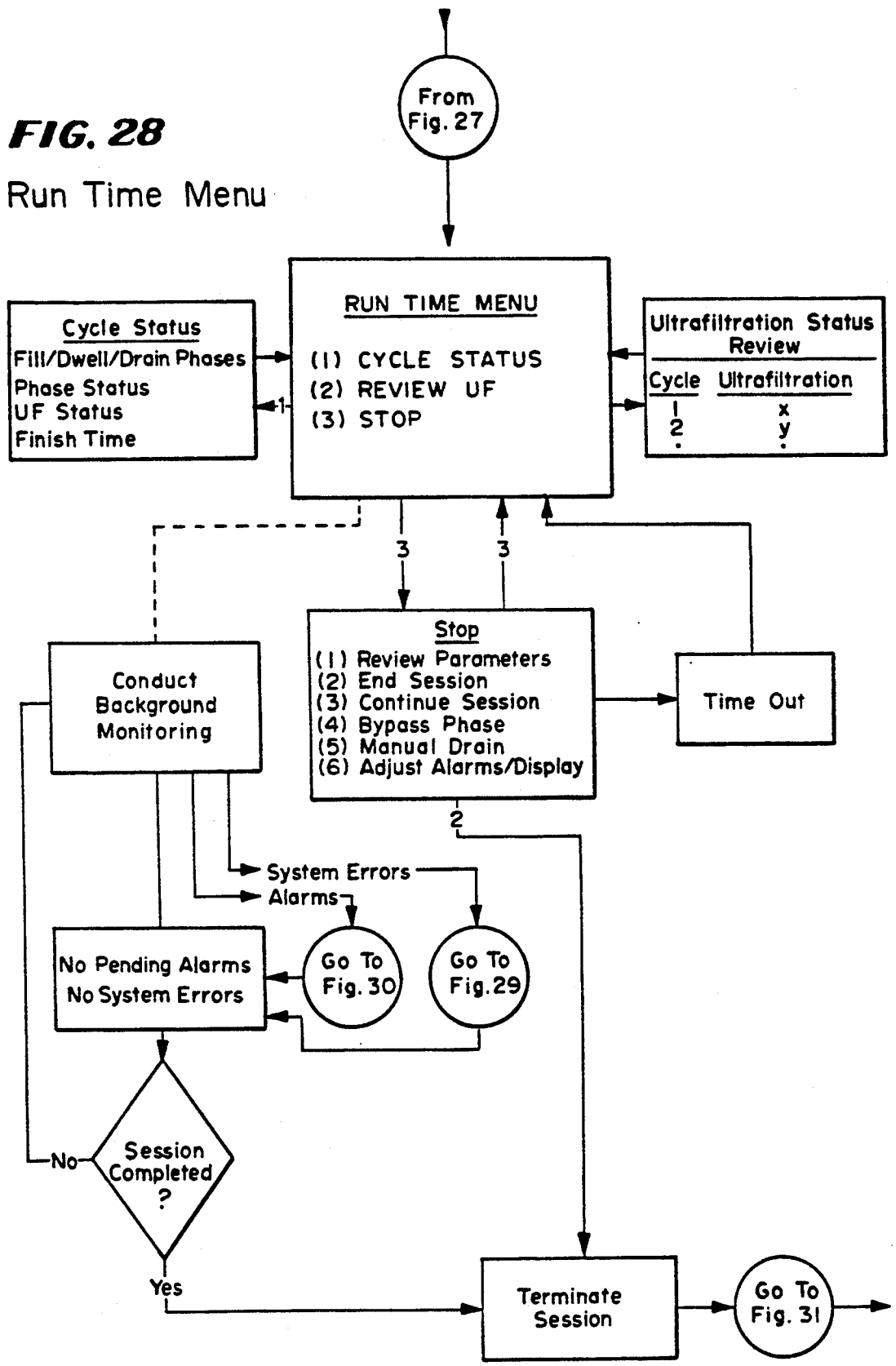
FIG. 28 is a flow chart showing the operation of the run time interfaces that the controller for the cycler shown in FIG. 1 employs.

Attention is now directed to FIG. 28.

The RUN TIME MENU is the active therapy interface. The RUN TIME MENU provides an updated real-time status report of the current progress of the therapy session.

The RUN TIME MENU includes the CYCLE STATUS, which identifies the total number of fill/dwell/drain phases to be conducted and the present number of the phase underway (e.g., Fill 3 of 10); the PHASE STATUS, which displays the present fill volume, counting up from 0 ml; the ULTRAFILTRATION STATUS, which displays total ultrafiltrate accumulated since the start of the therapy session; the TIME, which is the present time; and FINISH TIME, which is the time that the therapy session is expected to end.

Preferably, the user can also select in the RUN TIME MENU an ULTRAFILTRATION STATUS REVIEW SUBMENU, which displays a cycle by cycle breakdown of ultrafiltration accumulated.

From the RUN TIME MENU, the user can also select to STOP. The controller 16 interrupts the therapy session and displays the STOP SUBMENU. The STOP SUBMENU allows the user to REVIEW the programmed therapy parameters and make change to the parameters; to END the therapy session; to CONTINUE the therapy session; to BYPASS the present phase; to conduct a MANUAL DRAIN; or ADJUST the intensity of the display and loudness of alarms.

REVIEW restricts the type of changes that the user can make to the programmed parameters. For example, in REVIEW, the user cannot adjust parameters above or below a maximum specified amounts.

CONTINUE returns the user to the RUN TIME MENU and continue the therapy session where i left off.

The controller 16 preferably also includes specified time-outs for the STOP SUBMENU. For example, if the user does not take any action in the STOP SUBMENU for 30 minutes, the controller 16 automatically executes CONTINUE to return to the RUN TIME MENU and continue the therapy session. If the user does not take any action for 2 minutes after selecting REVIEW, the controller 16 also automatically executes CONTINUE.

6. Background Monitoring Routine/System Errors

Figure 29:
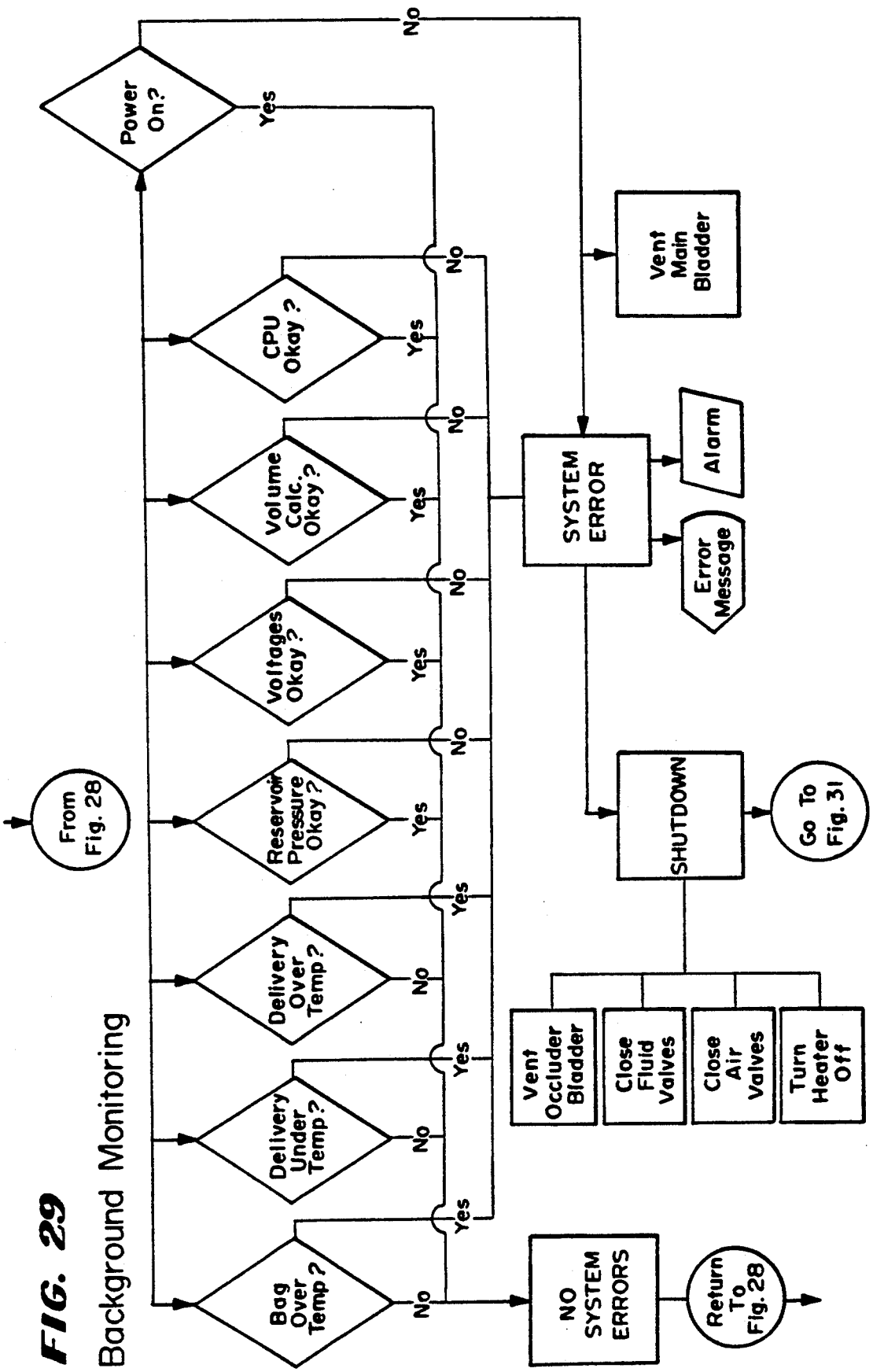
FIG. 29 is a flow chart showing the operation of the background monitoring that the controller for the cycler shown in FIG. 1 employs.

The controller 16 includes a BACKGROUND MONITORING ROUTINE that verifies system integrity at a predetermined intervals during the therapy session (e.g., every 10 seconds) (as FIG. 29 shows).

The BACKGROUND MONITORING ROUTINE includes

BAG OVER TEMP, which verifies that the heater bag is not too hot (e.g., not over 44 degrees C.);

DELIVERY UNDER TEMP, which verifies that the liquid delivered to the patient is not too cold (e.g, less than 33 degrees C.);

DELIVERY OVER TEMP, which verifies that the liquid delivered to the patient is not too hot (e.g, over 38 degrees C.);

MONITOR TANKS, which verifies that the air tanks are at their operating pressures (e.g., positive tank pressure at 7.5 psi +/−0.7 psi; patient tank at 5.0 psi +/−0.7 psi, except for heater to patient line, which is 1.5 psi +/−0.2 psi; negative tank pressure at −5.0 psi +/−0.7 psi, except for patient to drain line, which is at −0.8 psi +/−0.2 psi);

CHECK VOLTAGES, which verify that power supplies are within their noise and tolerance specs;

VOLUME CALC, which verifies the volume calculation math; and

CHECK CPU, checks the processor and RAM.

When the BACKGROUND MONITORING ROUTINE senses an error, the controller 16 raises a SYSTEM ERROR. Loss of power also raises a SYSTEM ERROR. When SYSTEM ERROR occurs, the controller 16 sounds an audible alarm and displays a message informing the user about the problem sensed.

When SYSTEM ERROR occurs, the controller 16 also shuts down the cycler 14. During shut down, the controller 16 ensures that all liquid delivery is stopped, activates the occluder assembly, closes all liquid and air valves, turns the heater plate elements off. If SYSTEM ERROR occurs due to power failure, the controller 16 also vents the emergency bladder, releasing the door.

7. SELF-DIAGNOSTICS AND TROUBLE SHOOTING

According to the invention, the controller 16 monitors and controls pneumatic pressure within the internal pressure distribution system 86. Based upon pneumatic pressure measurements, the controller 16 calculates the amount and flow rate of liquid moved. The controller does not require an additional external sensing devices to perform any of its control or measurement functions.

As a result, the system 10 requires no external pressure, weight, or flow sensors for the tubing 26 to 34 or the bags 20/22 to monitor and diagnose liquid flow conditions. The same air pressure that moves liquid through the system 10 also serves to sense and diagnose all relevant external conditions affecting liquid flow, like an empty bag condition, a full bag condition, and an occluded line condition.

Moreover, strictly by monitoring the pneumatic pressure, the controller 16 is able to distinguish a flow problem emanating from a liquid source from a flow problem emanating from a liquid destination.

Based upon the liquid volume measurements derived by the measurement network 350, the controller 16 also derives liquid flow rate. Based upon values and changes in derived liquid flow rate, the controller 16 can detect an occluded liquid flow condition. Furthermore, based upon derived liquid flow rates, the controller can diagnose and determine the cause of the occluded liquid flow condition.

The definition of an "occluded flow" condition can vary depending upon the APD phase being performed. For example, in a fill phase, an occluded flow condition can represent a flow rate of less than 20 ml/min. In a drain phase, the occluded flow condition can represent a flow rate of less than 10 ml/min. In a bag to bag liquid transfer operation, an occluded flow condition can represent a flow rate of less than 25 ml/min. Occluded flow conditions for pediatric APD sessions can be placed at lower set points.

When the controller 16 detects an occluded flow condition, it implements the following heuristic to determine whether the occlusion is attributable to a given liquid source or a given liquid destination.

When the controller 16 determines that the cassette cannot draw liquid from a given liquid source above the occluded flow rate, the controller 16 determines whether the cassette can move liquid toward the source above the occluded flow rate (i.e., it determines whether the liquid source can serve as a liquid destination). If it can, the controller 16 diagnoses the condition as an empty liquid source condition.

When the controller 16 determines that the cassette cannot push liquid toward a given destination above the occluded flow rate, it determines whether the cassette can draw liquid from the destination above the occluded flow rate (i.e., it determines whether the liquid destination can serve as a liquid source). If it can, the controller diagnoses the condition as being a full liquid destination condition.

When the controller 16 determines that the cassette can neither draw or push liquid to or from a given source or destination above the occluded flow rate, the controller 16 interprets the condition as an occluded line between the cassette and the particular source or destination.

In this way, the system 10 operates by controlling pneumatic fluid pressure, but not by reacting to external fluid or liquid pressure or flow sensing.

8. ALARMS

Figure 30:
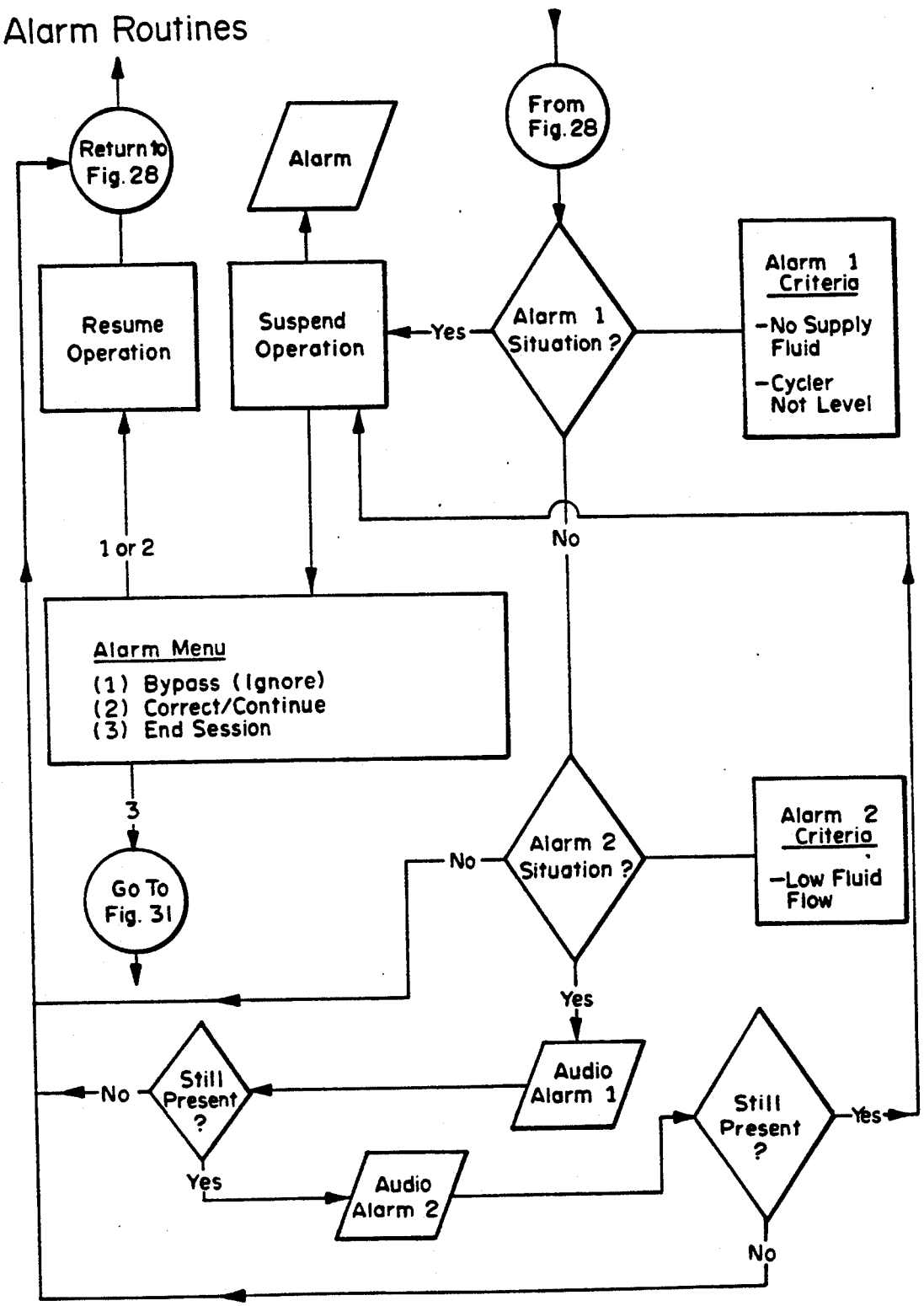
FIG. 30 is a flow chart showing the operation of the alarm routines that the controller for the cycler shown in FIG. 1 employs.

With no SYSTEM ERRORS, the therapy session automatically continues unless the controller 16 raises an ALARM1 or ALARM2. FIG. 30 shows the ALARM1 and ALARM2 routines.

The controller 16 raises ALARM1 in situations that require user intervention to correct. The controller 16 raises ALARM1 when the controller 16 senses no supply liquid; or when the cycler 14 is not level. When ALARM1 occurs, the controller 16 suspends the therapy session and sounds an audible alarm. The controller 16 also displays an ALARM MENU that informs the user about the condition that should be corrected.

The ALARM MENU gives the user the choice to correct the condition and CONTINUE; to END the therapy; or to BYPASS (i.e., ignore) the condition and resume the therapy session.

The controller 16 raises ALARM2 in situations that are anomalies but will typically correct themselves with minimum or no user intervention. For example, the controller 16 raises ALARM2 when the controller 16 initially senses a low flow or an occluded lines. In this situation, the patient might have rolled over onto the catheter and may need only to move to rectify the matter.

When ALARM2 occurs, the controller 16 generates a first audible signal (e.g., 3 beeps). The controller 16 then mutes the audible signal for 30 seconds. If the condition still exists after 30 second, the controller 16 generates a second audible signal (e.g., 8 beeps) The controller 16 again mutes the audible signal. If the condition still exists 30 seconds later, the controller 16 raises an ALARM1, as described above. The user is then required to intervene using the ALARM MENU.

9. POST THERAPY PROMPTS

Figure 31:
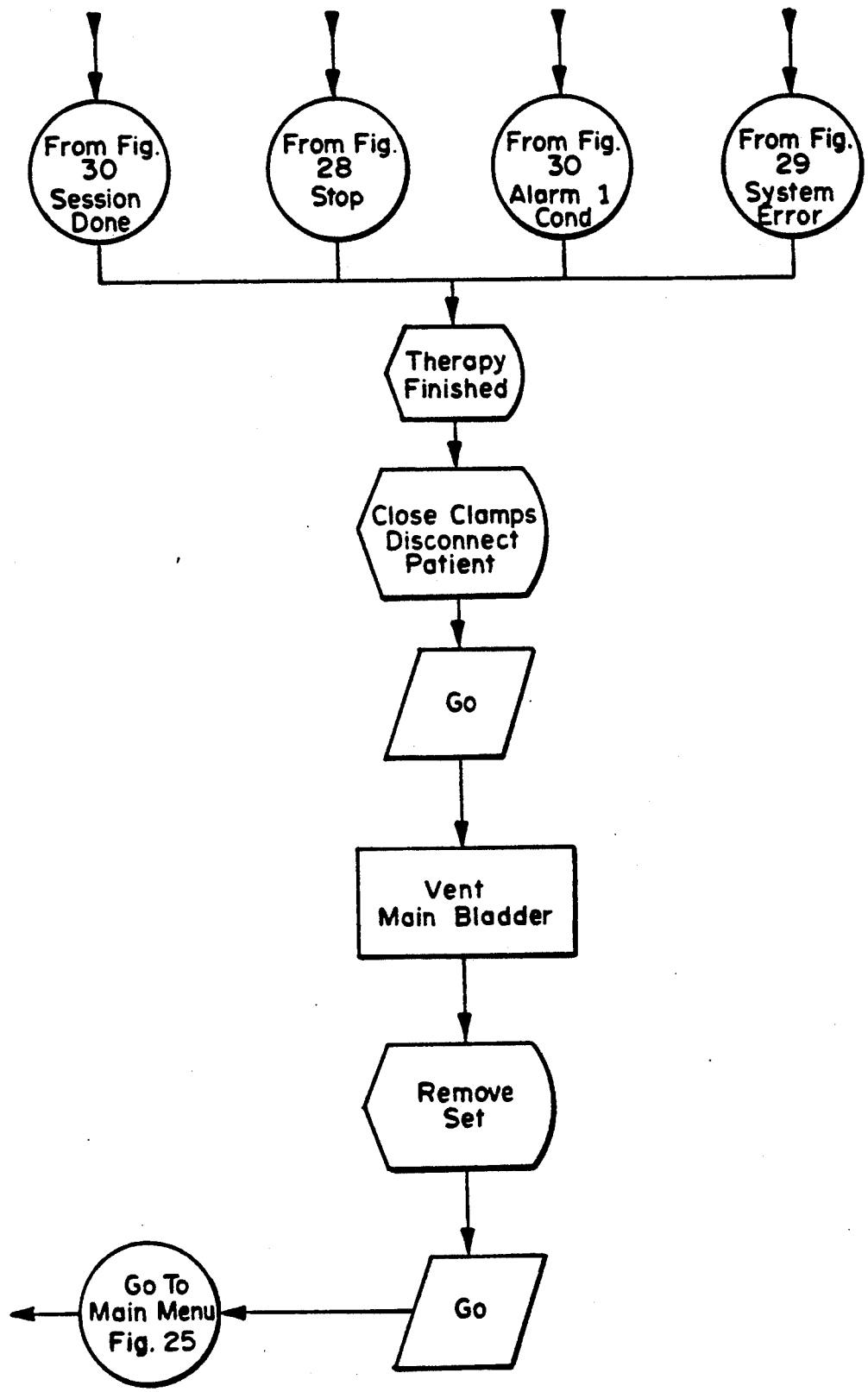
FIG. 31 is a flow chart showing the operation of the post therapy interfaces that the controller for the cycler shown in FIG. 1 employs.

The controller 16 terminates the session when (a) the prescribed therapy session is successfully completed; (b) the user selects END in the STOP SUBMENU or the ALARM MENU; or (c) a SYSTEM ERROR condition occurs (see FIG. 31).

When any of these events occur, the controller 16 displays POST THERAPY PROMPTS to the user. The POST THERAPY PROMPTS inform the user THERAPY FINISHED, to CLOSE CLAMPS, and to DISCONNECT PATIENT. The user presses GO to advance the prompts.

Once the user disconnects the patient and presses GO, the controller 16 displays PLEASE WAIT and depressurizes the door. Then the controller 16 then directs the user to REMOVE SET.

Once the user removes the set and presses GO, the controller 16 returns to user to the MAIN MENU.

(B) Controlling an APD Therapy Cycle

1. Fill phase

In the fill phase of a typical three phase APD cycle, the cycler 14 transfers warmed dialysate from the heater bag 22 to the patient.

The heater bag 22 is attached to the first (uppermost) cassette port 27. The patient line 34 is attached to the fifth (bottommost) cassette port 35.

As FIG. 32 shows, the fill phase involves drawing warmed dialysate into cassette pump chamber P1 through primary liquid path F1 via branch liquid path F6. Then, pump chamber P1 expels the heated dialysate through primary liquid path F5 via branch liquid path F8.

To expedite pumping operations, the controller 16 preferably works pump chamber P2 in tandem with pump chamber P1. The controller 16 draws heated dialysate into pump chamber P2 through primary liquid path F1 via branch liquid path F7. Then, pump chamber P2 expels the heated dialysate through primary liquid path F5 through branch liquid path F9.

The controller 16 works pump chamber P1 in a draw stroke, while working pump chamber P2 in a pump stroke, and vice versa.

In this sequence, heated dialysate is always introduced into the top portions of pump chambers P1 and P2. The heated dialysate is always discharged through the bottom portions of pump chambers P1 and P2 to the patient free of air.

Furthermore, during liquid transfer directly with the patient, the controller 16 can supply only low-relative positive and negative pressures to the pump actuators PA1 and PA2.

In carrying out this task, the controller 16 alternates the following sequences 1 and 2:

1. Perform pump chamber P1 draw stroke (drawing a volume of heated dialysate into pump chamber P1 from the heater bag), while performing pump chamber P2 pump stroke (expelling a volume of heated dialysate from pump chamber P2 to the patient).
   (i) Open inlet path F1 to pump chamber P1, while closing inlet path F1 to pump chamber P2. Actuate valve C0 to supply high-relative negative pressure to valve actuator VA1, opening cassette valve station V1. Actuate valves C1; D1; and D2 to supply high-relative positive pressure to valve actuators VA2; VA3: and VA4, closing cassette valve station V2; V3; and V4.
   (ii) Close outlet path F5 to pump chamber P1, while opening outlet path F5 to pump chamber P2. Actuate valves C2 to C4 and D3 to D5 to supply high-relative positive pressure to valve actuators VA8 to V10 and VA5 to VA7, closing cassette valve stations V8 to V10 and V5 to V7. Actuate valve D5 to supply high-relative negative pressure to valve actuator VA7, opening cassette valve station V7.
   (iii) Flex the diaphragm underlying actuator PA1 out. Actuate valve A0 to supply low-relative negative pressure to pump actuator PA1.
   (iv) Flex the diaphragm underlying actuator PA2 in. Actuate valve B1 to supply low-relative positive pressure to pump actuator PA2.
2. Perform pump chamber P2 draw stroke (drawing a volume of heated dialysate into pump chamber P2 from the heater bag), while performing pump chamber P1 pump stroke (expelling a volume of heated dialysate from pump chamber P1 to the patient).
   (i) Open inlet path F1 to pump chamber P2, while closing inlet path F1 to pump chamber P1. Actuate valves C0; C1; and D2 to supply high-relative positive pressure to valve actuators VA1; VA2; and VA4, closing cassette valve stations V1; V2; and V4. Actuate valve D1 to supply high-relative negative pressure to valve actuator VA3, opening cassette valve station V3.

(ii) Close outlet path F5 to pump chamber P2, while opening outlet path F5 to pump chamber P1. Actuate valve C2 to supply high-relative negative pressure to valve actuator VA8, opening cassette valve station V8. Actuate valves D3 to D5; C2; and C4 to supply high-relative positive pressure to valve actuators VA5 to VA7; V9; and V10, closing cassette valve stations V5 to V7; V9; and V10.

(iii) Flex the diaphragm underlying actuator PA1 in. Actuate valve A3 to supply low-relative positive pressure to pump actuator PA1.

(iv) Flex the diaphragm underlying actuator PA2 out. Actuate valve B4 to supply low-relative negative pressure to pump actuator PA2.

2. Dwell Phase

Once the programmed fill volume has been transferred to the patient, the cycler 14 enters the second or dwell phase. In this phase, the cycler 14 replenishes the heater bag by supplying fresh dialysate from a source bag.

The heater bag is attached to the first (uppermost) cassette port. The source bag line is attached to the fourth cassette port, immediately above the patient line.

As FIG. 33 shows, the replenish heater bag phase involves drawing fresh dialysate into cassette pump chamber P1 through primary liquid path F4 via branch liquid path F8. Then, pump chamber P1 expels the dialysate through primary liquid path F1 via branch liquid path F6.

To expedite pumping operations, the controller 16 preferably works pump chamber P2 in tandem with pump chamber P1. The controller 16 draws fresh dialysate into cassette pump chamber P2 through primary liquid path F4 via branch liquid path F9. Then, pump chamber P2 expels the dialysate through primary liquid path F1 via branch liquid path F7.

The controller 16 works pump chamber P1 in a draw stroke, while working pump chamber P2 in a pump stroke, and vice versa.

In this sequence, fresh dialysate is always introduced into the bottom portions of pump chambers P1 and P2. The fresh dialysate is always discharged through the top portions of pump chambers P1 and P2 to the heater bag. This allows entrapped air to be removed from the pump chambers P1 and P2.

Furthermore, since liquid transfer does not occur directly with the patient, the controller 16 supplies high-relative positive and negative pressures to the pump actuators PA1 and PA2.

In carrying out this task, the controller 16 alternates the following sequences:

1. Perform pump chamber P1 draw stroke (drawing a volume of fresh dialysate into pump chamber P1 from a source bag), while performing pump chamber P2 pump stroke (expelling a volume of fresh dialysate from pump chamber P2 to the heater bag).

(i) Open inlet path F4 to pump chamber P1, while closing inlet path F4 to pump chamber P2. Actuate valve C3 to supply high-relative negative pressure to valve actuator VA9, opening cassette valve station V9. Actuate valves D3 to D5; C2; and C4 to supply high-relative positive pressure to valve actuators VA5 to VA8; and VA10, closing cassette valve stations V5 to V8 and V10.

(ii) Close outlet path F1 to pump chamber P1, while opening outlet path F1 to pump chamber P2. Actuate valves C0; C1; and D2 to supply high-relative positive pressure to valve actuators VA1; VA2 and VA4, closing cassette valve stations V1; V2; and V4. Actuate valve D1 to supply high-relative negative pressure to valve actuator VA3, opening cassette valve station V3.

(iii) Flex the diaphragm underlying actuator PA1 out. Actuate valve A0 to supply high-relative negative pressure to pump actuator PA1.

(iv) Flex the diaphragm underlying actuator PA2 in. Actuate valve B0 to supply high-relative positive pressure to pump actuator PA2.

2. Perform pump chamber P2 draw stroke (drawing a volume of fresh dialysate into pump chamber P2 from a source bag), while performing pump chamber P1 pump stroke (expelling a volume of fresh dialysate from pump chamber P1 to heater bag).

(i) Close inlet path F4 to pump chamber P1, while opening inlet path F4 to pump chamber P2. Actuate valve D5 to supply high-relative negative pressure to valve actuator VA6, opening cassette valve station V6. Actuate valves C3 to C4; D3; and D5 to supply high-relative positive pressure to valve actuators VA5 and VA7 to VA10, closing cassette valve stations V5 and V7 to V10.

(ii) Open outlet path F1 to pump chamber P1, while closing outlet path F1 to pump chamber P2. Actuate valve C0 to supply high-relative negative pressure to valve actuator VA1, opening cassette valve station V1. Actuate valves C1; D1; and D2 to supply high-relative positive pressure to valve actuators VA2 to VA4, closing cassette valve station V2 to V4.

(iii) Flex the diaphragm underlying actuator PA1 in. Actuate valve A4 to supply high-relative positive pressure to pump actuator PA1.

(iv) Flex the diaphragm underlying actuator PA2 out. Actuate valve B4 to supply high-relative negative pressure to pump actuator PA2.

3. Drain Phase

When the programmed drain phase ends, the cycler 14 enters the third or drain phase. In this phase, the cycler 14 transfers spent dialysate from the patient to a drain.

The drain line is attached to the second cassette port. The patient line is attached to the fifth, bottommost cassette port.

As FIG. 34 shows, the drain phase involves drawing spent dialysate into cassette pump chamber P1 through primary liquid path F5 via branch liquid path F8. Then, pump chamber P1 expels the dialysate through primary liquid path F2 via branch liquid path F6.

To expedite pumping operations, the controller 16 works pump chamber P2 in tandem with pump chamber P1. The controller 16 draws spend dialysate into cassette pump chamber P2 through primary liquid path F5 via branch liquid path F9. Then, pump chamber P2 expels the dialysate through primary liquid path F2 via branch liquid path F7.

The controller 16 works pump chamber P1 in a draw stroke, while working pump chamber P2 in a pump stroke, and vice versa.

In this sequence, spent dialysate is always introduced into the bottom portions of pump chambers P1 and P2. The spent dialysate is always discharged through the top portions of pump chambers P1 and P2 to the heater bag. This allows air to be removed from the pump chambers P1 and P2.

Furthermore, since liquid transfer does occur directly with the patient, the controller 16 supplies low-relative positive and negative pressures to the pump actuators PA1 and PA2.

In carrying out this task, the controller 16 alternates the following sequences:

1. Perform pump chamber P1 draw stroke (drawing a volume of spent dialysate into pump chamber P1 from the patient), while performing pump chamber P2 pump stroke (expelling a volume of spent dialysate from pump chamber P2 to the drain).
   (i) Open inlet path F5 to pump chamber P1, while closing inlet path F5 to pump chamber P2. Actuate valve C2 to supply high-relative negative pressure to valve actuator VA8, opening cassette valve station V8. Actuate valves D3 to D5, C3, and C4 to supply high-relative positive pressure to valve actuators VA5 to VA7, VA9 and VA10, closing cassette valve stations V5 to V7, V9, and V10.
   (ii) Close outlet path F2 to pump chamber P1, while opening outlet path F2 to pump chamber P2. Actuate valves C0; C1; and D1 to supply high-relative positive pressure to valve actuators VA1; VA2 and VA3, closing cassette valve stations V1; V2; and V3. Actuate valve D2 to supply high-relative negative pressure to valve actuator VA4, opening cassette valve station V4.
   (iii) Flex the diaphragm underlying actuator PA1 out. Actuate valve A0 to supply low-relative negative pressure to pump actuator PA1.
   (iv) Flex the diaphragm underlying actuator PA2 in. Actuate valve B1 to supply low-relative positive pressure to pump actuator PA2.

2. Perform pump chamber P2 draw stroke (drawing a volume of spent dialysate into pump chamber P2 from the patient), while performing pump chamber P1 pump stroke (expelling a volume of spent dialysate from pump chamber P1 to the drain).
   (i) Close inlet path F5 to pump chamber P1, while opening inlet path F5 to pump chamber P2. Actuate valve D5 to supply high-relative negative pressure to valve actuator VA7, opening cassette valve station V7. Actuate valves D3; D4 and C2 to C4 to supply high-relative positive pressure to valve actuators VA5; VA6; and VA8 to VA10, closing cassette valve stations V5, V6, and V8 to V10.
   (ii) Open outlet path F2 to pump chamber P1, while closing outlet path F2 to pump chamber P2. Actuate valve C1 to supply high-relative negative pressure to valve actuator VA2, opening cassette valve station V2. Actuate valves C0; D1; and D2 to supply high-relative positive pressure to valve actuators VA1; VA3; and VA4, closing cassette valve station V1; V3; and V4.
   (iii) Flex the diaphragm underlying actuator PA1 in. Actuate valve A3 to supply low-relative positive pressure to pump actuator PA1.
   (iv) Flex the diaphragm underlying actuator PA2 out. Actuate valve B4 to supply low-relative negative pressure to pump actuator PA2.

The controller 16 senses pressure using transducers XP1 and XP2 to determine when the patient's peritoneal cavity is empty.

The drain phase is followed by another fill phase and dwell phase, as previously described.

4. Last Dwell Phase

In some APD procedures, like CCPD, after the last prescribed fill/dwell/drain cycle, the cycler 14 infuses a final fill volume. The final fill volume dwells in the patient through the day. It is drained at the outset of the next CCPD session in the evening. The final fill volume can contain a different concentration of dextrose than the fill volume of the successive CCPD fill/dwell/drain fill cycles the cycler 14 provides. The chosen dextrose concentration sustains ultrafiltration during the day-long dwell cycle.

In this phase, the cycler 14 infuses fresh dialysate to the patient from a "last fill" bag. The "last fill" bag is attached to the third cassette port. During the last swell phase, the heater bag is emptied, and solution from last bag volume is transferred to the heater bag. From there, the last fill solution is transferred to the patient to complete the last fill phase.

The last dwell phase involves drawing liquid from the heater bag into pump chamber P1 through primary liquid path F1 via branch path F6. The, the pump chamber P1 expels the liquid to the drain through primary liquid path F2 via branch liquid path F6.

To expedite drainage of the heater bag, the controller 16 works pump chamber P2 in tandem with pump chamber P1. The controller 16 draws liquid from the heater bag into pump chamber P2 through primary liquid path F1 via branch liquid path F7. Then, pump chamber P2 expels liquid to the drain through primary liquid path F2 via branch liquid path F7.

The controller 16 works pump chamber P1 in a draw stroke, while working pump chamber P2 in a pump stroke, and vice versa.

Once the heater bag is drained, the controller 16 draws fresh dialysate from the "last fill" bag into cassette pump chamber P1 through primary liquid path F3 via branch liquid path F8. Then, pump chamber P1 expels the dialysate to the heater bag through primary liquid path F1 via the branch liquid path F6.

As before, to expedite pumping operations, the controller 16 preferably works pump chamber P2 in tandem with pump chamber P1. The controller 16 draws fresh dialysate from the "last fill" bag into cassette pump chamber P2 through primary liquid path F3 via branch liquid path F9. Then, pump chamber P2 expels the dialysate through primary liquid path F1 via the branch liquid path F7.

The controller 16 works pump chamber P1 in a draw stroke, while working pump chamber P2 in a pump stroke, and vice versa.

In this sequence, fresh dialysate from the "last fill" bag is always introduced into the bottom portions of pump chambers P1 and P2. The fresh dialysate is always discharged through the top portions of pump chambers P1 and P2 to the heater bag. This allows air to be removed from the pump chambers P1 and P2.

Furthermore, since liquid transfer does not occur directly with the patient, the controller 16 can supply high-relative positive and negative pressures to the pump actuators PA1 and PA2.

In carrying out this task, the controller 16 alternates the following sequences (see FIG. 35):

1. Perform pump chamber P1 draw stroke (drawing a volume of fresh dialysate into pump chamber P1 from the "last fill" bag), while performing pump chamber P2 pump stroke (expelling a volume of fresh dialysate from pump chamber P2 to the heater bag).
   (i) Open inlet path F3 to pump chamber P1, while closing inlet path F3 to pump chamber P2. Actuate valve C4 to supply high-relative negative pressure to valve actuator VA10, opening cassette valve station V10. Actuate valves D3 to D5; C2; and C3 to supply high-relative positive pressure to valve actuators VA5 to VA9, closing cassette valve stations V5 to V9.
   (ii) Close outlet path F1 to pump chamber P1, while opening outlet path F1 to pump chamber P2. Actuate valves C0; C1; and D2 to supply high-relative positive pressure to valve actuators VA1; VA2 and VA4, closing cassette valve stations V1; V2; and V4. Actuate valve D1 to supply high-relative negative pressure to valve actuator VA3, opening cassette valve station V3.
   (iii) Flex the diaphragm underlying actuator PA1 out. Actuate valve A0 to supply high-relative negative pressure to pump actuator PA1.
   (iv) Flex the diaphragm underlying actuator PA2 in. Actuate valve B0 to supply high-relative positive pressure to pump actuator PA2.

2. Perform pump chamber P2 draw stroke (drawing a volume of fresh dialysate into pump chamber P2 from the "last fill" bag), while performing pump chamber P1 pump stroke (expelling a volume of fresh dialysate from pump chamber P1 to heater bag).
   (i) Close inlet path F3 to pump chamber P1, while opening inlet path F3 to pump chamber P2. Actuate valve D3 to supply high-relative negative pressure to valve actuator VA5, opening cassette valve station V5. Actuate valves C2 to C4; D4; and D5 to supply high-relative positive pressure to valve actuators VA6 to VA10, closing cassette valve stations V6 to V10.
   (ii) Open outlet path F1 to pump chamber P1, while closing outlet path F1 to pump chamber P2. Actuate valve C0 to supply high-relative negative pressure to valve actuator VA1, opening cassette valve station V1. Actuate valves C1; D1; and D2 to supply high-relative positive pressure to valve actuators VA2 to VA4, closing cassette valve station V2 to V4.
   (iii) Flex the diaphragm underlying actuator PA1 in. Actuate valve A4 to supply high-relative positive pressure to pump actuator PA1.
   (iv) Flex the diaphragm underlying actuator PA2 out. Actuate valve B4 to supply high-relative negative pressure to pump actuator PA2.

Once the last fill solution has been heated, it is transferred to the patient in a fill cycle as described above (and as FIG. 32 shows).

According to one aspect of the invention, every important aspect of the APD procedure is controlled by fluid pressure. Fluid pressure moves liquid through the delivery set, emulating gravity flow conditions based upon either fixed or variable headheight conditions. Fluid pressure controls the operation of the valves that direct liquid among the multiple destinations and sources. Fluid pressure serves to seal the cassette within the actuator and provide a failsafe occlusion of the associated tubing when conditions warrant. Fluid pressure is the basis from which delivered liquid volume measurements are made, from which air entrapped in the liquid is detected and elimination, and from which occluded liquid flow conditions are detected and diagnosed.

According to another aspect of the invention, the cassette serves to organize and manifold the multiple lengths of tubing and bags that peritoneal dialysis requires. The cassette also serves to centralize all pumping and valving activities required in an automated peritoneal dialysis procedure, while at the same time serving as an effective sterility barrier.

Various features of the invention are set forth in the following claims.

We claim:

1. An automated peritoneal dialysis system including
   means for establishing flow communication with a patient's peritoneal cavity through a pumping mechanism,
   actuator means for operating the pumping mechanism to:
   (i) drain spent peritoneal dialysis liquid from the peritoneal cavity through, and
   (ii) infuse fresh dialysis liquid from a source into the peritoneal cavity,
   control means operable in a first mode directing operation of the actuator means to conduct a first peritoneal dialysis modality and operable in a second mode directing operation of the actuator means to conduct a second peritoneal dialysis modality different than the first modality including
   a first interface including input means for a user to select the first mode or the second mode,
   a second interface including adjustment means for a user to adjust one or more individual therapy parameters of the selected modality,
   first verification means for (i) comparing individual user-adjusted parameters to predetermined individual parameter limits; (ii) generating an error signal when an individual user-adjusted parameter is outside the predetermined individual parameter limits; and (iii) allowing adjustment of the individual parameter when it is within the predetermined individual parameter limits, and
   second verification means for (i) analyzing the individual therapy parameters allowed by the first verification means to verify that the allowed individual therapy parameters taken together satisfy predetermined composite therapy criteria comprising consideration of at least resulting dwell time or required number of cycles; (ii) returning the user to the second interface to readjust one or more individual therapy parameters when the composite therapy criteria are not satisfied; and (iii) permitting operation of the control means in the selected mode only when the composite therapy criteria are satisfied.

2. A system according to claim 1
   wherein the first modality includes at least continuous cycling peritoneal dialysis or intermittent peritoneal dialysis, and
   wherein the adjustment means for the first modality allows at least one of the following individual therapy parameters to be adjusted in response to input from the user: (1) the total dialysate volume to be infused during the therapy session; (2) the total time allotted for the therapy; (3) the volume to be infused during each fill phase; (4) the final volume to be left in the patient at the end of the session; and (5) a different dextrose concentration for the last fill volume.

3. A system according to claim 2
wherein the second modality includes at least tidal peritoneal dialysis, and
wherein the adjustment means for the first modality allows at least one of the following individual therapy parameters to be adjusted in response to input from the user: (1) the total dialysate volume to be infused during the therapy session; (2) the total time allotted for the therapy; (3) the volume to be infused during the initial tidal fill phase; (4) the final volume to be left in the patient at the end of the session; (5) a different dextrose concentration for the last fill volume; and (6) the fill volume to be infused and drained periodically, expressed as a percentage of the total therapy volume; (7) the number of full drains in the therapy session; and (8) the total ultrafiltrate expected from the patient during the session.

4. A system according to claim 3
wherein the second verification means that analyzes the individual therapy parameters for tidal peritoneal dialysis includes the predetermined composite therapy criteria comprising comparing the expected ultrafiltrate to a predetermined percentage of selected therapy value.

* * * * *

UNITED STATES PATENT AND TRADEMARK OFFICE
CERTIFICATE OF CORRECTION

| | |
|---|---|
| PATENT NO. | : 5,324,422 |
| APPLICATION NO. | : 08/025547 |
| DATED | : June 28, 1994 |
| INVENTOR(S) | : Lisa Colleran et al. |

It is certified that error appears in the above-identified patent and that said Letters Patent is hereby corrected as shown below:

IN THE CLAIMS:

In Claim 3, column 39, line 12, change "wherein the adjustment means for the first modality" to --wherein the adjustment means for the second modality--.

Signed and Sealed this

Twenty-eighth Day of August, 2007

JON W. DUDAS
*Director of the United States Patent and Trademark Office*